US012691209B2

(12) United States Patent
Julian et al.

(10) Patent No.: US 12,691,209 B2
(45) Date of Patent: Jul. 28, 2026

(54) MOLDED OR EXTRUDED FLUID COLLECTION DEVICES, AND RELATED SYSTEMS AND METHODS

(71) Applicant: PUREWICK CORPORATION, Covington, GA (US)

(72) Inventors: Alexandra Julian, Elmhurst, IL (US); Joseph Ranalletta, Greenville, SC (US); Gonghao Wang, Cary, NC (US); John Hayes, Raleigh, NC (US)

(73) Assignee: PUREWICK CORPORATION, Covington, GA (US)

( * ) Notice: Subject to any disclaimer, the term of this patent is extended or adjusted under 35 U.S.C. 154(b) by 148 days.

(21) Appl. No.: 18/294,370

(22) PCT Filed: Aug. 1, 2022

(86) PCT No.: PCT/US2022/039018
§ 371 (c)(1),
(2) Date: Feb. 1, 2024

(87) PCT Pub. No.: WO2023/014639
PCT Pub. Date: Feb. 9, 2023

(65) Prior Publication Data
US 2025/0082836 A1      Mar. 13, 2025

Related U.S. Application Data

(60) Provisional application No. 63/228,252, filed on Aug. 2, 2021.

(51) Int. Cl.
A61F 5/451      (2006.01)
A61M 1/00      (2006.01)

(52) U.S. Cl.
CPC .............. *A61M 1/60* (2021.05); *A61F 5/451* (2013.01); *A61M 2202/0496* (2013.01); *A61M 2207/00* (2013.01)

(58) Field of Classification Search
CPC ............ A61M 1/60; A61M 2202/0496; A61M 2207/00; A61F 5/451
See application file for complete search history.

(56) References Cited

U.S. PATENT DOCUMENTS 737,443 A      8/1903   Mooers
1,015,905 A      1/1912   Northrop
(Continued)

FOREIGN PATENT DOCUMENTS

AU      2018216821 A1      8/2019
AU      2021299304 A1      2/2023
(Continued)

OTHER PUBLICATIONS

US 9,908,683 B2, 03/2018, Sandhausen et al. (withdrawn)
(Continued)

*Primary Examiner* — Guy K Townsend
(74) *Attorney, Agent, or Firm* — Ballard Spahr LLP

(57) ABSTRACT

Examples relate to fluid collection devices, and related systems and methods. In some embodiments, a fluid collection device includes a fluid impermeable barrier and an elongated body that is at least partially fluid permeable. The fluid impermeable barrier has a distal end region and a proximal end region defining an aperture sized and dimensioned to have urine drawn therethrough by a vacuum source. The elongated body has a portion of the body that is free from being covered by the fluid impermeable barrier between the distal end region and the proximal end region and positioned on the fluid collection device to receive urine discharged from a urethra at least proximate to the portion of the body. The fluid collection device includes at least one of the fluid impermeable barrier being an injection molded fluid impermeable barrier or the body includes at least an extruded support.

15 Claims, 12 Drawing Sheets

(56)                    References Cited

U.S. PATENT DOCUMENTS

| | | | |
|---|---|---|---|
| 1,032,841 A | 7/1912 | Koenig | |
| 1,178,644 A | 4/1916 | Johnson | |
| 1,387,726 A | 8/1921 | Karge | |
| 1,742,080 A | 12/1929 | Jones | |
| 1,979,899 A | 11/1934 | Obrien et al. | |
| 2,241,010 A | 5/1941 | Chipley | |
| 2,262,772 A | 11/1941 | Peder | |
| 2,326,881 A | 8/1943 | Packer | |
| 2,379,346 A | 6/1945 | Farrell | |
| 2,485,555 A | 10/1949 | Bester | |
| 2,571,357 A | 10/1951 | Charles | |
| 2,613,670 A | 10/1952 | Edward | |
| 2,616,426 A | 11/1952 | Adele | |
| 2,644,234 A | 7/1953 | Earl | |
| 2,648,335 A | 8/1953 | Chambers | |
| 2,789,560 A | 4/1957 | Weimer | |
| 2,859,786 A | 11/1958 | Tupper | |
| 2,944,551 A | 7/1960 | Carl | |
| 2,968,046 A * | 1/1961 | Duke | A61G 9/006 |
| | | | 604/149 |
| 2,971,512 A | 2/1961 | Reinhardt | |
| 3,032,038 A | 5/1962 | Swinn | |
| 3,077,883 A | 2/1963 | Hill | |
| 3,087,938 A | 4/1963 | Hans et al. | |
| 3,114,916 A | 12/1963 | Hadley | |
| 3,169,528 A | 2/1965 | Knox et al. | |
| 3,171,506 A | 3/1965 | Therkel | |
| 3,175,719 A | 3/1965 | Herndon | |
| 3,194,238 A | 7/1965 | Breece | |
| 3,198,994 A | 8/1965 | Hildebrandt et al. | |
| 3,221,742 A | 12/1965 | Egon | |
| 3,312,221 A | 4/1967 | Overment | |
| 3,312,981 A | 4/1967 | Mcguire et al. | |
| 3,349,768 A | 10/1967 | Keane | |
| 3,362,590 A | 1/1968 | Gene | |
| 3,366,116 A | 1/1968 | Huck | |
| 3,368,564 A | 2/1968 | Selix | |
| 3,398,848 A | 8/1968 | Donovan | |
| 3,400,717 A | 9/1968 | Bruce et al. | |
| 3,406,688 A | 10/1968 | Bruce | |
| 3,424,163 A * | 1/1969 | Gravdahl | A61F 13/51121 |
| | | | 604/377 |
| 3,425,471 A | 2/1969 | Yates | |
| 3,434,565 A | 3/1969 | Fischer | |
| 3,511,241 A | 5/1970 | Lee | |
| 3,512,185 A | 5/1970 | Ellis | |
| 3,520,300 A | 7/1970 | Flower | |
| 3,528,423 A | 9/1970 | Lee | |
| 3,608,552 A | 9/1971 | Broerman | |
| 3,613,123 A | 10/1971 | Langstrom | |
| 3,648,700 A | 3/1972 | Warner | |
| 3,651,810 A | 3/1972 | Ormerod | |
| 3,661,155 A | 5/1972 | Lindan | |
| 3,683,918 A | 8/1972 | Pizzella | |
| 3,699,815 A | 10/1972 | Holbrook | |
| 3,721,243 A | 3/1973 | Greth et al. | |
| 3,726,277 A | 4/1973 | Hirschman | |
| 3,742,952 A | 7/1973 | Magers et al. | |
| 3,742,953 A | 7/1973 | Lee | |
| 3,757,355 A | 9/1973 | Allen et al. | |
| 3,788,324 A | 1/1974 | Lim | |
| 3,843,016 A | 10/1974 | Bornhorst et al. | |
| 3,863,638 A | 2/1975 | Rogers et al. | |
| 3,863,798 A | 2/1975 | Kurihara et al. | |
| 3,864,759 A | 2/1975 | Horiuchi | |
| 3,865,109 A | 2/1975 | Elmore et al. | |
| 3,881,486 A | 5/1975 | Fenton | |
| 3,881,489 A | 5/1975 | Hartwell | |
| 3,915,189 A | 10/1975 | Holbrook et al. | |
| 3,931,650 A | 1/1976 | Miller | |
| 3,964,786 A | 6/1976 | Mashuda | |
| 3,998,228 A | 12/1976 | Poidomani | |
| 3,999,550 A | 12/1976 | Martin | |
| 4,006,793 A | 2/1977 | Robinson | |
| 4,015,604 A | 4/1977 | Csillag | |
| 4,020,843 A | 5/1977 | Kanall | |
| 4,022,211 A | 5/1977 | Timmons et al. | |
| 4,022,213 A | 5/1977 | Stein | |
| 4,027,776 A | 6/1977 | Douglas | |
| 4,031,897 A | 6/1977 | Graetz | |
| 4,064,962 A | 12/1977 | Hunt | |
| 4,069,817 A | 1/1978 | Fenole et al. | |
| 4,084,589 A | 4/1978 | Kulvi | |
| 4,096,897 A | 6/1978 | Cammarata | |
| 4,116,197 A | 9/1978 | Bermingham | |
| 4,140,739 A | 2/1979 | Cotten | |
| 4,180,178 A | 12/1979 | Turner | |
| 4,187,953 A | 2/1980 | Turner | |
| 4,194,508 A | 3/1980 | Anderson | |
| 4,197,849 A | 4/1980 | Bostick | |
| 4,200,102 A * | 4/1980 | Duhamel | A61F 5/451 |
| | | | 604/353 |
| 4,202,058 A | 5/1980 | Anderson | |
| 4,203,503 A | 5/1980 | Bertotti et al. | |
| 4,209,076 A | 6/1980 | Bertotti et al. | |
| 4,223,677 A | 9/1980 | Anderson | |
| 4,233,025 A | 11/1980 | Larson et al. | |
| 4,233,978 A | 11/1980 | Hickey | |
| 4,246,901 A | 1/1981 | Frosch et al. | |
| 4,253,542 A | 3/1981 | Ruspa et al. | |
| 4,257,418 A | 3/1981 | Hessner | |
| 4,270,539 A * | 6/1981 | Frosch | A61F 5/455 |
| | | | 604/347 |
| 4,280,498 A | 7/1981 | Jensen | |
| 4,281,655 A | 8/1981 | Terauchi | |
| 4,292,916 A | 10/1981 | Bradley et al. | |
| 4,330,239 A | 5/1982 | Gannaway | |
| 4,345,341 A | 8/1982 | Saito | |
| 4,349,029 A | 9/1982 | Mott | |
| 4,352,356 A | 10/1982 | Tong | |
| 4,356,012 A | 10/1982 | Hofstetter | |
| 4,360,933 A | 11/1982 | Kimura et al. | |
| 4,365,363 A | 12/1982 | Windauer | |
| 4,375,841 A | 3/1983 | Vielbig | |
| 4,387,726 A | 6/1983 | Denard | |
| 4,403,991 A | 9/1983 | Hill | |
| 4,421,511 A | 12/1983 | Steer et al. | |
| 4,425,130 A | 1/1984 | Desmarais | |
| 4,446,986 A | 5/1984 | Bowen et al. | |
| 4,453,938 A | 6/1984 | Brendling | |
| 4,457,314 A | 7/1984 | Knowles | |
| 4,457,758 A | 7/1984 | Norton | |
| 4,476,879 A | 10/1984 | Jackson | |
| 4,512,771 A | 4/1985 | Norton | |
| 4,526,688 A | 7/1985 | Schmidt et al. | |
| 4,528,703 A | 7/1985 | Kraus | |
| 4,533,354 A | 8/1985 | Jensen | |
| 4,533,357 A | 8/1985 | Hall | |
| D280,438 S | 9/1985 | Wendt | |
| 4,551,141 A | 11/1985 | Mcneil | |
| 4,553,968 A | 11/1985 | Komis | |
| 4,568,341 A | 2/1986 | Mitchell et al. | |
| 4,581,026 A | 4/1986 | Schneider | |
| 4,583,983 A | 4/1986 | Einhorn et al. | |
| 4,589,516 A | 5/1986 | Inoue et al. | |
| 4,601,716 A | 7/1986 | Smith | |
| 4,610,675 A | 9/1986 | Triunfol | |
| 4,620,333 A | 11/1986 | Ritter | |
| 4,626,250 A | 12/1986 | Schneider | |
| 4,627,846 A | 12/1986 | Ternstroem | |
| 4,631,061 A * | 12/1986 | Martin | A61F 5/451 |
| | | | 604/323 |
| 4,650,477 A | 3/1987 | Johnson | |
| 4,655,754 A | 4/1987 | Richmond et al. | |
| 4,656,675 A | 4/1987 | Fajnsztajn | |
| 4,681,570 A | 7/1987 | Dalton | |
| 4,681,572 A | 7/1987 | Tokarz et al. | |
| 4,681,577 A | 7/1987 | Stern et al. | |
| 4,692,160 A | 9/1987 | Nussbaumer | |
| 4,707,864 A | 11/1987 | Ikematsu et al. | |
| 4,713,065 A | 12/1987 | Koot | |
| 4,713,066 A | 12/1987 | Komis | |
| 4,723,953 A | 2/1988 | Pratt et al. | |
| 4,735,841 A | 4/1988 | Sourdet | |

(56)                References Cited

U.S. PATENT DOCUMENTS

| | | | |
|---|---|---|---|
| 4,743,236 A | 5/1988 | Manschot | |
| 4,747,166 A * | 5/1988 | Kuntz | A61F 5/455 |
| | | | 4/144.1 |
| 4,752,944 A | 6/1988 | Conrads et al. | |
| 4,759,753 A | 7/1988 | Schneider et al. | |
| 4,769,215 A | 9/1988 | Ehrenkranz | |
| 4,771,484 A | 9/1988 | Mozell | |
| 4,772,280 A | 9/1988 | Rooyakkers | |
| 4,775,458 A | 10/1988 | Forester | |
| 4,784,654 A | 11/1988 | Beecher | |
| 4,790,830 A | 12/1988 | Hamacher | |
| 4,790,835 A | 12/1988 | Elias | |
| 4,791,686 A | 12/1988 | Taniguchi et al. | |
| 4,795,449 A | 1/1989 | Schneider et al. | |
| 4,798,603 A | 1/1989 | Meyer et al. | |
| 4,799,928 A | 1/1989 | Crowley | |
| 4,804,377 A | 2/1989 | Hanifl et al. | |
| 4,812,053 A | 3/1989 | Bhattacharjee | |
| 4,813,943 A | 3/1989 | Smith | |
| 4,820,291 A | 4/1989 | Terauchi et al. | |
| 4,820,297 A | 4/1989 | Kaufman et al. | |
| 4,841,728 A | 6/1989 | Jean et al. | |
| 4,846,818 A | 7/1989 | Keldahl et al. | |
| 4,846,819 A | 7/1989 | Welch | |
| 4,846,824 A | 7/1989 | Lassen et al. | |
| 4,846,909 A | 7/1989 | Klug et al. | |
| 4,865,595 A | 9/1989 | Heyden | |
| 4,880,417 A | 11/1989 | Yabrov et al. | |
| 4,882,794 A | 11/1989 | Stewart | |
| 4,883,465 A | 11/1989 | Brennan | |
| 4,886,498 A | 12/1989 | Newton | |
| 4,886,508 A * | 12/1989 | Washington | A61F 5/455 |
| | | | 604/347 |
| 4,886,509 A | 12/1989 | Mattsson | |
| 4,889,532 A | 12/1989 | Metz et al. | |
| 4,889,533 A | 12/1989 | Beecher | |
| 4,890,691 A | 1/1990 | Ching-Ho | |
| 4,895,140 A | 1/1990 | Bellak | |
| 4,903,254 A | 2/1990 | Haas | |
| 4,904,248 A | 2/1990 | Vaillancourt | |
| 4,905,692 A | 3/1990 | More | |
| 4,911,262 A | 3/1990 | Tani et al. | |
| 4,930,997 A | 6/1990 | Bennett | |
| 4,936,838 A | 6/1990 | Cross et al. | |
| 4,950,262 A | 8/1990 | Takagi | |
| 4,955,922 A | 9/1990 | Terauchi | |
| 4,957,487 A | 9/1990 | Gerow | |
| 4,965,460 A | 10/1990 | Tanaka et al. | |
| 4,986,823 A | 1/1991 | Anderson et al. | |
| 4,987,849 A | 1/1991 | Sherman | |
| 5,002,541 A | 3/1991 | Conkling et al. | |
| 5,004,463 A | 4/1991 | Nigay | |
| 5,013,308 A | 5/1991 | Sullivan et al. | |
| 5,031,248 A | 7/1991 | Kemper | |
| 5,045,077 A | 9/1991 | Blake | |
| 5,045,283 A | 9/1991 | Patel | |
| 5,049,144 A * | 9/1991 | Payton | A61F 5/455 |
| | | | 600/574 |
| 5,053,339 A | 10/1991 | Patel | |
| 5,057,092 A | 10/1991 | Webster | |
| 5,058,088 A | 10/1991 | Haas et al. | |
| 5,071,347 A | 12/1991 | Mcguire | |
| 5,078,707 A | 1/1992 | Peter | |
| 5,084,037 A | 1/1992 | Barnett | |
| 5,100,396 A | 3/1992 | Zamierowski | |
| 5,102,404 A | 4/1992 | Goldberg et al. | |
| 5,112,324 A | 5/1992 | Wallace | |
| 5,134,994 A | 8/1992 | Say | |
| 5,137,033 A | 8/1992 | Norton | |
| 5,147,301 A | 9/1992 | Ruvio | |
| 5,176,667 A | 1/1993 | Debring | |
| 5,195,997 A | 3/1993 | Carns | |
| 5,196,654 A | 3/1993 | Diflora et al. | |
| 5,199,444 A | 4/1993 | Wheeler | |
| 5,203,699 A | 4/1993 | Mcguire | |
| 5,244,458 A | 9/1993 | Takasu | |
| 5,246,454 A | 9/1993 | Peterson | |
| 5,267,988 A | 12/1993 | Farkas | |
| 5,275,307 A | 1/1994 | Freese | |
| 5,282,795 A | 2/1994 | Finney | |
| 5,295,979 A | 3/1994 | Delaurentis et al. | |
| 5,295,983 A | 3/1994 | Kubo | |
| 5,300,052 A | 4/1994 | Kubo | |
| 5,304,749 A | 4/1994 | Crandell | |
| 5,312,383 A | 5/1994 | Kubalak | |
| 5,318,550 A | 6/1994 | Cermak et al. | |
| 5,330,457 A | 7/1994 | Cohen | |
| 5,330,459 A | 7/1994 | Lavon et al. | |
| 5,334,174 A | 8/1994 | Street | |
| 5,334,176 A | 8/1994 | Buenger et al. | |
| 5,340,840 A | 8/1994 | Park et al. | |
| 5,382,244 A | 1/1995 | Telang | |
| 5,397,315 A | 3/1995 | Schmidt et al. | |
| 5,409,014 A | 4/1995 | Napoli et al. | |
| 5,409,475 A | 4/1995 | Steer | |
| 5,411,495 A | 5/1995 | Willingham | |
| 5,423,784 A | 6/1995 | Metz | |
| 5,423,788 A | 6/1995 | Rollins et al. | |
| 5,437,836 A | 8/1995 | Yamada | |
| 5,456,246 A | 10/1995 | Schmieding et al. | |
| 5,466,229 A * | 11/1995 | Elson | A61M 1/78 |
| | | | 604/323 |
| 5,478,334 A | 12/1995 | Bernstein | |
| 5,499,977 A | 3/1996 | Marx | |
| 5,543,042 A | 8/1996 | Filan et al. | |
| D373,928 S | 9/1996 | Green | |
| 5,582,604 A | 12/1996 | Ahr et al. | |
| 5,592,950 A | 1/1997 | Kopelowicz | |
| 5,593,389 A | 1/1997 | Chang | |
| 5,605,161 A | 2/1997 | Cross | |
| 5,614,699 A | 3/1997 | Yashiro et al. | |
| 5,618,277 A | 4/1997 | Goulter | |
| 5,628,735 A | 5/1997 | Skow | |
| 5,632,736 A | 5/1997 | Block | |
| 5,636,643 A | 6/1997 | Argenta et al. | |
| 5,637,104 A | 6/1997 | Ball et al. | |
| 5,662,633 A | 9/1997 | Doak et al. | |
| 5,674,212 A * | 10/1997 | Osborn, III | A61F 13/15 |
| | | | 604/385.16 |
| 5,678,564 A * | 10/1997 | Lawrence | A61F 5/455 |
| | | | 600/573 |
| 5,681,297 A | 10/1997 | Hashimoto et al. | |
| 5,687,429 A | 11/1997 | Rahlff | |
| 5,695,485 A | 12/1997 | Duperret et al. | |
| 5,700,254 A | 12/1997 | Mcdowall et al. | |
| 5,701,612 A | 12/1997 | Daneshvar | |
| 5,705,777 A | 1/1998 | Flanigan et al. | |
| 5,735,835 A | 4/1998 | Holland | |
| 5,735,837 A | 4/1998 | Ishikawa | |
| 5,752,944 A | 5/1998 | Dann et al. | |
| 5,763,333 A | 6/1998 | Suzuki et al. | |
| 5,772,644 A | 6/1998 | Bark et al. | |
| 5,792,132 A | 8/1998 | Garcia | |
| 5,827,243 A | 10/1998 | Palestrant | |
| 5,827,247 A | 10/1998 | Kay | |
| 5,827,250 A | 10/1998 | Fujioka et al. | |
| 5,827,257 A | 10/1998 | Fujioka et al. | |
| D401,699 S | 11/1998 | Herchenbach et al. | |
| 5,859,393 A | 1/1999 | Cummins et al. | |
| 5,865,378 A | 2/1999 | Hollinshead et al. | |
| 5,873,869 A | 2/1999 | Hammons et al. | |
| 5,876,393 A | 3/1999 | Ahr et al. | |
| 5,887,291 A | 3/1999 | Bellizzi | |
| 5,891,125 A | 4/1999 | Plumley | |
| 5,894,608 A | 4/1999 | Birbara | |
| 5,895,349 A | 4/1999 | Tihon | |
| D409,303 S | 5/1999 | Oepping | |
| 5,911,222 A | 6/1999 | Lawrence et al. | |
| 5,956,782 A | 9/1999 | Olguin | |
| 5,957,904 A | 9/1999 | Holland | |
| 5,968,026 A | 10/1999 | Osborn et al. | |
| 5,972,505 A | 10/1999 | Phillips et al. | |
| 6,007,526 A | 12/1999 | Passalaqua et al. | |
| 6,039,060 A | 3/2000 | Rower | |

(56) References Cited

U.S. PATENT DOCUMENTS

| | | | |
|---|---|---|---|
| 6,050,983 A | 4/2000 | Moore et al. | |
| 6,059,762 A | 5/2000 | Boyer et al. | |
| 6,063,064 A | 5/2000 | Tuckey et al. | |
| 6,098,625 A | 8/2000 | Winkler | |
| 6,105,174 A | 8/2000 | Karlsten et al. | |
| 6,113,582 A | 9/2000 | Dwork | |
| 6,117,163 A * | 9/2000 | Bierman | A61M 25/02 |
| | | | 606/232 |
| 6,123,398 A * | 9/2000 | Arai | B60T 8/17552 |
| | | | 303/151 |
| 6,129,718 A | 10/2000 | Wada et al. | |
| 6,131,964 A | 10/2000 | Sareshwala | |
| 6,152,902 A | 11/2000 | Christian et al. | |
| 6,164,569 A | 12/2000 | Hollinshead et al. | |
| 6,177,606 B1 | 1/2001 | Etheredge et al. | |
| 6,209,142 B1 | 4/2001 | Mattsson et al. | |
| 6,220,050 B1 | 4/2001 | Cooksey | |
| 6,244,311 B1 | 6/2001 | Hand et al. | |
| 6,248,096 B1 | 6/2001 | Dwork et al. | |
| 6,263,887 B1 | 7/2001 | Dunn | |
| 6,283,246 B1 | 9/2001 | Nishikawa | |
| 6,296,627 B1 | 10/2001 | Edwards | |
| 6,311,339 B1 | 11/2001 | Kraus | |
| 6,316,688 B1 | 11/2001 | Hammons et al. | |
| 6,336,919 B1 | 1/2002 | Davis et al. | |
| 6,338,729 B1 | 1/2002 | Wada et al. | |
| 6,352,525 B1 | 3/2002 | Wakabayashi | |
| 6,394,988 B1 | 5/2002 | Hashimoto | |
| 6,395,956 B1 | 5/2002 | Glasgow et al. | |
| 6,398,742 B1 * | 6/2002 | Kim | A61F 5/4556 |
| | | | 4/144.3 |
| 6,406,463 B1 | 6/2002 | Brown | |
| 6,409,712 B1 | 6/2002 | Dutari et al. | |
| 6,415,888 B2 | 7/2002 | An et al. | |
| 6,416,500 B1 | 7/2002 | Wada et al. | |
| 6,423,045 B1 | 7/2002 | Wise et al. | |
| 6,428,521 B1 | 8/2002 | Droll | |
| 6,428,522 B1 | 8/2002 | Dipalma et al. | |
| 6,446,454 B1 | 9/2002 | Lee et al. | |
| 6,461,340 B1 | 10/2002 | Lenker et al. | |
| 6,467,570 B1 | 10/2002 | Herold | |
| 6,475,198 B1 | 11/2002 | Lipman et al. | |
| 6,479,726 B1 | 11/2002 | Cole et al. | |
| 6,491,673 B1 | 12/2002 | Palumbo et al. | |
| 6,508,794 B1 | 1/2003 | Palumbo et al. | |
| 6,524,292 B1 | 2/2003 | Dipalma et al. | |
| 6,526,603 B1 | 3/2003 | Murphy | |
| 6,540,729 B1 | 4/2003 | Wada et al. | |
| 6,547,771 B2 | 4/2003 | Robertson et al. | |
| 6,551,293 B1 | 4/2003 | Mitchell | |
| 6,569,133 B2 | 5/2003 | Cheng et al. | |
| D476,518 S | 7/2003 | Doppelt | |
| 6,592,560 B2 | 7/2003 | Snyder et al. | |
| 6,610,038 B1 | 8/2003 | Dipalma et al. | |
| 6,618,868 B2 | 9/2003 | Minnick | |
| 6,620,142 B1 | 9/2003 | Flueckiger | |
| 6,629,651 B1 | 10/2003 | Male et al. | |
| 6,635,037 B1 | 10/2003 | Bennett | |
| 6,635,038 B2 | 10/2003 | Scovel | |
| 6,652,495 B1 | 11/2003 | Walker | |
| 6,666,850 B1 | 12/2003 | Ahr et al. | |
| 6,685,684 B1 | 2/2004 | Falconer | |
| 6,695,828 B1 | 2/2004 | Dipalma et al. | |
| 6,699,174 B1 | 3/2004 | Bennett | |
| 6,700,034 B1 | 3/2004 | Lindsay et al. | |
| 6,702,793 B1 | 3/2004 | Sweetser et al. | |
| 6,706,027 B2 * | 3/2004 | Harvie | A61F 5/453 |
| | | | 604/326 |
| 6,732,384 B2 * | 5/2004 | Scott | A47K 11/12 |
| | | | 4/144.1 |
| 6,736,977 B1 | 5/2004 | Hall et al. | |
| 6,740,066 B2 * | 5/2004 | Wolff | A61F 5/451 |
| | | | 604/323 |
| 6,764,477 B1 | 7/2004 | Chen et al. | |
| 6,783,519 B2 | 8/2004 | Samuelsson | |
| 6,796,974 B2 | 9/2004 | Palumbo et al. | |
| 6,814,547 B2 | 11/2004 | Childers et al. | |
| 6,848,719 B2 * | 2/2005 | Rowley | F16L 9/147 |
| | | | 285/55 |
| 6,849,065 B2 | 2/2005 | Schmidt et al. | |
| 6,857,137 B2 | 2/2005 | Otto | |
| 6,885,690 B2 | 4/2005 | Aggerstam et al. | |
| 6,888,044 B2 | 5/2005 | Fell et al. | |
| 6,893,425 B2 | 5/2005 | Dunn et al. | |
| 6,912,737 B2 | 7/2005 | Ernest et al. | |
| 6,918,899 B2 * | 7/2005 | Harvie | A61F 5/451 |
| | | | 604/326 |
| 6,979,324 B2 * | 12/2005 | Bybordi | A61M 1/916 |
| | | | 604/327 |
| 7,018,366 B2 * | 3/2006 | Easter | A61F 5/451 |
| | | | 604/327 |
| 7,066,411 B2 | 6/2006 | Male et al. | |
| 7,087,043 B2 | 8/2006 | Dolan | |
| 7,122,023 B1 | 10/2006 | Hinoki | |
| 7,125,399 B2 | 10/2006 | Miskie | |
| 7,131,964 B2 | 11/2006 | Harvie | |
| 7,135,012 B2 * | 11/2006 | Harvie | A61F 5/453 |
| | | | 604/326 |
| 7,141,043 B2 * | 11/2006 | Harvie | A61F 5/451 |
| | | | 604/326 |
| D533,972 S | 12/2006 | La | |
| 7,160,273 B2 | 1/2007 | Greter et al. | |
| 7,166,092 B2 | 1/2007 | Elson et al. | |
| 7,171,699 B2 | 2/2007 | Ernest et al. | |
| 7,171,871 B2 | 2/2007 | Kozak | |
| 7,179,951 B2 | 2/2007 | Krishnaswamy-mirle et al. | |
| 7,181,781 B1 | 2/2007 | Trabold et al. | |
| 7,186,245 B1 | 3/2007 | Cheng et al. | |
| 7,192,424 B2 | 3/2007 | Cooper | |
| 7,219,764 B1 | 5/2007 | Forbes | |
| 7,220,250 B2 * | 5/2007 | Suzuki | A61F 5/451 |
| | | | 604/328 |
| D562,975 S | 2/2008 | Otto | |
| 7,335,189 B2 * | 2/2008 | Harvie | A61F 5/451 |
| | | | 604/326 |
| 7,358,282 B2 | 4/2008 | Krueger et al. | |
| 7,390,320 B2 * | 6/2008 | Machida | A61F 5/455 |
| | | | 4/144.1 |
| 7,438,706 B2 | 10/2008 | Koizumi et al. | |
| 7,488,310 B2 | 2/2009 | Yang | |
| 7,491,194 B1 | 2/2009 | Oliwa | |
| D591,106 S | 4/2009 | Dominique et al. | |
| 7,513,381 B2 | 4/2009 | Heng et al. | |
| 7,520,872 B2 | 4/2009 | Biggie et al. | |
| D593,801 S | 6/2009 | Wilson et al. | |
| 7,540,364 B2 | 6/2009 | Sanderson | |
| 7,549,511 B2 | 6/2009 | Marocco | |
| 7,549,512 B2 | 6/2009 | Newberry | |
| 7,585,293 B2 | 9/2009 | Vermaak | |
| 7,588,560 B1 | 9/2009 | Dunlop | |
| 7,637,905 B2 | 12/2009 | Saadat et al. | |
| 7,658,730 B2 | 2/2010 | Conley | |
| 7,665,359 B2 | 2/2010 | Barber | |
| 7,682,347 B2 * | 3/2010 | Parks | A61F 5/4556 |
| | | | 604/327 |
| 7,687,004 B2 | 3/2010 | Allen | |
| 7,695,459 B2 | 4/2010 | Gilbert et al. | |
| 7,695,460 B2 | 4/2010 | Wada et al. | |
| 7,699,818 B2 | 4/2010 | Gilbert | |
| 7,699,831 B2 * | 4/2010 | Bengtson | A61M 27/00 |
| | | | 604/313 |
| 7,722,584 B2 | 5/2010 | Tanaka et al. | |
| 7,727,206 B2 | 6/2010 | Gorres | |
| 7,740,620 B2 | 6/2010 | Gilbert et al. | |
| 7,749,205 B2 * | 7/2010 | Tazoe | A61F 5/451 |
| | | | 604/320 |
| 7,755,497 B2 * | 7/2010 | Wada | A61F 5/451 |
| | | | 340/604 |
| 7,766,887 B2 | 8/2010 | Burns et al. | |
| 7,803,144 B1 | 9/2010 | Vollrath | |
| D625,407 S | 10/2010 | Koizumi et al. | |
| 7,806,879 B2 | 10/2010 | Brooks et al. | |

(56)             References Cited

U.S. PATENT DOCUMENTS

| | | | |
|---|---|---|---|
| 7,811,272 B2 | 10/2010 | Lindsay et al. | |
| 7,815,067 B2 | 10/2010 | Matsumoto et al. | |
| 7,833,169 B2 | 11/2010 | Hannon | |
| 7,857,806 B2 | 12/2010 | Karpowicz et al. | |
| 7,866,942 B2 | 1/2011 | Harvie | |
| 7,871,385 B2 | 1/2011 | Levinson et al. | |
| 7,875,010 B2 | 1/2011 | Frazier et al. | |
| 7,901,389 B2 | 3/2011 | Mombrinie | |
| 7,927,320 B2 | 4/2011 | Goldwasser et al. | |
| 7,927,321 B2 | 4/2011 | Marland | |
| 7,931,634 B2 | 4/2011 | Swiecicki et al. | |
| 7,939,706 B2 * | 5/2011 | Okabe | A61F 5/4404 |
| | | | 604/361 |
| 7,946,443 B2 | 5/2011 | Stull et al. | |
| 7,947,025 B2 | 5/2011 | Buglino et al. | |
| 7,963,419 B2 | 6/2011 | Burney et al. | |
| 7,976,519 B2 | 7/2011 | Bubb et al. | |
| 7,981,087 B2 | 7/2011 | Gesler, III | |
| 7,993,318 B2 | 8/2011 | Olsson et al. | |
| 8,015,627 B2 | 9/2011 | Baker et al. | |
| 8,016,071 B1 | 9/2011 | Martinus et al. | |
| 8,028,460 B2 | 10/2011 | Williams | |
| 8,047,398 B2 | 11/2011 | Dimartino et al. | |
| 8,083,094 B2 | 12/2011 | Caulfield et al. | |
| 8,128,608 B2 * | 3/2012 | Thevenin | A61F 13/84 |
| | | | 604/347 |
| 8,167,860 B1 | 5/2012 | Siegel | |
| 8,181,651 B2 | 5/2012 | Pinel | |
| 8,181,819 B2 | 5/2012 | Burney et al. | |
| 8,211,063 B2 * | 7/2012 | Bierman | A61M 25/02 |
| | | | 604/179 |
| 8,221,369 B2 | 7/2012 | Parks et al. | |
| 8,241,262 B2 | 8/2012 | Mahnensmith | |
| 8,277,426 B2 | 10/2012 | Wilcox et al. | |
| 8,287,508 B1 * | 10/2012 | Sanchez | A61F 5/4404 |
| | | | 604/326 |
| 8,303,554 B2 | 11/2012 | Tsai et al. | |
| 8,322,565 B2 | 12/2012 | Caulfield et al. | |
| 8,337,477 B2 | 12/2012 | Parks et al. | |
| D674,241 S | 1/2013 | Bickert et al. | |
| 8,343,122 B2 | 1/2013 | Gorres | |
| 8,343,125 B2 | 1/2013 | Kawazoe et al. | |
| 8,353,074 B2 | 1/2013 | Krebs | |
| 8,353,886 B2 | 1/2013 | Bester et al. | |
| D676,241 S | 2/2013 | Merrill | |
| 8,388,587 B1 | 3/2013 | Gmuer et al. | |
| 8,388,588 B2 | 3/2013 | Wada et al. | |
| D679,807 S | 4/2013 | Burgess et al. | |
| 8,425,482 B2 | 4/2013 | Khoubnazar | |
| 8,434,586 B2 | 5/2013 | Pawelski et al. | |
| 8,449,510 B2 | 5/2013 | Martini et al. | |
| D684,260 S | 6/2013 | Lund et al. | |
| 8,470,230 B2 | 6/2013 | Caulfield et al. | |
| 8,479,941 B2 | 7/2013 | Matsumoto et al. | |
| 8,479,949 B2 | 7/2013 | Henkel | |
| 8,500,719 B1 | 8/2013 | Simpson et al. | |
| 8,512,301 B2 | 8/2013 | Ma | |
| 8,529,530 B2 | 9/2013 | Koch et al. | |
| 8,535,284 B2 | 9/2013 | Joder et al. | |
| 8,546,639 B2 * | 10/2013 | Wada | A61F 5/4401 |
| | | | 604/361 |
| 8,551,062 B2 | 10/2013 | Kay | |
| 8,551,075 B2 * | 10/2013 | Bengtson | A61M 1/84 |
| | | | 604/543 |
| 8,568,376 B2 | 10/2013 | Delattre et al. | |
| D694,404 S | 11/2013 | Burgess et al. | |
| 8,585,683 B2 | 11/2013 | Bengtson et al. | |
| 8,652,112 B2 | 2/2014 | Johannison et al. | |
| 8,669,412 B2 | 3/2014 | Fernkvist et al. | |
| D702,973 S | 4/2014 | Norland et al. | |
| 8,702,667 B1 | 4/2014 | Johnson | |
| 8,703,032 B2 | 4/2014 | Menon et al. | |
| D704,330 S | 5/2014 | Cicatelli | |
| D704,510 S | 5/2014 | Mason et al. | |
| D705,423 S | 5/2014 | Walsh Cutler | |
| D705,926 S | 5/2014 | Burgess et al. | |
| 8,714,394 B2 | 5/2014 | Wulf | |
| 8,715,267 B2 | 5/2014 | Bengtson et al. | |
| 8,740,852 B2 | 6/2014 | Aviles | |
| 8,757,425 B2 | 6/2014 | Copeland | |
| 8,777,032 B2 * | 7/2014 | Biesecker | B65D 43/0212 |
| | | | 220/780 |
| 8,808,260 B2 | 8/2014 | Koch et al. | |
| 8,864,730 B2 | 10/2014 | Conway et al. | |
| 8,881,923 B2 | 11/2014 | Higginson | |
| 8,882,731 B2 | 11/2014 | Suzuki et al. | |
| 8,936,585 B2 | 1/2015 | Carson et al. | |
| D729,581 S | 5/2015 | Boroski | |
| 9,028,460 B2 * | 5/2015 | Medeiros | A61F 5/451 |
| | | | 604/347 |
| 9,056,698 B2 | 6/2015 | Noer | |
| 9,078,792 B2 | 7/2015 | Ruiz | |
| 9,145,879 B2 | 9/2015 | Pirovano et al. | |
| 9,173,602 B2 | 11/2015 | Gilbert | |
| 9,173,799 B2 * | 11/2015 | Tanimoto | A61F 5/453 |
| 9,187,220 B2 | 11/2015 | Biesecker et al. | |
| 9,199,772 B2 | 12/2015 | Krippendorf | |
| 9,233,020 B2 * | 1/2016 | Matsumiya | A61F 5/451 |
| 9,248,058 B2 | 2/2016 | Conway et al. | |
| 9,308,118 B1 | 4/2016 | Dupree et al. | |
| 9,309,029 B2 | 4/2016 | Incorvia et al. | |
| 9,333,281 B2 | 5/2016 | Giezendanner et al. | |
| 9,381,108 B2 | 7/2016 | Longoni et al. | |
| 9,382,047 B2 | 7/2016 | Schmidtner et al. | |
| 9,402,424 B2 | 8/2016 | Roy | |
| 9,415,191 B2 | 8/2016 | Aviles | |
| 9,456,937 B2 | 10/2016 | Ellis | |
| 9,480,595 B2 | 11/2016 | Baham et al. | |
| 9,517,865 B2 | 12/2016 | Albers et al. | |
| D777,941 S | 1/2017 | Piramoon | |
| 9,533,806 B2 | 1/2017 | Ding et al. | |
| 9,550,611 B2 | 1/2017 | Hodge | |
| 9,555,930 B2 | 1/2017 | Campbell et al. | |
| 9,623,159 B2 | 4/2017 | Locke | |
| D789,522 S | 6/2017 | Burgess et al. | |
| 9,687,849 B2 | 6/2017 | Bruno et al. | |
| 9,694,949 B2 | 7/2017 | Hendricks et al. | |
| 9,709,048 B2 | 7/2017 | Kinjo | |
| 9,713,547 B2 | 7/2017 | Lee et al. | |
| 9,732,754 B2 | 8/2017 | Huang et al. | |
| 9,737,433 B2 | 8/2017 | Joh | |
| 9,752,564 B2 | 9/2017 | Arceno et al. | |
| 9,788,992 B2 | 10/2017 | Harvie | |
| D804,907 S | 12/2017 | Sandoval | |
| 9,868,564 B2 * | 1/2018 | McGirr | B65D 1/0223 |
| D814,239 S | 4/2018 | Arora | |
| D817,484 S | 5/2018 | Lafond | |
| 9,968,908 B2 | 5/2018 | Ladrech et al. | |
| 10,010,393 B1 | 7/2018 | Nguyen et al. | |
| 10,037,640 B2 | 7/2018 | Gordon | |
| 10,058,470 B2 | 8/2018 | Phillips | |
| 10,098,990 B2 | 10/2018 | Koch et al. | |
| D835,264 S | 12/2018 | Mozzicato et al. | |
| D835,779 S | 12/2018 | Mozzicato et al. | |
| D840,533 S | 2/2019 | Mozzicato et al. | |
| D840,534 S | 2/2019 | Mozzicato et al. | |
| 10,225,376 B2 | 3/2019 | Perez Martinez | |
| 10,226,376 B2 * | 3/2019 | Sanchez | A61F 5/443 |
| 10,258,517 B1 | 4/2019 | Maschino et al. | |
| D848,612 S | 5/2019 | Mozzicato et al. | |
| 10,307,305 B1 | 6/2019 | Hodges | |
| 10,335,121 B2 | 7/2019 | Desai | |
| D856,512 S | 8/2019 | Cowart et al. | |
| 10,376,406 B2 | 8/2019 | Newton | |
| 10,376,407 B2 | 8/2019 | Newton | |
| 10,390,989 B2 * | 8/2019 | Sanchez | A61D 99/00 |
| D858,144 S | 9/2019 | Fu | |
| 10,406,039 B2 | 9/2019 | Villarreal | |
| 10,407,222 B2 | 9/2019 | Allen | |
| 10,478,356 B2 | 11/2019 | Griffin | |
| 10,500,108 B1 | 12/2019 | Maschino et al. | |
| 10,502,198 B2 | 12/2019 | Stumpf et al. | |
| 10,538,366 B2 | 1/2020 | Pentelovitch et al. | |

(56) References Cited

U.S. PATENT DOCUMENTS

| | | | |
|---|---|---|---|
| 10,569,938 B2 | 2/2020 | Zhao et al. |
| 10,577,156 B2 | 3/2020 | Dagnelie et al. |
| RE47,930 E | 4/2020 | Cho |
| 10,618,721 B2 | 4/2020 | Vazin |
| D884,390 S | 5/2020 | Wang |
| 10,669,079 B2 | 6/2020 | Freedman et al. |
| D892,315 S | 8/2020 | Airy |
| 10,730,672 B2 | 8/2020 | Bertram et al. |
| 10,737,848 B2 | 8/2020 | Philip et al. |
| 10,765,854 B2 | 9/2020 | Law et al. |
| 10,766,670 B2 | 9/2020 | Kittmann |
| 10,799,386 B1 | 10/2020 | Harrison |
| 10,806,623 B2 | 10/2020 | VanMiddendorp et al. |
| 10,806,642 B2 | 10/2020 | Tagomori et al. |
| D901,214 S | 11/2020 | Hu |
| 10,849,799 B2 | 12/2020 | Nishikawa et al. |
| 10,857,025 B2 * | 12/2020 | Davis .................... A61F 5/451 |
| 10,865,017 B1 | 12/2020 | Cowart et al. |
| 10,889,412 B2 | 1/2021 | West et al. |
| 10,913,581 B2 | 2/2021 | Stahlecker |
| D912,244 S | 3/2021 | Rehm et al. |
| 10,952,889 B2 * | 3/2021 | Newton ................ A61F 5/4404 |
| 10,973,378 B2 | 4/2021 | Ryu et al. |
| 10,973,678 B2 | 4/2021 | Newton et al. |
| 10,974,874 B2 | 4/2021 | Ragias et al. |
| 11,000,401 B2 | 5/2021 | Ecklund et al. |
| 11,002,165 B2 | 5/2021 | Poulin |
| D923,365 S | 6/2021 | Wang |
| 11,020,567 B2 | 6/2021 | Rule et al. |
| 11,026,829 B2 | 6/2021 | Harvie |
| 11,027,900 B2 | 6/2021 | Liu |
| 11,045,346 B2 | 6/2021 | Argent et al. |
| D928,946 S | 8/2021 | Sanchez et al. |
| 11,090,183 B2 | 8/2021 | Sanchez et al. |
| 11,160,695 B2 | 11/2021 | Febo et al. |
| 11,160,697 B2 | 11/2021 | Maschino et al. |
| 11,168,420 B2 | 11/2021 | Kinugasa et al. |
| 11,179,506 B2 | 11/2021 | Barr et al. |
| 11,199,116 B2 | 12/2021 | Ostromecki et al. |
| 11,207,206 B2 | 12/2021 | Sharma et al. |
| 11,226,376 B2 | 1/2022 | Yamauchi et al. |
| 11,253,389 B2 | 2/2022 | Sharma et al. |
| 11,253,407 B2 | 2/2022 | Miao et al. |
| 11,326,586 B2 | 5/2022 | Milner et al. |
| 11,369,508 B2 | 6/2022 | Ecklund et al. |
| 11,369,524 B2 | 6/2022 | Hubbard et al. |
| 11,376,152 B2 * | 7/2022 | Sanchez ................ A61D 99/00 |
| 11,382,786 B2 * | 7/2022 | Sanchez ................ A61F 5/4404 |
| 11,382,788 B2 | 7/2022 | Hjorth et al. |
| 11,389,318 B2 | 7/2022 | Radl et al. |
| 11,395,871 B2 | 7/2022 | Radl et al. |
| 11,399,990 B2 | 8/2022 | Suyama |
| 11,426,303 B2 * | 8/2022 | Davis .................... A61F 5/4408 |
| 11,504,265 B2 | 11/2022 | Godinez et al. |
| 11,529,252 B2 * | 12/2022 | Glithero ................ A61F 5/455 |
| 11,547,788 B2 | 1/2023 | Radl et al. |
| 11,806,266 B2 * | 11/2023 | Sanchez ................ A61F 5/443 |
| 11,813,189 B2 | 11/2023 | Hussey et al. |
| 11,839,567 B2 * | 12/2023 | Davis .................... A61B 5/208 |
| D1,010,109 S | 1/2024 | Ecklund et al. |
| 11,857,716 B2 | 1/2024 | Lee et al. |
| 11,865,030 B2 | 1/2024 | Davis et al. |
| 11,890,221 B2 | 2/2024 | Ulreich et al. |
| 11,911,160 B2 | 2/2024 | Woodard et al. |
| 11,925,575 B2 | 3/2024 | Newton |
| 11,938,053 B2 | 3/2024 | Austermann et al. |
| 11,944,740 B2 | 4/2024 | Hughett et al. |
| 11,994,122 B2 | 5/2024 | Bodain |
| 11,998,475 B2 | 6/2024 | Becker et al. |
| 12,023,457 B2 | 7/2024 | Mann et al. |
| 12,042,422 B2 * | 7/2024 | Davis .................... A61F 5/451 |
| D1,038,385 S | 8/2024 | Ecklund et al. |
| 12,064,372 B2 | 8/2024 | Godinez et al. |
| 12,070,432 B2 | 8/2024 | Tourchak et al. |
| 12,090,083 B2 | 9/2024 | Ecklund et al. |
| 12,121,468 B2 | 10/2024 | Sanchez et al. |
| 12,133,813 B2 | 11/2024 | Ulreich et al. |
| 12,138,195 B2 * | 11/2024 | Alder .................... A61F 5/453 |
| 12,186,229 B2 | 1/2025 | Davis et al. |
| 12,193,962 B2 | 1/2025 | Newton et al. |
| 12,245,966 B2 | 3/2025 | Newton |
| 12,274,638 B2 | 4/2025 | Spector |
| 12,350,190 B2 | 7/2025 | Hughett, Sr. et al. |
| 2001/0037097 A1 | 11/2001 | Cheng et al. |
| 2001/0037098 A1 | 11/2001 | Snyder |
| 2001/0054426 A1 | 12/2001 | Knudson et al. |
| 2002/0019614 A1 | 2/2002 | Woon |
| 2002/0026161 A1 | 2/2002 | Grundke |
| 2002/0026163 A1 | 2/2002 | Grundke |
| 2002/0042945 A1 | 4/2002 | Sands |
| 2002/0087131 A1 | 7/2002 | Wolff et al. |
| 2002/0091364 A1 | 7/2002 | Prabhakar |
| 2002/0189992 A1 | 12/2002 | Schmidt et al. |
| 2002/0193760 A1 | 12/2002 | Thompson |
| 2002/0193762 A1 | 12/2002 | Suydam |
| 2003/0004436 A1 | 1/2003 | Schmidt et al. |
| 2003/0032931 A1 | 2/2003 | Grundke et al. |
| 2003/0032944 A1 | 2/2003 | Cawood |
| 2003/0073964 A1 | 4/2003 | Palumbo et al. |
| 2003/0074724 A1 | 4/2003 | Sands |
| 2003/0120178 A1 | 6/2003 | Heki |
| 2003/0129178 A1 | 7/2003 | Wegman et al. |
| 2003/0157859 A1 | 8/2003 | Ishikawa |
| 2003/0181880 A1 | 9/2003 | Schwartz |
| 2003/0195484 A1 | 10/2003 | Harvie |
| 2003/0204173 A1 | 10/2003 | Burns et al. |
| 2003/0233079 A1 | 12/2003 | Parks et al. |
| 2004/0006321 A1 | 1/2004 | Cheng et al. |
| 2004/0015141 A1 | 1/2004 | Cheng et al. |
| 2004/0056122 A1 | 3/2004 | Male et al. |
| 2004/0084465 A1 * | 5/2004 | Luburic ............... B65D 43/162 |
| | | 220/276 |
| 2004/0127872 A1 | 7/2004 | Petryk et al. |
| 2004/0128749 A1 | 7/2004 | Scott |
| 2004/0143229 A1 * | 7/2004 | Easter .................... A61F 5/451 |
| | | 604/322 |
| 2004/0147863 A1 | 7/2004 | Diaz et al. |
| 2004/0147894 A1 | 7/2004 | Mizutani et al. |
| 2004/0147895 A1 | 7/2004 | Mizutani et al. |
| 2004/0158221 A1 | 8/2004 | Mizutani et al. |
| 2004/0176731 A1 | 9/2004 | Cheng et al. |
| 2004/0176746 A1 | 9/2004 | Forral |
| 2004/0181201 A1 | 9/2004 | Mizutani et al. |
| 2004/0187200 A1 | 9/2004 | Otto et al. |
| 2004/0191919 A1 | 9/2004 | Unger et al. |
| 2004/0194792 A1 | 10/2004 | Zhuang et al. |
| 2004/0200936 A1 | 10/2004 | Opperthauser |
| 2004/0207530 A1 | 10/2004 | Nielsen |
| 2004/0236292 A1 | 11/2004 | Tazoe et al. |
| 2004/0243075 A1 | 12/2004 | Harvie |
| 2004/0254547 A1 | 12/2004 | Okabe et al. |
| 2005/0010182 A1 * | 1/2005 | Parks .................... A61F 5/4556 |
| | | 604/355 |
| 2005/0010197 A1 | 1/2005 | Lau et al. |
| 2005/0033248 A1 | 2/2005 | Machida et al. |
| 2005/0065471 A1 | 3/2005 | Kuntz |
| 2005/0070861 A1 | 3/2005 | Okabe et al. |
| 2005/0070862 A1 | 3/2005 | Tazoe et al. |
| 2005/0082300 A1 | 4/2005 | Modrell et al. |
| 2005/0097662 A1 | 5/2005 | Leimkuhler et al. |
| 2005/0101924 A1 | 5/2005 | Elson et al. |
| 2005/0119630 A1 | 6/2005 | Harvie |
| 2005/0131361 A1 | 6/2005 | Miskie |
| 2005/0137557 A1 | 6/2005 | Swiecicki et al. |
| 2005/0137560 A1 | 6/2005 | Mizutani et al. |
| 2005/0137561 A1 | 6/2005 | Mizutani et al. |
| 2005/0148984 A1 | 7/2005 | Lindsay et al. |
| 2005/0154360 A1 | 7/2005 | Harvie |
| 2005/0177070 A1 | 8/2005 | Levinson et al. |
| 2005/0197645 A1 | 9/2005 | Karpowicz et al. |
| 2005/0215969 A1 | 9/2005 | Mizutani et al. |
| 2005/0273069 A1 | 12/2005 | Mizutani et al. |
| 2005/0273920 A1 | 12/2005 | Marinas |
| 2005/0277903 A1 | 12/2005 | Mizutani et al. |

(56)          References Cited

U.S. PATENT DOCUMENTS

| | | |
|---|---|---|
| 2005/0277904 A1 | 12/2005 | Chase et al. |
| 2005/0279359 A1 | 12/2005 | LeBlanc et al. |
| 2006/0004332 A1 | 1/2006 | Marx |
| 2006/0005307 A1 | 1/2006 | Arguelles |
| 2006/0015080 A1 | 1/2006 | Mahnensmith |
| 2006/0015081 A1 | 1/2006 | Suzuki et al. |
| 2006/0016778 A1 | 1/2006 | Park |
| 2006/0069359 A1 | 3/2006 | Dipalma et al. |
| 2006/0079854 A1 | 4/2006 | Kay et al. |
| 2006/0100596 A1 | 5/2006 | Miskie |
| 2006/0111648 A1 | 5/2006 | Vermaak |
| 2006/0113334 A1 | 6/2006 | Mikhail et al. |
| 2006/0155214 A1 | 7/2006 | Wightman |
| 2006/0166350 A1 | 7/2006 | Lowe et al. |
| 2006/0171997 A1 | 8/2006 | Gruenbacher et al. |
| 2006/0180566 A1 | 8/2006 | Mataya |
| 2006/0200102 A1 | 9/2006 | Cooper |
| 2006/0229575 A1 | 10/2006 | Boiarski |
| 2006/0229576 A1 | 10/2006 | Conway et al. |
| 2006/0231648 A1 | 10/2006 | Male et al. |
| 2006/0235266 A1 | 10/2006 | Nan |
| 2006/0235359 A1 | 10/2006 | Marland |
| 2006/0241553 A1 | 10/2006 | Harvie |
| 2006/0269439 A1 | 11/2006 | White |
| 2006/0277670 A1 | 12/2006 | Baker et al. |
| 2007/0006368 A1 | 1/2007 | Key et al. |
| 2007/0010797 A1 | 1/2007 | Nishtala et al. |
| 2007/0016152 A1 | 1/2007 | Karpowicz et al. |
| 2007/0025886 A1 | 2/2007 | Yong |
| 2007/0038194 A1 | 2/2007 | Wada et al. |
| 2007/0055209 A1 | 3/2007 | Patel et al. |
| 2007/0073252 A1 | 3/2007 | Forgrave |
| 2007/0117880 A1 | 5/2007 | Elson et al. |
| 2007/0118993 A1 | 5/2007 | Bates |
| 2007/0135786 A1 | 6/2007 | Schmidt et al. |
| 2007/0137718 A1 | 6/2007 | Rushlander et al. |
| 2007/0149935 A1 | 6/2007 | Dirico |
| 2007/0191804 A1 | 8/2007 | Coley |
| 2007/0203464 A1 | 8/2007 | Green et al. |
| 2007/0214553 A1 | 9/2007 | Carromba et al. |
| 2007/0225663 A1 | 9/2007 | Watt et al. |
| 2007/0225666 A1 | 9/2007 | Otto |
| 2007/0225668 A1 | 9/2007 | Otto |
| 2007/0266486 A1 | 11/2007 | Ramirez |
| 2007/0270716 A1 | 11/2007 | Wu et al. |
| 2007/0282309 A1 | 12/2007 | Bengtson et al. |
| 2008/0004576 A1 | 1/2008 | Tanaka et al. |
| 2008/0015526 A1 | 1/2008 | Reiner et al. |
| 2008/0015527 A1 | 1/2008 | House |
| 2008/0033386 A1 | 2/2008 | Okabe et al. |
| 2008/0041869 A1 | 2/2008 | Backaert |
| 2008/0077099 A1 | 3/2008 | House |
| 2008/0091153 A1 | 4/2008 | Harvie |
| 2008/0091158 A1 | 4/2008 | Yang |
| 2008/0114327 A1 | 5/2008 | Barge |
| 2008/0140033 A1 | 6/2008 | Burgess et al. |
| 2008/0167634 A1 | 7/2008 | Kouta et al. |
| 2008/0183157 A1 | 7/2008 | Walters |
| 2008/0215031 A1 | 9/2008 | Belfort et al. |
| 2008/0234642 A1 | 9/2008 | Patterson et al. |
| 2008/0269703 A1 | 10/2008 | Collins et al. |
| 2008/0281282 A1 | 11/2008 | Finger et al. |
| 2008/0287894 A1 | 11/2008 | Van Den Heuvel et al. |
| 2008/0312550 A1* | 12/2008 | Nishtala .................. A61B 5/20 |
| | | 600/549 |
| 2009/0025717 A1 | 1/2009 | Pinel |
| 2009/0048570 A1 | 2/2009 | Jensen |
| 2009/0056003 A1 | 3/2009 | Ivie et al. |
| 2009/0069761 A1 | 3/2009 | Vogel |
| 2009/0069765 A1 | 3/2009 | Wortham |
| 2009/0120179 A1 | 5/2009 | Nylander et al. |
| 2009/0192482 A1 | 7/2009 | Dodge et al. |
| 2009/0226541 A1 | 9/2009 | Scholz et al. |
| 2009/0234312 A1 | 9/2009 | Otoole et al. |
| 2009/0251510 A1 | 10/2009 | Noro et al. |
| 2009/0254040 A1 | 10/2009 | Bierman et al. |
| 2009/0259206 A1 | 10/2009 | Kai et al. |
| 2009/0264840 A1 | 10/2009 | Virginio |
| 2009/0270822 A1 | 10/2009 | Medeiros |
| 2009/0281510 A1 | 11/2009 | Fisher |
| 2009/0283982 A1 | 11/2009 | Thomas |
| 2009/0306610 A1 | 12/2009 | Van Den Heuvel et al. |
| 2010/0004612 A1 | 1/2010 | Thevenin |
| 2010/0030189 A1 | 2/2010 | Fleming |
| 2010/0031429 A1 | 2/2010 | Kim et al. |
| 2010/0032789 A1 | 2/2010 | Schoen et al. |
| 2010/0058660 A1 | 3/2010 | Williams |
| 2010/0121289 A1 | 5/2010 | Parks et al. |
| 2010/0160882 A1 | 6/2010 | Lowe |
| 2010/0174250 A1 | 7/2010 | Hu et al. |
| 2010/0179493 A1 | 7/2010 | Heagle et al. |
| 2010/0185168 A1 | 7/2010 | Graauw et al. |
| 2010/0198172 A1 | 8/2010 | Wada et al. |
| 2010/0211032 A1 | 8/2010 | Tsai et al. |
| 2010/0234820 A1 | 9/2010 | Tsai et al. |
| 2010/0241104 A1 | 9/2010 | Gilbert |
| 2010/0263113 A1 | 10/2010 | Shelton et al. |
| 2010/0310845 A1 | 12/2010 | Bond et al. |
| 2011/0028920 A1 | 2/2011 | Johannison |
| 2011/0028922 A1 | 2/2011 | Kay et al. |
| 2011/0034889 A1 | 2/2011 | Smith |
| 2011/0036837 A1 | 2/2011 | Shang |
| 2011/0040267 A1 | 2/2011 | Wada et al. |
| 2011/0040271 A1 | 2/2011 | Rogers et al. |
| 2011/0054426 A1 | 3/2011 | Stewart et al. |
| 2011/0060299 A1 | 3/2011 | Wada et al. |
| 2011/0060300 A1 | 3/2011 | Weig et al. |
| 2011/0077495 A1 | 3/2011 | Gilbert |
| 2011/0077606 A1 | 3/2011 | Wilcox et al. |
| 2011/0087337 A1 | 4/2011 | Forsell |
| 2011/0145993 A1 | 6/2011 | Rader et al. |
| 2011/0152802 A1 | 6/2011 | Dicamillo et al. |
| 2011/0164147 A1 | 7/2011 | Takahashi et al. |
| 2011/0172620 A1 | 7/2011 | Khambatta |
| 2011/0172625 A1 | 7/2011 | Wada et al. |
| 2011/0198904 A1 | 8/2011 | Thomas et al. |
| 2011/0202024 A1 | 8/2011 | Cozzens |
| 2011/0238023 A1 | 9/2011 | Slayton |
| 2011/0240648 A1 | 10/2011 | Tucker |
| 2011/0251572 A1 | 10/2011 | Nishtala et al. |
| 2011/0265889 A1 | 11/2011 | Tanaka et al. |
| 2011/0276020 A1 | 11/2011 | Mitsui |
| 2012/0029452 A1 | 2/2012 | Roedsten |
| 2012/0035577 A1 | 2/2012 | Tomes et al. |
| 2012/0041400 A1 | 2/2012 | Christensen |
| 2012/0059328 A1 | 3/2012 | Dikeman et al. |
| 2012/0066825 A1 | 3/2012 | Birbara et al. |
| 2012/0103347 A1 | 5/2012 | Wheaton et al. |
| 2012/0116336 A1* | 5/2012 | Sharma ................ A61M 25/04 |
| | | 604/328 |
| 2012/0137420 A1 | 6/2012 | Gordon et al. |
| 2012/0165768 A1 | 6/2012 | Sekiyama et al. |
| 2012/0209216 A1 | 8/2012 | Jensen et al. |
| 2012/0209225 A1 | 8/2012 | Hu et al. |
| 2012/0210503 A1 | 8/2012 | Anzivino et al. |
| 2012/0233761 A1 | 9/2012 | Huang |
| 2012/0245541 A1 | 9/2012 | Suzuki et al. |
| 2012/0245542 A1 | 9/2012 | Suzuki et al. |
| 2012/0245547 A1 | 9/2012 | Wilcox et al. |
| 2012/0253303 A1 | 10/2012 | Suzuki et al. |
| 2012/0271259 A1 | 10/2012 | Ulert |
| 2012/0296305 A1 | 11/2012 | Barraza Khaled et al. |
| 2012/0316522 A1 | 12/2012 | Carter et al. |
| 2012/0330256 A1 | 12/2012 | Wilcox et al. |
| 2013/0006206 A1 | 1/2013 | Wada et al. |
| 2013/0019374 A1* | 1/2013 | Schwartz .......... A61F 13/01008 |
| | | 428/492 |
| 2013/0036544 A1 | 2/2013 | Lee et al. |
| 2013/0045651 A1 | 2/2013 | Esteves et al. |
| 2013/0046258 A1 | 2/2013 | Chambers |
| 2013/0053804 A1 | 2/2013 | Soerensen et al. |
| 2013/0096523 A1 | 4/2013 | Chang et al. |
| 2013/0110059 A1 | 5/2013 | Kossow et al. |
| 2013/0138064 A1 | 5/2013 | Stroebech et al. |

(56) References Cited

U.S. PATENT DOCUMENTS

| | | |
|---|---|---|
| 2013/0144240 A1 | 6/2013 | Ellis |
| 2013/0150813 A1 | 6/2013 | Gordon et al. |
| 2013/0158494 A1 | 6/2013 | Ong et al. |
| 2013/0165880 A1 | 6/2013 | Amos et al. |
| 2013/0218112 A1 | 8/2013 | Thompson |
| 2013/0245496 A1 | 9/2013 | Wells et al. |
| 2013/0245586 A1 | 9/2013 | Jha |
| 2013/0274711 A1 | 10/2013 | O'Day |
| 2013/0292537 A1 | 11/2013 | Dirico |
| 2013/0330501 A1 | 12/2013 | Aizenberg et al. |
| 2014/0005647 A1 | 1/2014 | Shuffler et al. |
| 2014/0031774 A1 | 1/2014 | Bengtson |
| 2014/0039432 A1 | 2/2014 | Dunbar et al. |
| 2014/0039440 A1 | 2/2014 | Doescher |
| 2014/0058347 A1 | 2/2014 | Marquette |
| 2014/0107599 A1 | 4/2014 | Fink et al. |
| 2014/0157499 A1 | 6/2014 | Suzuki et al. |
| 2014/0171889 A1 | 6/2014 | Hopman et al. |
| 2014/0182051 A1 | 7/2014 | Tanimoto et al. |
| 2014/0196189 A1 | 7/2014 | Lee et al. |
| 2014/0257231 A1 | 9/2014 | Wang et al. |
| 2014/0303582 A1 | 10/2014 | Wright et al. |
| 2014/0316381 A1 | 10/2014 | Reglin |
| 2014/0325746 A1 | 11/2014 | Block |
| 2014/0348139 A1 | 11/2014 | Gomez Martinez |
| 2014/0352050 A1 | 12/2014 | Yao et al. |
| 2014/0371628 A1 | 12/2014 | Desai |
| 2015/0045757 A1 | 2/2015 | Lee et al. |
| 2015/0047114 A1 | 2/2015 | Ramirez |
| 2015/0048089 A1 | 2/2015 | Robertson |
| 2015/0135423 A1 | 5/2015 | Sharpe et al. |
| 2015/0157300 A1 | 6/2015 | Ealovega et al. |
| 2015/0209188 A1 | 7/2015 | Scheremet et al. |
| 2015/0209194 A1 | 7/2015 | Heyman |
| 2015/0267862 A1 | 9/2015 | Mishler |
| 2015/0290421 A1 | 10/2015 | Glickman et al. |
| 2015/0290425 A1 | 10/2015 | Macy et al. |
| 2015/0320583 A1 | 11/2015 | Harvie |
| 2015/0329255 A1 | 11/2015 | Rzepecki |
| 2015/0342799 A1 | 12/2015 | Michiels et al. |
| 2015/0359660 A1 | 12/2015 | Harvie |
| 2015/0359996 A1 | 12/2015 | Arora et al. |
| 2015/0366699 A1 | 12/2015 | Nelson |
| 2016/0008193 A1 | 1/2016 | Schulke |
| 2016/0029998 A1 | 2/2016 | Brister et al. |
| 2016/0030228 A1 | 2/2016 | Jones |
| 2016/0038356 A1 | 2/2016 | Yao et al. |
| 2016/0051395 A1 | 2/2016 | Ugarte M.D. |
| 2016/0058322 A1 | 3/2016 | Brister et al. |
| 2016/0060001 A1 | 3/2016 | Wada et al. |
| 2016/0100976 A1 | 4/2016 | Conway et al. |
| 2016/0106604 A1 | 4/2016 | Timm |
| 2016/0113809 A1 | 4/2016 | Kim |
| 2016/0135792 A1 | 5/2016 | Cai |
| 2016/0136338 A1 | 5/2016 | Lee et al. |
| 2016/0183689 A1 | 6/2016 | Miner |
| 2016/0256022 A1 | 9/2016 | Le |
| 2016/0270982 A1 | 9/2016 | Raycheck et al. |
| 2016/0278662 A1 | 9/2016 | Brister et al. |
| 2016/0327553 A1 | 11/2016 | Edwards et al. |
| 2016/0357400 A1 | 12/2016 | Penha et al. |
| 2016/0366699 A1 | 12/2016 | Zhang et al. |
| 2016/0367226 A1 | 12/2016 | Newton et al. |
| 2016/0367411 A1 | 12/2016 | Justiz et al. |
| 2016/0374848 A1* | 12/2016 | Sanchez .................. A61F 5/455 604/319 |
| 2017/0007438 A1 | 1/2017 | Harvie |
| 2017/0014560 A1 | 1/2017 | Minskoff et al. |
| 2017/0042724 A1 | 2/2017 | Ugarte |
| 2017/0042748 A1 | 2/2017 | Griffin |
| 2017/0100276 A1 | 4/2017 | Joh |
| 2017/0107312 A1 | 4/2017 | Hinayama et al. |
| 2017/0128638 A1 | 5/2017 | Giezendanner et al. |
| 2017/0136209 A1 | 5/2017 | Burnett et al. |
| 2017/0143534 A1 | 5/2017 | Sanchez |
| 2017/0165100 A1 | 6/2017 | Jackson et al. |
| 2017/0165405 A1 | 6/2017 | Muser et al. |
| 2017/0189225 A1 | 7/2017 | Voorhees et al. |
| 2017/0202692 A1 | 7/2017 | Laniado |
| 2017/0216081 A1 | 8/2017 | Accosta |
| 2017/0238911 A1 | 8/2017 | Duval |
| 2017/0246026 A1 | 8/2017 | Laniado |
| 2017/0252014 A1 | 9/2017 | Siller Gonzalez et al. |
| 2017/0252202 A9 | 9/2017 | Sanchez et al. |
| 2017/0266031 A1 | 9/2017 | Sanchez et al. |
| 2017/0266658 A1 | 9/2017 | Bruno et al. |
| 2017/0281399 A1 | 10/2017 | Vanmiddendorp et al. |
| 2017/0281419 A1 | 10/2017 | Pintado |
| 2017/0312116 A1 | 11/2017 | Laniado |
| 2017/0325788 A1 | 11/2017 | Ealovega et al. |
| 2017/0333244 A1 | 11/2017 | Laniado |
| 2017/0348139 A1 | 12/2017 | Newton et al. |
| 2017/0354532 A1 | 12/2017 | Holt |
| 2017/0354551 A1 | 12/2017 | Gawley et al. |
| 2017/0367873 A1 | 12/2017 | Grannum |
| 2018/0002075 A1 | 1/2018 | Lee |
| 2018/0008451 A1 | 1/2018 | Stroebech |
| 2018/0008804 A1 | 1/2018 | Laniado |
| 2018/0021218 A1 | 1/2018 | Brosch et al. |
| 2018/0028349 A1 | 2/2018 | Newton et al. |
| 2018/0037384 A1 | 2/2018 | Archeny et al. |
| 2018/0049910 A1 | 2/2018 | Newton |
| 2018/0064572 A1 | 3/2018 | Wiltshire |
| 2018/0104131 A1 | 4/2018 | Killian |
| 2018/0127187 A1 | 5/2018 | Sewell |
| 2018/0149635 A1 | 5/2018 | Abir |
| 2018/0193215 A1 | 7/2018 | Davies et al. |
| 2018/0200101 A1 | 7/2018 | Su |
| 2018/0214297 A1 | 8/2018 | Hughett et al. |
| 2018/0221216 A1 | 8/2018 | Benz et al. |
| 2018/0228642 A1* | 8/2018 | Davis .................... A61B 5/208 |
| 2018/0229014 A1 | 8/2018 | Guirguis et al. |
| 2018/0256384 A1 | 9/2018 | Kasirye |
| 2018/0271694 A1 | 9/2018 | Fernandez et al. |
| 2018/0280236 A1 | 10/2018 | Ludin et al. |
| 2018/0317892 A1 | 11/2018 | Catlin |
| 2018/0325748 A1 | 11/2018 | Sharma et al. |
| 2019/0001029 A1 | 1/2019 | Davie et al. |
| 2019/0001030 A1 | 1/2019 | Braga et al. |
| 2019/0021899 A1 | 1/2019 | Vlet |
| 2019/0038451 A1 | 2/2019 | Harvie |
| 2019/0046102 A1 | 2/2019 | Kushnir et al. |
| 2019/0059938 A1 | 2/2019 | Holsten |
| 2019/0091059 A1 | 3/2019 | Gabriel |
| 2019/0100362 A1 | 4/2019 | Meyers et al. |
| 2019/0133126 A1 | 5/2019 | Modak et al. |
| 2019/0133814 A1 | 5/2019 | Tammen et al. |
| 2019/0142624 A1 | 5/2019 | Sanchez et al. |
| 2019/0224036 A1 | 7/2019 | Sanchez et al. |
| 2019/0226189 A1 | 7/2019 | Braxton |
| 2019/0240079 A1 | 8/2019 | Tuli |
| 2019/0247222 A1 | 8/2019 | Ecklund et al. |
| 2019/0247223 A1 | 8/2019 | Brun et al. |
| 2019/0247623 A1 | 8/2019 | Helm et al. |
| 2019/0282391 A1 | 9/2019 | Johannes et al. |
| 2019/0314189 A1 | 10/2019 | Acosta |
| 2019/0314190 A1 | 10/2019 | Sanchez et al. |
| 2019/0321587 A1 | 10/2019 | Mcmenamin et al. |
| 2019/0344934 A1 | 11/2019 | Faerber et al. |
| 2019/0365303 A1 | 12/2019 | Bullington et al. |
| 2019/0365307 A1 | 12/2019 | Laing et al. |
| 2019/0365561 A1 | 12/2019 | Newton et al. |
| 2019/0374373 A1 | 12/2019 | Joh |
| 2020/0008985 A1 | 1/2020 | Nguyen et al. |
| 2020/0016012 A1 | 1/2020 | Dutkiewicz |
| 2020/0030595 A1 | 1/2020 | Boukidjian et al. |
| 2020/0040561 A1 | 2/2020 | Sugawara |
| 2020/0046544 A1 | 2/2020 | Godinez et al. |
| 2020/0055638 A1 | 2/2020 | Lau et al. |
| 2020/0070392 A1 | 3/2020 | Huber et al. |
| 2020/0085609 A1 | 3/2020 | Schelch et al. |
| 2020/0085610 A1 | 3/2020 | Cohn et al. |
| 2020/0086090 A1 | 3/2020 | Von Weymarn-schärli et al. |
| 2020/0107518 A1 | 4/2020 | Hiroshima et al. |

(56) References Cited

U.S. PATENT DOCUMENTS

| | | |
|---|---|---|
| 2020/0129322 A1 | 4/2020 | Leuckel |
| 2020/0171217 A9 | 6/2020 | Braga et al. |
| 2020/0179177 A1 | 6/2020 | Erdem et al. |
| 2020/0187918 A1 | 6/2020 | Wiygul |
| 2020/0206015 A1 | 7/2020 | Langer |
| 2020/0206039 A1 | 7/2020 | Mclain |
| 2020/0214910 A1 | 7/2020 | Varona et al. |
| 2020/0216898 A1 | 7/2020 | Hubbell |
| 2020/0216989 A1 | 7/2020 | Kinugasa et al. |
| 2020/0229964 A1 | 7/2020 | Staali et al. |
| 2020/0231343 A1 | 7/2020 | Freedman et al. |
| 2020/0232841 A1 | 7/2020 | Satish et al. |
| 2020/0246172 A1 | 8/2020 | Ho |
| 2020/0246203 A1 | 8/2020 | Tulk et al. |
| 2020/0255189 A1 | 8/2020 | Liu |
| 2020/0261280 A1 | 8/2020 | Heyman |
| 2020/0276046 A1 | 9/2020 | Staali et al. |
| 2020/0306075 A1 | 10/2020 | Newton et al. |
| 2020/0315837 A1 | 10/2020 | Radl et al. |
| 2020/0315838 A1 | 10/2020 | Eckert |
| 2020/0315872 A1 | 10/2020 | Viens et al. |
| 2020/0315874 A1 | 10/2020 | Viens et al. |
| 2020/0331672 A1 | 10/2020 | Bertram et al. |
| 2020/0345332 A1 | 11/2020 | Duval |
| 2020/0353135 A1 | 11/2020 | Gregory et al. |
| 2020/0367677 A1 | 11/2020 | Silsby et al. |
| 2020/0369444 A1 | 11/2020 | Silsby et al. |
| 2020/0375781 A1 | 12/2020 | Staali et al. |
| 2020/0375810 A1 | 12/2020 | Carlin et al. |
| 2020/0384242 A1 | 12/2020 | Havard et al. |
| 2020/0385179 A1 | 12/2020 | Mccourt |
| 2020/0390591 A1 | 12/2020 | Glithero et al. |
| 2020/0390592 A1 | 12/2020 | Merrill |
| 2020/0398024 A1 | 12/2020 | Fletter et al. |
| 2020/0405521 A1 | 12/2020 | Glasroe |
| 2021/0008771 A1 | 1/2021 | Huber et al. |
| 2021/0009323 A1 | 1/2021 | Markarian et al. |
| 2021/0020072 A1 | 1/2021 | Moehring et al. |
| 2021/0023279 A1 | 1/2021 | Radl et al. |
| 2021/0059853 A1* | 3/2021 | Davis .................... A61B 5/208 |
| 2021/0061523 A1 | 3/2021 | Bytheway |
| 2021/0069005 A1 | 3/2021 | Sanchez et al. |
| 2021/0069008 A1 | 3/2021 | Blabas et al. |
| 2021/0069009 A1 | 3/2021 | Im |
| 2021/0069030 A1 | 3/2021 | Nishikawa et al. |
| 2021/0077993 A1 | 3/2021 | Nazareth et al. |
| 2021/0113749 A1 | 4/2021 | Radl et al. |
| 2021/0121318 A1 | 4/2021 | Pinlac |
| 2021/0137724 A1 | 5/2021 | Ecklund et al. |
| 2021/0138190 A1 | 5/2021 | Erbey et al. |
| 2021/0154055 A1 | 5/2021 | Villarreal |
| 2021/0170079 A1 | 6/2021 | Radl et al. |
| 2021/0178390 A1 | 6/2021 | Oueslati et al. |
| 2021/0186742 A1 | 6/2021 | Newton et al. |
| 2021/0186744 A1 | 6/2021 | Spector |
| 2021/0211568 A1 | 7/2021 | Zhou et al. |
| 2021/0212865 A1 | 7/2021 | Wallajapet et al. |
| 2021/0220162 A1 | 7/2021 | Jamison |
| 2021/0220163 A1 | 7/2021 | Mayrand |
| 2021/0228400 A1 | 7/2021 | Glithero |
| 2021/0228401 A1 | 7/2021 | Becker et al. |
| 2021/0228795 A1 | 7/2021 | Hughett et al. |
| 2021/0229877 A1 | 7/2021 | Ragias et al. |
| 2021/0236323 A1 | 8/2021 | Austermann et al. |
| 2021/0236324 A1 | 8/2021 | Sweeney |
| 2021/0251814 A1 | 8/2021 | Jönegren et al. |
| 2021/0267787 A1 | 9/2021 | Nazemi |
| 2021/0275343 A1 | 9/2021 | Sanchez et al. |
| 2021/0275344 A1 | 9/2021 | Wing |
| 2021/0290454 A1 | 9/2021 | Yamada |
| 2021/0290464 A1 | 9/2021 | Furuta |
| 2021/0315726 A1 | 10/2021 | Lin |
| 2021/0315727 A1 | 10/2021 | Jiang |
| 2021/0353449 A1 | 11/2021 | Sharma et al. |
| 2021/0353450 A1 | 11/2021 | Sharma et al. |
| 2021/0361469 A1 | 11/2021 | Liu et al. |
| 2021/0369495 A1 | 12/2021 | Cheng et al. |
| 2021/0386925 A1 | 12/2021 | Hartwell et al. |
| 2021/0393433 A1 | 12/2021 | Godinez et al. |
| 2022/0023091 A1 | 1/2022 | Ecklund et al. |
| 2022/0026546 A1 | 1/2022 | Aono et al. |
| 2022/0031290 A1 | 2/2022 | Weed |
| 2022/0031523 A1 | 2/2022 | Pierpoint |
| 2022/0039995 A1 | 2/2022 | Johannes et al. |
| 2022/0047410 A1 | 2/2022 | Walthall |
| 2022/0062025 A1 | 3/2022 | Shields et al. |
| 2022/0062027 A1 | 3/2022 | Mitchell et al. |
| 2022/0062028 A1 | 3/2022 | Mitchell et al. |
| 2022/0062029 A1* | 3/2022 | Johannes ............... A61F 5/4401 |
| 2022/0066825 A1 | 3/2022 | Saraf et al. |
| 2022/0071811 A1 | 3/2022 | Cheng et al. |
| 2022/0071826 A1 | 3/2022 | Kulkarni et al. |
| 2022/0104965 A1 | 4/2022 | Vaninetti et al. |
| 2022/0104976 A1 | 4/2022 | Hoeger et al. |
| 2022/0104981 A1 | 4/2022 | Jones |
| 2022/0117773 A1 | 4/2022 | Davis et al. |
| 2022/0117774 A1* | 4/2022 | Meyer ..................... A61F 5/455 |
| 2022/0117775 A1* | 4/2022 | Jones .................. A61L 26/0009 |
| 2022/0118165 A1 | 4/2022 | Knapp et al. |
| 2022/0133524 A1 | 5/2022 | Davis |
| 2022/0151817 A1* | 5/2022 | Mann ..................... A61F 5/451 |
| 2022/0160949 A1 | 5/2022 | Simiele et al. |
| 2022/0168159 A1 | 6/2022 | Triado et al. |
| 2022/0193312 A1 | 6/2022 | Lee et al. |
| 2022/0211536 A1 | 7/2022 | Johannes et al. |
| 2022/0218510 A1 | 7/2022 | Metzger et al. |
| 2022/0229053 A1 | 7/2022 | Levin et al. |
| 2022/0241106 A1 | 8/2022 | Johannes et al. |
| 2022/0247407 A1 | 8/2022 | Yamamoto et al. |
| 2022/0248836 A1 | 8/2022 | Cagle et al. |
| 2022/0257407 A1 | 8/2022 | Johannes et al. |
| 2022/0265460 A1 | 8/2022 | Coker |
| 2022/0265462 A1* | 8/2022 | Alder .................... A61F 5/4404 |
| 2022/0270114 A1 | 8/2022 | Feala et al. |
| 2022/0273482 A1 | 9/2022 | Johannes et al. |
| 2022/0280357 A1 | 9/2022 | Jagannathan et al. |
| 2022/0280710 A1 | 9/2022 | Agrawal et al. |
| 2022/0287689 A1 | 9/2022 | Johannes |
| 2022/0287867 A1 | 9/2022 | Jones et al. |
| 2022/0287868 A1 | 9/2022 | Garvey et al. |
| 2022/0296408 A1 | 9/2022 | Evans et al. |
| 2022/0305191 A1 | 9/2022 | Joseph et al. |
| 2022/0313222 A1* | 10/2022 | Austermann ........ A61B 10/007 |
| 2022/0313474 A1 | 10/2022 | Kriscovich et al. |
| 2022/0331170 A1 | 10/2022 | Erdem et al. |
| 2022/0339023 A1 | 10/2022 | Davis et al. |
| 2022/0339024 A1 | 10/2022 | Johannes et al. |
| 2022/0354685 A1* | 11/2022 | Davis .................... A61B 5/208 |
| 2022/0362049 A1 | 11/2022 | Austermann et al. |
| 2022/0370231 A1 | 11/2022 | Wang et al. |
| 2022/0370234 A1 | 11/2022 | Hughett et al. |
| 2022/0370235 A1 | 11/2022 | Johannes et al. |
| 2022/0370237 A1 | 11/2022 | Parmar et al. |
| 2022/0387001 A1 | 12/2022 | Askenazi et al. |
| 2022/0387693 A1 | 12/2022 | Bannwart et al. |
| 2022/0395390 A1 | 12/2022 | Brooks |
| 2022/0395391 A1* | 12/2022 | Saunders .............. A61F 5/4404 |
| 2022/0401252 A1 | 12/2022 | Warren |
| 2022/0409419 A1 | 12/2022 | Garvey et al. |
| 2022/0409422 A1 | 12/2022 | Schneider et al. |
| 2023/0018845 A1* | 1/2023 | Lee ........................... A61F 5/44 |
| 2023/0020563 A1 | 1/2023 | Sharma et al. |
| 2023/0031640 A1 | 2/2023 | Hughett et al. |
| 2023/0037159 A1* | 2/2023 | Brennan ............... A61F 5/4405 |
| 2023/0049924 A1 | 2/2023 | Johannes et al. |
| 2023/0052238 A1 | 2/2023 | Oluwasogo |
| 2023/0062994 A1 | 3/2023 | Ecklund et al. |
| 2023/0070347 A1 | 3/2023 | Watson et al. |
| 2023/0073708 A1 | 3/2023 | Xu et al. |
| 2023/0089032 A1* | 3/2023 | Hughett ............... A61F 5/4401 |
| | | 604/319 |
| 2023/0091118 A1 | 3/2023 | Watson |
| 2023/0099821 A1 | 3/2023 | Radl et al. |
| 2023/0099991 A1 | 3/2023 | Bianchi et al. |

(56) References Cited

U.S. PATENT DOCUMENTS

| | | | |
|---|---|---|---|
| 2023/0105001 A1* | 4/2023 | Whittome | A61F 5/455 |
| | | | 604/319 |
| 2023/0110577 A1 | 4/2023 | Choi | |
| 2023/0138269 A1* | 5/2023 | Abdelal | A61F 5/451 |
| | | | 604/347 |
| 2023/0145365 A1 | 5/2023 | Martin et al. | |
| 2023/0155253 A1 | 5/2023 | Yin et al. | |
| 2023/0190511 A1 | 6/2023 | Sharma et al. | |
| 2023/0210504 A1 | 7/2023 | Kuroda et al. | |
| 2023/0210685 A1 | 7/2023 | Fallows et al. | |
| 2023/0218426 A1 | 7/2023 | Hughett | |
| 2023/0240884 A1 | 8/2023 | Davis et al. | |
| 2023/0248562 A1 | 8/2023 | Sanchez et al. | |
| 2023/0248564 A1 | 8/2023 | Mann et al. | |
| 2023/0255812 A1 | 8/2023 | Sanchez et al. | |
| 2023/0255813 A1 | 8/2023 | Sanchez et al. | |
| 2023/0255815 A1 | 8/2023 | Newton | |
| 2023/0263650 A1 | 8/2023 | Sanchez et al. | |
| 2023/0263655 A1 | 8/2023 | Johannes et al. | |
| 2023/0277360 A1 | 9/2023 | Lambert et al. | |
| 2023/0277362 A1 | 9/2023 | Davis et al. | |
| 2023/0285178 A1 | 9/2023 | Sanchez et al. | |
| 2023/0293339 A1 | 9/2023 | James | |
| 2023/0301846 A1 | 9/2023 | Greenwood | |
| 2023/0355423 A1 | 11/2023 | Stevenson et al. | |
| 2023/0389900 A1 | 12/2023 | Xie et al. | |
| 2023/0404791 A1 | 12/2023 | Ecklund et al. | |
| 2024/0008444 A1 | 1/2024 | Su et al. | |
| 2024/0009023 A1* | 1/2024 | Johannes | A61F 5/442 |
| 2024/0024170 A1 | 1/2024 | Scott | |
| 2024/0033148 A1 | 2/2024 | Gordon et al. | |
| 2024/0041638 A1 | 2/2024 | Johannes et al. | |
| 2024/0058157 A1 | 2/2024 | Davis | |
| 2024/0058160 A1 | 2/2024 | Young Joyner et al. | |
| 2024/0058161 A1 | 2/2024 | Ulreich et al. | |
| 2024/0058520 A1 | 2/2024 | Yin et al. | |
| 2024/0065881 A1 | 2/2024 | Kuroda et al. | |
| 2024/0082044 A1 | 3/2024 | Nguyen et al. | |
| 2024/0099874 A1 | 3/2024 | Sanchez et al. | |
| 2024/0108268 A1 | 4/2024 | Woodard et al. | |
| 2024/0110318 A1 | 4/2024 | Bendt et al. | |
| 2024/0122773 A1 | 4/2024 | Nguyen et al. | |
| 2024/0123134 A1 | 4/2024 | Kharkar et al. | |
| 2024/0130885 A1 | 4/2024 | Young Joyner et al. | |
| 2024/0148539 A1* | 5/2024 | Austermann | A61F 5/451 |
| 2024/0156633 A1 | 5/2024 | Fallows et al. | |
| 2024/0164935 A1 | 5/2024 | Newton | |
| 2024/0252343 A1 | 8/2024 | Voda | |
| 2024/0261131 A1 | 8/2024 | Garvey et al. | |
| 2024/0268986 A1 | 8/2024 | Barnes et al. | |
| 2024/0268989 A1 | 8/2024 | Martin et al. | |
| 2024/0268991 A1 | 8/2024 | Davis | |
| 2024/0269027 A1 | 8/2024 | Tourchak et al. | |
| 2024/0285425 A1 | 8/2024 | Donohoe et al. | |
| 2024/0325190 A1 | 10/2024 | Minchew et al. | |
| 2024/0341998 A1* | 10/2024 | Julian | A61F 5/451 |
| 2024/0358539 A1 | 10/2024 | Gallup | |
| 2024/0358542 A1 | 10/2024 | Richardson et al. | |
| 2024/0374414 A1 | 11/2024 | Richardson et al. | |
| 2025/0009552 A1 | 1/2025 | Blabas et al. | |
| 2025/0073055 A1 | 3/2025 | Ecklund et al. | |
| 2025/0107920 A1 | 4/2025 | Fallows et al. | |
| 2025/0107921 A1 | 4/2025 | Sanchez et al. | |

FOREIGN PATENT DOCUMENTS

| | | | |
|---|---|---|---|
| AU | 2022349367 A1 | 4/2024 | |
| CA | 2165286 C | 9/1999 | |
| CA | 2335223 A1 | 1/2000 | |
| CA | 2354132 A1 | 6/2000 | |
| CA | 2359091 C | 9/2003 | |
| CA | 2488867 C | 8/2007 | |
| CA | 3031934 A1 | 2/2018 | |
| CA | 3050918 A1 | 8/2018 | |

| | | | |
|---|---|---|---|
| CA | 3098571 A1 | 11/2019 | |
| CA | 3144181 A1 | 1/2021 | |
| CA | 3188651 A1 | 7/2023 | |
| CN | 2269203 Y | 12/1997 | |
| CN | 1332620 A | 1/2002 | |
| CN | 1434693 A | 8/2003 | |
| CN | 1533755 A | 10/2004 | |
| CN | 1579348 A | 2/2005 | |
| CN | 1602825 A | 4/2005 | |
| CN | 1638708 A | 7/2005 | |
| CN | 1720888 A | 1/2006 | |
| CN | 2936204 Y | 8/2007 | |
| CN | 101262836 A | 9/2008 | |
| CN | 101522148 A | 9/2009 | |
| CN | 102159159 A | 8/2011 | |
| CN | 202184840 U | 4/2012 | |
| CN | 102481441 A | 5/2012 | |
| CN | 202463712 U | 10/2012 | |
| CN | 202950810 U | 5/2013 | |
| CN | 103553968 A | 1/2014 | |
| CN | 103717180 A | 4/2014 | |
| CN | 204562697 U | 8/2015 | |
| CN | 105411783 A | 3/2016 | |
| CN | 105451693 A | 3/2016 | |
| CN | 105534632 A | 5/2016 | |
| CN | 106132360 A | 11/2016 | |
| CN | 205849719 U | 1/2017 | |
| CN | 205924282 U | 2/2017 | |
| CN | 106726089 A | 5/2017 | |
| CN | 107847384 A | 3/2018 | |
| CN | 107920912 A | 4/2018 | |
| CN | 108420590 A | 8/2018 | |
| CN | 209285902 U | 8/2019 | |
| CN | 110381883 A | 10/2019 | |
| CN | 211198839 U | 8/2020 | |
| CN | 111991136 A | 11/2020 | |
| CN | 112022488 A | 12/2020 | |
| CN | 212234893 U | 12/2020 | |
| CN | 212466312 U | 2/2021 | |
| CN | 112566550 A | 3/2021 | |
| CN | 112603184 A | 4/2021 | |
| CN | 213490035 U | 6/2021 | |
| CN | 114007493 A | 2/2022 | |
| CN | 114375187 A | 4/2022 | |
| CN | 116096332 A | 5/2023 | |
| DE | 1516466 A1 | 6/1969 | |
| DE | 2721330 A1 | 11/1977 | |
| DE | 2742298 A1 | 3/1978 | |
| DE | 9407554.9 U1 | 5/1995 | |
| DE | 4443710 A1 | 6/1995 | |
| DE | 4416094 A1 | 11/1995 | |
| DE | 4236097 C2 | 10/1996 | |
| DE | 19619597 A1 | 11/1997 | |
| DE | 102005037762 B3 | 9/2006 | |
| DE | 102011103783 A1 | 12/2012 | |
| DE | 102012112818 A1 | 6/2014 | |
| DE | 202015104597 U1 | 7/2016 | |
| DE | 102018118570 A1 | 2/2020 | |
| DE | 102020121462 B3 | 1/2022 | |
| DK | 9600118 | 11/1996 | |
| EP | 0032138 A2 | 7/1981 | |
| EP | 0066070 B1 | 12/1982 | |
| EP | 0068712 A1 | 1/1983 | |
| EP | 0140470 A1 | 5/1985 | |
| EP | 0220962 A1 | 5/1987 | |
| EP | 0140471 B1 | 5/1988 | |
| EP | 0274753 A2 | 7/1988 | |
| EP | 0119143 B1 | 11/1988 | |
| EP | 0483592 A1 | 5/1992 | |
| EP | 0483730 A1 | 5/1992 | |
| EP | 0610638 A1 | 8/1994 | |
| EP | 0613355 A1 | 9/1994 | |
| EP | 0711536 A1 | 5/1996 | |
| EP | 0613355 B1 | 1/1997 | |
| EP | 0680296 B1 | 5/1997 | |
| EP | 0787472 A1 | 8/1997 | |
| EP | 0966936 A1 | 12/1999 | |
| EP | 0987293 A1 | 3/2000 | |
| EP | 1063953 A1 | 1/2001 | |

(56)     References Cited

FOREIGN PATENT DOCUMENTS

| | | | |
|---|---|---|---|
| EP | 0653928 | B1 | 10/2002 |
| EP | 1332738 | A1 | 8/2003 |
| EP | 1382318 | A1 | 1/2004 |
| EP | 1089684 | B1 | 10/2004 |
| EP | 1616542 | A1 | 1/2006 |
| EP | 1382318 | B1 | 5/2006 |
| EP | 1063953 | B1 | 1/2007 |
| EP | 1658831 | B1 | 1/2008 |
| EP | 1872752 | A1 | 1/2008 |
| EP | 2180907 | A1 | 5/2010 |
| EP | 2380532 | A1 | 10/2011 |
| EP | 2389908 | A1 | 11/2011 |
| EP | 2601916 | A1 | 6/2013 |
| EP | 2676643 | A1 | 12/2013 |
| EP | 2470251 | B1 | 12/2014 |
| EP | 2997950 | A2 | 3/2016 |
| EP | 2879534 | B1 | 3/2017 |
| EP | 3424471 | A1 | 1/2019 |
| EP | 3169292 | B1 | 11/2019 |
| EP | 3753492 | A1 | 12/2020 |
| EP | 3777801 | A1 | 2/2021 |
| EP | 3788992 | A1 | 3/2021 |
| EP | 3576689 | B1 | 3/2022 |
| EP | 3752110 | B1 | 3/2022 |
| EP | 3787570 | B1 | 3/2022 |
| EP | 4025163 | A1 | 7/2022 |
| EP | 3463180 | B1 | 3/2023 |
| EP | 3749230 | B1 | 3/2023 |
| EP | 3569205 | B1 | 6/2023 |
| EP | 4192402 | A1 | 6/2023 |
| EP | 4218702 | A1 | 8/2023 |
| EP | 3624742 | B1 | 1/2024 |
| EP | 4382082 | A2 | 6/2024 |
| EP | 4445881 | A2 | 10/2024 |
| EP | 4464288 | A2 | 11/2024 |
| EP | 4215134 | B1 | 1/2025 |
| EP | 4494611 | A2 | 1/2025 |
| EP | 4527361 | A2 | 3/2025 |
| FR | 2826704 | A1 | 1/2003 |
| GB | 871820 | A | 7/1961 |
| GB | 0873045 | A | 7/1961 |
| GB | 1011517 | A | 12/1965 |
| GB | 1467144 | A | 3/1977 |
| GB | 2106395 | A | 4/1983 |
| GB | 2106784 | A | 4/1983 |
| GB | 2148126 | A | 5/1985 |
| GB | 2171315 | A | 8/1986 |
| GB | 2181953 | A | 5/1987 |
| GB | 2148126 | B | 7/1987 |
| GB | 2191095 | A | 12/1987 |
| GB | 2199750 | A | 7/1988 |
| GB | 2260907 | A | 5/1993 |
| GB | 2415386 | A | 12/2005 |
| GB | 2462267 | A | 2/2010 |
| GB | 2469496 | A | 10/2010 |
| GB | 2490327 | A | 10/2012 |
| GB | 2507318 | A | 4/2014 |
| GB | 2612752 | A | 5/2023 |
| IT | 201800009129 | A1 | 4/2020 |
| JP | S498638 | U | 1/1974 |
| JP | S5410596 | A | 1/1979 |
| JP | S5410596 | Y2 | 5/1979 |
| JP | S54155729 | U | 10/1979 |
| JP | S55155618 | A | 12/1980 |
| JP | S56152629 | U | 11/1981 |
| JP | S57142534 | U | 9/1982 |
| JP | S5888596 | U | 6/1983 |
| JP | S58188016 | A | 12/1983 |
| JP | S59118161 | A | 7/1984 |
| JP | S61502100 | A | 9/1986 |
| JP | S63107780 | U | 7/1988 |
| JP | H0267530 | A | 3/1990 |
| JP | H02103871 | A | 4/1990 |
| JP | H02131422 | A | 5/1990 |
| JP | H02131422 | U | 11/1990 |
| JP | H0460220 | A | 2/1992 |
| JP | H0515928 | U | 3/1993 |
| JP | H05123349 | A | 5/1993 |
| JP | H05123350 | A | 5/1993 |
| JP | H0626264 | U | 4/1994 |
| JP | 3087938 | B2 | 10/1995 |
| JP | H085630 | A | 1/1996 |
| JP | H08117271 | A | 5/1996 |
| JP | 2686634 | B2 | 12/1997 |
| JP | H1040141 | A | 2/1998 |
| JP | H10225430 | A | 8/1998 |
| JP | H11113946 | A | 4/1999 |
| JP | H11290365 | A | 10/1999 |
| JP | 2000116690 | A | 4/2000 |
| JP | 2000152953 | A | 6/2000 |
| JP | 2000185068 | A | 7/2000 |
| JP | 2000225139 | A | 8/2000 |
| JP | 2001054531 | A | 2/2001 |
| JP | 2001070331 | A | 3/2001 |
| JP | 2001224616 | A | 8/2001 |
| JP | 2001276107 | A | 10/2001 |
| JP | 2001276108 | A | 10/2001 |
| JP | 2002028173 | A | 1/2002 |
| JP | 2002502667 | A | 1/2002 |
| JP | 2002102285 | A | 4/2002 |
| JP | 2003038563 | A | 2/2003 |
| JP | 2003505152 | A | 2/2003 |
| JP | 2003126242 | A | 5/2003 |
| JP | 2003180722 | A | 7/2003 |
| JP | 2003227004 | A | 8/2003 |
| JP | 2003528691 | A | 9/2003 |
| JP | 2004057578 | A | 2/2004 |
| JP | 2004130056 | A | 4/2004 |
| JP | 2004267400 | A | 9/2004 |
| JP | 2004267530 | A | 9/2004 |
| JP | 2005052219 | A | 3/2005 |
| JP | 2005066011 | A | 3/2005 |
| JP | 2005066325 | A | 3/2005 |
| JP | 2005102978 | A | 4/2005 |
| JP | 2005518237 | A | 6/2005 |
| JP | 2005518901 | A | 6/2005 |
| JP | 2005323842 | A | 11/2005 |
| JP | 3749097 | B2 | 12/2005 |
| JP | 2006026108 | A | 2/2006 |
| JP | 3123547 | B2 | 6/2006 |
| JP | 2006136491 | A | 6/2006 |
| JP | 2006136492 | A | 6/2006 |
| JP | 2006204868 | A | 8/2006 |
| JP | 2007044494 | A | 2/2007 |
| JP | 3132659 | B2 | 5/2007 |
| JP | 2007209687 | A | 8/2007 |
| JP | 2007259898 | A | 10/2007 |
| JP | 4039641 | B2 | 11/2007 |
| JP | 2008005975 | A | 1/2008 |
| JP | 2009509570 | A | 3/2009 |
| JP | 2009165887 | A | 7/2009 |
| JP | 2009525776 | A | 7/2009 |
| JP | 2010504150 | A | 2/2010 |
| JP | 2010058795 | A | 3/2010 |
| JP | 2010081981 | A | 4/2010 |
| JP | 2010166954 | A | 8/2010 |
| JP | 4640772 | B2 | 12/2010 |
| JP | 2010536439 | A | 12/2010 |
| JP | 2011500225 | A | 1/2011 |
| JP | 2011030962 | A | 2/2011 |
| JP | 4747166 | B2 | 5/2011 |
| JP | 2011087823 | A | 5/2011 |
| JP | 4801218 | B1 | 8/2011 |
| JP | 2011522584 | A | 8/2011 |
| JP | 2011202664 | A | 10/2011 |
| JP | 2011218130 | A | 11/2011 |
| JP | 2011224070 | A | 11/2011 |
| JP | 3175719 | U | 4/2012 |
| JP | 2012523869 | A | 10/2012 |
| JP | 2013238608 | A | 11/2013 |
| JP | 2014521960 | A | 8/2014 |
| JP | 2015092945 | A | 5/2015 |
| JP | 2015513678 | A | 5/2015 |
| JP | 3198994 | B2 | 7/2015 |

(56) References Cited

FOREIGN PATENT DOCUMENTS

| | | | |
|---|---|---|---|
| JP | 2015221390 A | 12/2015 |
| JP | 2016521191 A | 7/2016 |
| JP | 2017014698 A | 1/2017 |
| JP | 3208707 U | 2/2017 |
| JP | 3209321 U | 3/2017 |
| JP | 2017070400 A | 4/2017 |
| JP | 2017512603 A | 5/2017 |
| JP | 2017127596 A | 7/2017 |
| JP | 2017201272 A | 11/2017 |
| JP | 2019010375 A | 1/2019 |
| JP | 2019076342 A | 5/2019 |
| JP | 2019525811 A | 9/2019 |
| JP | 2019170942 A | 10/2019 |
| JP | 2019533492 A | 11/2019 |
| JP | 2020510464 A | 4/2020 |
| JP | 2020520775 A | 7/2020 |
| JP | 2020124425 A | 8/2020 |
| JP | 2021007472 A | 1/2021 |
| JP | 2021041145 A | 3/2021 |
| JP | 2021074491 A | 5/2021 |
| JP | 2021120686 A | 8/2021 |
| JP | 2021520952 A | 8/2021 |
| JP | 2021522009 A | 8/2021 |
| JP | 2021522013 A | 8/2021 |
| JP | 2021522019 A | 8/2021 |
| JP | 7129493 B2 | 8/2022 |
| JP | 2022554252 A | 12/2022 |
| JP | 2023532132 A | 7/2023 |
| KR | 200290061 Y1 | 9/2002 |
| KR | 20030047451 A | 6/2003 |
| KR | 20080005516 A | 1/2008 |
| KR | 20090072069 A | 7/2009 |
| KR | 20090104426 A | 10/2009 |
| KR | 20090110359 A | 10/2009 |
| KR | 20120005922 A | 1/2012 |
| KR | 20140039485 A | 4/2014 |
| KR | 101432639 B1 | 8/2014 |
| KR | 20180106659 A | 10/2018 |
| KR | 20180108774 A | 10/2018 |
| KR | 20230034343 A | 3/2023 |
| PT | 2068717 E | 6/2013 |
| SE | 505542 C2 | 9/1997 |
| TW | 408207 B | 10/2000 |
| WO | 8101957 A1 | 7/1981 |
| WO | 8804558 A1 | 6/1988 |
| WO | 9104714 A2 | 4/1991 |
| WO | 9104714 A3 | 6/1991 |
| WO | 9220299 A3 | 2/1993 |
| WO | 9303690 A1 | 3/1993 |
| WO | 9307839 A1 | 4/1993 |
| WO | 9309736 A2 | 5/1993 |
| WO | 9309736 A3 | 6/1993 |
| WO | 9416914 A1 | 8/1994 |
| WO | 9514448 A2 | 6/1995 |
| WO | 9600096 A1 | 1/1996 |
| WO | 9634636 A1 | 11/1996 |
| WO | 9817211 A1 | 4/1998 |
| WO | 9830336 A1 | 7/1998 |
| WO | 0000112 A1 | 1/2000 |
| WO | 0000113 A1 | 1/2000 |
| WO | 0025651 A1 | 5/2000 |
| WO | 0033773 A1 | 6/2000 |
| WO | 0057784 A1 | 10/2000 |
| WO | 0069377 A1 | 11/2000 |
| WO | 0079497 A1 | 12/2000 |
| WO | 0145618 A1 | 6/2001 |
| WO | 0145621 A1 | 6/2001 |
| WO | 02094160 A1 | 11/2002 |
| WO | 03013967 A1 | 2/2003 |
| WO | 03015671 A1 | 2/2003 |
| WO | 03024824 A1 | 3/2003 |
| WO | 03055423 A1 | 7/2003 |
| WO | 03071931 A2 | 9/2003 |
| WO | 03079942 A1 | 10/2003 |
| WO | 03071931 A3 | 2/2004 |
| WO | 2004019836 A1 | 3/2004 |
| WO | 2004024046 A1 | 3/2004 |
| WO | 2004026195 A1 | 4/2004 |
| WO | 2005051252 A1 | 6/2005 |
| WO | 2005060558 A2 | 7/2005 |
| WO | 2005074571 A3 | 9/2005 |
| WO | 2005089687 A2 | 9/2005 |
| WO | 2005107661 A2 | 11/2005 |
| WO | 2006021220 A1 | 3/2006 |
| WO | 2006037140 A2 | 4/2006 |
| WO | 2007005851 A2 | 1/2007 |
| WO | 2007007845 A1 | 1/2007 |
| WO | 2007042823 A2 | 4/2007 |
| WO | 2007055651 A1 | 5/2007 |
| WO | 2006098950 A3 | 11/2007 |
| WO | 2007128156 A3 | 2/2008 |
| WO | 2008026106 A2 | 3/2008 |
| WO | 2008078117 A1 | 7/2008 |
| WO | 2008104019 A1 | 9/2008 |
| WO | 2008141471 A1 | 11/2008 |
| WO | 2009004368 A1 | 1/2009 |
| WO | 2009004369 A1 | 1/2009 |
| WO | 2009052496 A1 | 4/2009 |
| WO | 2009052502 A1 | 4/2009 |
| WO | 2009007702 A4 | 7/2009 |
| WO | 2009101738 A1 | 8/2009 |
| WO | 2010058192 A1 | 5/2010 |
| WO | 2010030122 A3 | 7/2010 |
| WO | 2010101915 A3 | 1/2011 |
| WO | 2011018132 A1 | 2/2011 |
| WO | 2011018133 A1 | 2/2011 |
| WO | 2011024864 A1 | 3/2011 |
| WO | 2011054118 A1 | 5/2011 |
| WO | 2011079132 A1 | 6/2011 |
| WO | 2011107972 A1 | 9/2011 |
| WO | 2011108972 A1 | 9/2011 |
| WO | 2011117292 A1 | 9/2011 |
| WO | 2011123219 A1 | 10/2011 |
| WO | 2011132043 A1 | 10/2011 |
| WO | 2012012908 A1 | 2/2012 |
| WO | 2012020506 A1 | 2/2012 |
| WO | 2012065274 A1 | 5/2012 |
| WO | 2012097462 A1 | 7/2012 |
| WO | 2012098796 A1 | 7/2012 |
| WO | 2012101288 A1 | 8/2012 |
| WO | 2012175916 A1 | 12/2012 |
| WO | 2013018435 A1 | 2/2013 |
| WO | 2013033429 A1 | 3/2013 |
| WO | 2013055434 A1 | 4/2013 |
| WO | 2013082397 A1 | 6/2013 |
| WO | 2013103291 A2 | 7/2013 |
| WO | 2013131109 A1 | 9/2013 |
| WO | 2013167478 A1 | 11/2013 |
| WO | 2013177716 A1 | 12/2013 |
| WO | 2014041534 A1 | 3/2014 |
| WO | 2014046420 A1 | 3/2014 |
| WO | 2014118518 A1 | 8/2014 |
| WO | 2014160852 A1 | 10/2014 |
| WO | 2015023599 A1 | 2/2015 |
| WO | 2015052348 A1 | 4/2015 |
| WO | 2015068384 A1 | 5/2015 |
| WO | 2015169403 A1 | 11/2015 |
| WO | 2015170307 A1 | 11/2015 |
| WO | 2015197462 A1 | 12/2015 |
| WO | 2016051385 A1 | 4/2016 |
| WO | 2016055989 A1 | 4/2016 |
| WO | 2016071894 A1 | 5/2016 |
| WO | 2016103242 A1 | 6/2016 |
| WO | 2016116915 A1 | 7/2016 |
| WO | 2016124203 A1 | 8/2016 |
| WO | 2016139448 A1 | 9/2016 |
| WO | 2016166562 A1 | 10/2016 |
| WO | 2016167535 A1 | 10/2016 |
| WO | 2016191574 A1 | 12/2016 |
| WO | 2016200088 A1 | 12/2016 |
| WO | 2016200361 A1 | 12/2016 |
| WO | 2016204731 A1 | 12/2016 |
| WO | 2017001532 A2 | 1/2017 |
| WO | 2017075226 A1 | 5/2017 |

(56) References Cited

FOREIGN PATENT DOCUMENTS

| | | | |
|---|---|---|---|
| WO | 2017100511 A1 | 6/2017 |
| WO | 2017152198 A1 | 9/2017 |
| WO | 2017153357 A1 | 9/2017 |
| WO | 2017162559 A1 | 9/2017 |
| WO | 2017205446 A1 | 11/2017 |
| WO | 2017209779 A1 | 12/2017 |
| WO | 2017210524 A1 | 12/2017 |
| WO | 2018022414 A1 | 2/2018 |
| WO | 2018044781 A1 | 3/2018 |
| WO | 2018056953 A1 | 3/2018 |
| WO | 2018090550 A1 | 5/2018 |
| WO | 2018138513 A1 | 8/2018 |
| WO | 2018144318 A1 | 8/2018 |
| WO | 2018144463 A1 | 8/2018 |
| WO | 2018150263 A1 | 8/2018 |
| WO | 2018150268 A1 | 8/2018 |
| WO | 2018152156 A1 | 8/2018 |
| WO | 2018183791 A1 | 10/2018 |
| WO | 2018150267 A3 | 11/2018 |
| WO | 2018235026 A1 | 12/2018 |
| WO | 2018235065 A1 | 12/2018 |
| WO | 2019004404 A1 | 1/2019 |
| WO | 2019041005 A1 | 3/2019 |
| WO | 2019044217 A1 | 3/2019 |
| WO | 2019044218 A1 | 3/2019 |
| WO | 2019044219 A1 | 3/2019 |
| WO | 2019050959 A1 | 3/2019 |
| WO | 2019065541 A1 | 4/2019 |
| WO | 2019096845 A1 | 5/2019 |
| WO | 2019150385 A1 | 8/2019 |
| WO | 2019161094 A1 | 8/2019 |
| WO | 2019188566 A1 | 10/2019 |
| WO | 2019190593 A1 | 10/2019 |
| WO | 2019212949 A1 | 11/2019 |
| WO | 2019212950 A1 | 11/2019 |
| WO | 2019212951 A1 | 11/2019 |
| WO | 2019212952 A1 | 11/2019 |
| WO | 2019212954 A1 | 11/2019 |
| WO | 2019212955 A1 | 11/2019 |
| WO | 2019212956 A1 | 11/2019 |
| WO | 2019214787 A1 | 11/2019 |
| WO | 2019214788 A1 | 11/2019 |
| WO | 2019226826 A1 | 11/2019 |
| WO | 2019239433 A1 | 12/2019 |
| WO | 2020000994 A1 | 1/2020 |
| WO | 2020020618 A1 | 1/2020 |
| WO | 2020033752 A1 | 2/2020 |
| WO | 2020038822 A1 | 2/2020 |
| WO | 2020088409 A1 | 5/2020 |
| WO | 2020049394 A3 | 6/2020 |
| WO | 2020120657 A1 | 6/2020 |
| WO | 2020152575 A1 | 7/2020 |
| WO | 2020182923 A1 | 9/2020 |
| WO | 2020204967 A1 | 10/2020 |
| WO | 2020205939 A1 | 10/2020 |
| WO | 2020209898 A1 | 10/2020 |
| WO | 2020242790 A1 | 12/2020 |
| WO | 2020251893 A1 | 12/2020 |
| WO | 2020256865 A1 | 12/2020 |
| WO | 2021007144 A1 | 1/2021 |
| WO | 2021007345 A1 | 1/2021 |
| WO | 2021010844 A1 | 1/2021 |
| WO | 2021016026 A1 | 1/2021 |
| WO | 2021016056 A1 | 1/2021 |
| WO | 2021016300 A1 | 1/2021 |
| WO | 2021025919 A1 | 2/2021 |
| WO | 2021034886 A1 | 2/2021 |
| WO | 2021041123 A1 | 3/2021 |
| WO | 2021046501 A1 | 3/2021 |
| WO | 2021086868 A1 | 5/2021 |
| WO | 2021094352 A1 | 5/2021 |
| WO | 2021094639 A1 | 5/2021 |
| WO | 2021097067 A1 | 5/2021 |
| WO | 2021102296 A1 | 5/2021 |
| WO | 2021107025 A1 | 6/2021 |
| WO | 2021138411 A1 | 7/2021 |
| WO | 2021138414 A1 | 7/2021 |
| WO | 2021154686 A1 | 8/2021 |
| WO | 2021155206 A1 | 8/2021 |
| WO | 2021170075 A1 | 9/2021 |
| WO | 2021173436 A1 | 9/2021 |
| WO | 2021188817 A1 | 9/2021 |
| WO | 2021195384 A1 | 9/2021 |
| WO | 2021205995 A1 | 10/2021 |
| WO | 2021207621 A1 | 10/2021 |
| WO | 2021211568 A1 | 10/2021 |
| WO | 2021211801 A1 | 10/2021 |
| WO | 2021211914 A1 | 10/2021 |
| WO | 2021216419 A1 | 10/2021 |
| WO | 2021216422 A1 | 10/2021 |
| WO | 2021231532 A1 | 11/2021 |
| WO | 2021247523 A1 | 12/2021 |
| WO | 2021257202 A1 | 12/2021 |
| WO | 2022006256 A1 | 1/2022 |
| WO | 2022029662 A1 | 2/2022 |
| WO | 2022031943 A1 | 2/2022 |
| WO | 2022035745 A1 | 2/2022 |
| WO | 2022051220 A1 | 3/2022 |
| WO | 2022051360 A1 | 3/2022 |
| WO | 2022054613 A1 | 3/2022 |
| WO | 2022066704 A1 | 3/2022 |
| WO | 2022067392 A1 | 4/2022 |
| WO | 2022069950 A1 | 4/2022 |
| WO | 2022071429 A1 | 4/2022 |
| WO | 2022076322 A1 | 4/2022 |
| WO | 2022076427 A2 | 4/2022 |
| WO | 2022086898 A1 | 4/2022 |
| WO | 2022090199 A1 | 5/2022 |
| WO | 2022098536 A1 | 5/2022 |
| WO | 2022099087 A1 | 5/2022 |
| WO | 2022101999 A1 | 5/2022 |
| WO | 2022115692 A1 | 6/2022 |
| WO | 2022125685 A1 | 6/2022 |
| WO | 2022140545 A1 | 6/2022 |
| WO | 2022145231 A1 | 7/2022 |
| WO | 2022150290 A1 | 7/2022 |
| WO | 2022150360 A1 | 7/2022 |
| WO | 2022150463 A1 | 7/2022 |
| WO | 2022159392 A1 | 7/2022 |
| WO | 2022170182 A1 | 8/2022 |
| WO | 2022173803 A1 | 8/2022 |
| WO | 2022182385 A1 | 9/2022 |
| WO | 2022187152 A1 | 9/2022 |
| WO | 2022192188 A1 | 9/2022 |
| WO | 2022192347 A1 | 9/2022 |
| WO | 2022204000 A1 | 9/2022 |
| WO | 2022216507 A1 | 10/2022 |
| WO | 2022216776 A1 | 10/2022 |
| WO | 2022222030 A1 | 10/2022 |
| WO | 2022251184 A1 | 12/2022 |
| WO | 2022251425 A1 | 12/2022 |
| WO | 2022271783 A1 | 12/2022 |
| WO | 2023286058 A1 | 1/2023 |
| WO | 2023014639 A1 | 2/2023 |
| WO | 2023014641 A1 | 2/2023 |
| WO | 2023018475 A2 | 2/2023 |
| WO | 2023018656 A1 | 2/2023 |
| WO | 2023018657 A1 | 2/2023 |
| WO | 2023023777 A1 | 3/2023 |
| WO | 2023034139 A1 | 3/2023 |
| WO | 2023034453 A1 | 3/2023 |
| WO | 2023038945 A1 | 3/2023 |
| WO | 2023038950 A1 | 3/2023 |
| WO | 2023049109 A1 | 3/2023 |
| WO | 2023049156 A1 | 3/2023 |
| WO | 2023049175 A1 | 3/2023 |
| WO | 2023086394 A1 | 5/2023 |
| WO | 2023149884 A1 | 8/2023 |
| WO | 2023149902 A1 | 8/2023 |
| WO | 2023149903 A1 | 8/2023 |
| WO | 2023154390 A1 | 8/2023 |
| WO | 2023163725 A1 | 8/2023 |
| WO | 2023191764 A1 | 10/2023 |
| WO | 2023244238 A1 | 12/2023 |

(56) References Cited

FOREIGN PATENT DOCUMENTS

| WO | 2024043871 A1 | 2/2024 |
| WO | 2024058788 A1 | 3/2024 |
| WO | 2024253655 A1 | 12/2024 |
| WO | 2025034959 A1 | 2/2025 |
| WO | 2025038087 A1 | 2/2025 |
| WO | 2025038088 A1 | 2/2025 |
| WO | 2025048789 A1 | 3/2025 |
| WO | 2025071622 A1 | 4/2025 |
| WO | 2025179267 A1 | 8/2025 |

OTHER PUBLICATIONS

Advisory Action for U.S. Appl. No. 16/452,258 mailed Apr. 8, 2024.
Advisory Action for U.S. Appl. No. 16/478,180 mailed Jun. 7, 2024.
Advisory Action for U.S. Appl. No. 17/444,792 mailed Jul. 8, 2024.
Advisory Action for U.S. Appl. No. 17/446,654 mailed Apr. 15, 2024.
Advisory Action for U.S. Appl. No. 17/450,864 mailed Mar. 21, 2024.
Advisory Action for U.S. Appl. No. 17/451,345 mailed Jul. 3, 2024.
Advisory Action for U.S. Appl. No. 17/501,591 mailed Feb. 22, 2024.
Advisory Action for U.S. Appl. No. 17/645,821 mailed Jul. 2, 2024.
Advisory Action for U.S. Appl. No. 17/646,771 mailed Feb. 29, 2024.
Advisory Action for U.S. Appl. No. 17/661,090 mailed Feb. 26, 2024.
Advisory Action for U.S. Appl. No. 17/663,330 mailed Feb. 27, 2024.
Advisory Action for U.S. Appl. No. 17/664,487 mailed Mar. 13, 2024.
Advisory Action for U.S. Appl. No. 17/808,354 mailed Jun. 12, 2024.
Advisory Action for U.S. Appl. No. 18/139,523 mailed Apr. 24, 2024.
Advisory Action for U.S. Appl. No. 18/140,163 mailed Jun. 3, 2024.
Advisory Action for U.S. Appl. No. 18/140,751 mailed Apr. 24, 2024.
Advisory Action for U.S. Appl. No. 18/164,800 mailed Feb. 12, 2024.
Corrected Notice of Allowability for U.S. Appl. No. 17/326,980 mailed Feb. 8, 2024.
Corrected Notice of Allowability for U.S. Appl. No. 17/657,474 mailed Mar. 13, 2024.
Corrected Notice of Allowability for U.S. Appl. No. 17/657,474 mailed May 14, 2024.
Final Office Action for U.S. Appl. No. 16/478,180 mailed Feb. 28, 2024.
Final Office Action for U.S. Appl. No. 17/051,585 mailed Jul. 5, 2024.
Final Office Action for U.S. Appl. No. 17/051,600 mailed Jun. 27, 2024.
Final Office Action for U.S. Appl. No. 17/444,792 mailed Apr. 3, 2024.
Final Office Action for U.S. Appl. No. 17/446,654 mailed Jan. 31, 2024.
Final Office Action for U.S. Appl. No. 17/447,123 mailed May 14, 2024.
Final Office Action for U.S. Appl. No. 17/451,345 mailed Apr. 18, 2024.
Final Office Action for U.S. Appl. No. 17/645,821 mailed Apr. 3, 2024.
Final Office Action for U.S. Appl. No. 17/808,354 mailed Apr. 10, 2024.
Final Office Action for U.S. Appl. No. 18/140,163 mailed Mar. 27, 2024.
International Search Report and Written Opinion from International Application No. PCT/US2023/025192 mailed Feb. 7, 2024.
International Search Report and Written Opinion from International Application No. PCT/US2023/025939 mailed Feb. 7, 2024.
International Search Report and Written Opinion from International Application No. PCT/US2023/030365 mailed Mar. 13, 2024.
International Search Report and Written Opinion from International Application No. PCT/US2023/030373 mailed Mar. 13, 2024.
International Search Report and Written Opinion from International Application No. PCT/US2023/031433 mailed Mar. 4, 2024.
International Search Report and Written Opinion from International Application No. PCT/US2023/031740 mailed Mar. 4, 2024.
International Search Report and Written Opinion from International Application No. PCT/US2023/036868 mailed Jun. 5, 2024.
International Search Report and Written Opinion from International Application No. PCT/US2023/075507 mailed Jun. 13, 2024.
International Search Report and Written Opinion from International Application No. PCT/US2023/077208 mailed May 10, 2024.
Issue Notification for U.S. Appl. No. 16/449,039 mailed Jun. 19, 2024.
Issue Notification for U.S. Appl. No. 17/051,550 mailed Mar. 13, 2024.
Issue Notification for U.S. Appl. No. 17/051,554 mailed Mar. 6, 2024.
Issue Notification for U.S. Appl. No. 17/326,980 mailed Jul. 10, 2024.
Issue Notification for U.S. Appl. No. 17/448,811 mailed Jul. 3, 2024.
Issue Notification for U.S. Appl. No. 17/453,260 mailed Jul. 10, 2024.
Issue Notification for U.S. Appl. No. 17/657,474 mailed Jun. 19, 2024.
Issue Notification for U.S. Appl. No. 18/299,788 mailed Feb. 21, 2024.
Non-Final Office Action for U.S. Appl. No. 16/369,676 mailed Feb. 29, 2024.
Non-Final Office Action for U.S. Appl. No. 16/433,773 mailed Feb. 26, 2024.
Non-Final Office Action for U.S. Appl. No. 16/452,258 mailed Jun. 20, 2024.
Non-Final Office Action for U.S. Appl. No. 16/904,868 mailed Mar. 12, 2024.
Non-Final Office Action for U.S. Appl. No. 17/179,116 mailed Feb. 26, 2024.
Non-Final Office Action for U.S. Appl. No. 17/378,015 mailed Jul. 5, 2024.
Non-Final Office Action for U.S. Appl. No. 17/446,256 mailed Feb. 13, 2024.
Non-Final Office Action for U.S. Appl. No. 17/446,654 mailed Jun. 25, 2024.
Non-Final Office Action for U.S. Appl. No. 17/450,864 mailed May 29, 2024.
Non-Final Office Action for U.S. Appl. No. 17/451,354 mailed Apr. 4, 2024.
Non-Final Office Action for U.S. Appl. No. 17/595,747 mailed Jun. 7, 2024.
Non-Final Office Action for U.S. Appl. No. 17/597,673 mailed Mar. 20, 2024.
Non-Final Office Action for U.S. Appl. No. 17/646,771 mailed Apr. 24, 2024.
Non-Final Office Action for U.S. Appl. No. 17/653,920 mailed Mar. 15, 2024.
Non-Final Office Action for U.S. Appl. No. 17/655,464 mailed Mar. 26, 2024.
Non-Final Office Action for U.S. Appl. No. 17/661,090 mailed May 22, 2024.
Non-Final Office Action for U.S. Appl. No. 17/663,330 mailed Jul. 1, 2024.
Non-Final Office Action for U.S. Appl. No. 17/664,487 mailed Jun. 17, 2024.
Non-Final Office Action for U.S. Appl. No. 17/664,914 mailed Jan. 31, 2024.
Non-Final Office Action for U.S. Appl. No. 18/003,029 mailed Mar. 26, 2024.

(56) References Cited

OTHER PUBLICATIONS

Non-Final Office Action for U.S. Appl. No. 18/140,751 mailed Jun. 21, 2024.
Non-Final Office Action for U.S. Appl. No. 18/164,800 mailed Mar. 22, 2024.
Non-Final Office Action for U.S. Appl. No. 18/389,009 mailed May 24, 2024.
Notice of Allowance for U.S. Appl. No. 16/369,676 mailed Jun. 17, 2024.
Notice of Allowance for U.S. Appl. No. 16/449,039 mailed Mar. 28, 2024.
Notice of Allowance for U.S. Appl. No. 16/452,145 mailed Jul. 11, 2024.
Notice of Allowance for U.S. Appl. No. 17/051,550 mailed Feb. 7, 2024.
Notice of Allowance for U.S. Appl. No. 17/326,980 mailed Apr. 5, 2024.
Notice of Allowance for U.S. Appl. No. 17/448,811 mailed Jun. 14, 2024.
Notice of Allowance for U.S. Appl. No. 17/453,260 mailed Apr. 8, 2024.
Notice of Allowance for U.S. Appl. No. 17/453,560 mailed Jan. 31, 2024.
Notice of Allowance for U.S. Appl. No. 17/657,474 mailed Mar. 5, 2024.
Notice of Allowance for U.S. Appl. No. 17/657,474 mailed May 2, 2024.
Notice of Allowance for U.S. Appl. No. 17/662,700 mailed Jun. 12, 2024.
Notice of Allowance for U.S. Appl. No. 17/662,700 mailed Mar. 6, 2024.
Notice of Allowance for U.S. Appl. No. 18/198,464 mailed Apr. 17, 2024.
Restriction Requirement for U.S. Appl. No. 17/527,769 mailed Jun. 17, 2024.
Restriction Requirement for U.S. Appl. No. 17/667,097 mailed Mar. 20, 2024.
Supplemental Notice of Allowance for U.S. Appl. No. 17/051,550 mailed Feb. 21, 2024.
Supplemental Notice of Allowance for U.S. Appl. No. 17/051,554 mailed Feb. 14, 2024.
U.S. Appl. No. 17/444,792, filed Aug. 10, 2021.
U.S. Appl. No. 18/249,577, filed Oct. 19, 2021.
U.S. Appl. No. 18/294,403, filed Feb. 1, 2024.
U.S. Appl. No. 18/584,002, filed Feb. 22, 2024.
U.S. Appl. No. 18/610,523, filed Mar. 20, 2024.
U.S. Appl. No. 18/662,216, filed May 13, 2024.
U.S. Appl. No. 18/681,987, filed Feb. 7, 2024.
U.S. Appl. No. 18/682,006, filed Feb. 7, 2024.
U.S. Appl. No. 18/687,117, filed Feb. 27, 2024.
U.S. Appl. No. 18/688,023, filed Feb. 29, 2024.
U.S. Appl. No. 18/693,638, filed Mar. 20, 2024.
U.S. Appl. No. 18/694,090, filed Mar. 21, 2024.
U.S. Appl. No. 18/728,604, filed Jul. 12, 2024.
U.S. Appl. No. 18/757,964, filed Jun. 28, 2024.
U.S. Appl. No. 18/758,025, filed Jun. 28, 2024.
U.S. Appl. No. 63/561,893, filed Dec. 11, 2023.
"Oblong", Cambridge Dictionary, https://dictionary.cambridge.org/dictionary/english/oblong, 2024, 1 page.
Britannica, "Polyolefin", Britannica Online Encyclopedia, T. Editors of Encyclopaedia, https://www.britannica.com/science/polyolefin, Jul. 26, 2012.
Martin, et al., "Chapter 5 Applications of Polyethylene Oxide (POLYOX) in Hydrophilic Matrices", Hydrophilic Matrix Tablets for Oral Controlled Release, AAPS Advances in the Pharmaceutical Sciences vol. 16, 2014, pp. 123-141.
Wikipedia Article, "Decibel", https://web.archive.org/web/2020041521917/https://en.wikipedia/org/wiki/Decibel last accessed Mar. 11, 2024, 21 pages.

Wikipedia Article, "Fiberglass", https://web.archive.org.web/20200309194847/https://en.wikipedia.org/wiki/Fiberglass last accessed Mar. 11, 2024.
Advisory Action for U.S. Appl. No. 14/952,591 mailed Jun. 1, 2018.
Advisory Action for U.S. Appl. No. 15/238,427 mailed Apr. 10, 2019.
Advisory Action for U.S. Appl. No. 16/245,726 mailed Apr. 19, 2023.
Advisory Action for U.S. Appl. No. 16/369,676 mailed Mar. 24, 2023.
Advisory Action for U.S. Appl. No. 16/433,773 mailed Dec. 29, 2023.
Advisory Action for U.S. Appl. No. 16/433,773 mailed Feb. 15, 2023.
Advisory Action for U.S. Appl. No. 16/449,039 mailed Jan. 25, 2024.
Advisory Action for U.S. Appl. No. 16/452,258 mailed Oct. 26, 2022.
Advisory Action for U.S. Appl. No. 16/478,180 mailed Sep. 21, 2022.
Advisory Action for U.S. Appl. No. 16/478,180 mailed Sep. 7, 2023.
Advisory Action for U.S. Appl. No. 16/899,956 mailed Jul. 9, 2021.
Advisory Action for U.S. Appl. No. 16/904,868 mailed Jan. 2, 2024.
Advisory Action for U.S. Appl. No. 16/904,868 mailed Jul. 2, 2021.
Advisory Action for U.S. Appl. No. 16/904,868 mailed Jun. 15, 2022.
Advisory Action for U.S. Appl. No. 16/905,400 mailed Feb. 16, 2022.
Advisory Action for U.S. Appl. No. 16/905,400 mailed Jun. 9, 2021.
Advisory Action for U.S. Appl. No. 17/051,550 mailed Sep. 8, 2023.
Advisory Action for U.S. Appl. No. 17/051,585 mailed Oct. 17, 2023.
Advisory Action for U.S. Appl. No. 17/179,116 mailed Jan. 8, 2024.
Advisory Action for U.S. Appl. No. 17/444,792 mailed Aug. 25, 2023.
Advisory Action for U.S. Appl. No. 17/446,256 mailed Dec. 8, 2023.
Advisory Action for U.S. Appl. No. 17/448,811 mailed Nov. 15, 2023.
Advisory Action for U.S. Appl. No. 17/451,345 mailed Oct. 20, 2023.
Advisory Action for U.S. Appl. No. 17/451,354 mailed Jan. 30, 2024.
Advisory Action for U.S. Appl. No. 17/453,260 mailed Dec. 22, 2023.
Advisory Action for U.S. Appl. No. 17/653,137 mailed Dec. 1, 2023.
Advisory Action for U.S. Appl. No. 17/655,464 mailed Dec. 13, 2023.
Advisory Action for U.S. Appl. No. 17/662,700 mailed Jan. 30, 2023.
Communication of Notice of Opposition of European Application No. 17807547.9 mailed Jan. 5, 2024.
Corrected International Search Report and Written Opinion for International Application No. PCT/US2017/043025 mailed Jan. 11, 2018.
Corrected Notice of Allowability for U.S. Appl. No. 15/221,106 mailed Jul. 2, 2019.
Corrected Notice of Allowability for U.S. Appl. No. 15/612,325 mailed Mar. 17, 2021.
Corrected Notice of Allowability for U.S. Appl. No. 16/369,676 mailed Dec. 7, 2023.
Corrected Notice of Allowability for U.S. Appl. No. 17/330,657 mailed Dec. 9, 2021.
Final Office Action for U.S. Appl. No. 14/947,759 mailed Apr. 8, 2016.
Final Office Action for U.S. Appl. No. 14/952,591 mailed Feb. 23, 2018.
Final Office Action for U.S. Appl. No. 14/952,591 mailed Nov. 1, 2019.
Final Office Action for U.S. Appl. No. 14/952,591 mailed Nov. 27, 2020.

(56)    References Cited

OTHER PUBLICATIONS

Final Office Action for U.S. Appl. No. 15/171,968 mailed Feb. 14, 2020.
Final Office Action for U.S. Appl. No. 15/171,968 mailed Mar. 19, 2019.
Final Office Action for U.S. Appl. No. 15/221,106 mailed Jan. 23, 2019.
Final Office Action for U.S. Appl. No. 15/238,427 mailed Jan. 2, 2019.
Final Office Action for U.S. Appl. No. 15/260,103 mailed Feb. 14, 2019.
Final Office Action for U.S. Appl. No. 15/612,325 mailed Sep. 17, 2020.
Final Office Action for U.S. Appl. No. 16/245,726 mailed Nov. 25, 2022.
Final Office Action for U.S. Appl. No. 16/369,676 mailed Aug. 31, 2023.
Final Office Action for U.S. Appl. No. 16/369,676 mailed Dec. 5, 2022.
Final Office Action for U.S. Appl. No. 16/433,773 mailed Oct. 10, 2023.
Final Office Action for U.S. Appl. No. 16/433,773 mailed Oct. 25, 2022.
Final Office Action for U.S. Appl. No. 16/449,039 mailed Aug. 1, 2022.
Final Office Action for U.S. Appl. No. 16/449,039 mailed Nov. 21, 2023.
Final Office Action for U.S. Appl. No. 16/452,145 mailed Mar. 25, 2022.
Final Office Action for U.S. Appl. No. 16/452,258 mailed Dec. 21, 2023.
Final Office Action for U.S. Appl. No. 16/452,258 mailed Jun. 14, 2022.
Final Office Action for U.S. Appl. No. 16/478,180 mailed Jun. 22, 2022.
Final Office Action for U.S. Appl. No. 16/478,180 mailed May 31, 2023.
Final Office Action for U.S. Appl. No. 16/899,956 mailed Apr. 19, 2021.
Final Office Action for U.S. Appl. No. 16/904,868 mailed Mar. 10, 2022.
Final Office Action for U.S. Appl. No. 16/904,868 mailed Mar. 26, 2021.
Final Office Action for U.S. Appl. No. 16/904,868 mailed Nov. 2, 2023.
Final Office Action for U.S. Appl. No. 16/905,400 mailed Apr. 6, 2021.
Final Office Action for U.S. Appl. No. 16/905,400 mailed Dec. 9, 2021.
Final Office Action for U.S. Appl. No. 17/051,399 mailed Jan. 8, 2024.
Final Office Action for U.S. Appl. No. 17/051,399 mailed Mar. 9, 2023.
Final Office Action for U.S. Appl. No. 17/051,550 mailed May 23, 2023.
Final Office Action for U.S. Appl. No. 17/051,585 mailed Jul. 27, 2023.
Final Office Action for U.S. Appl. No. 17/088,272 mailed May 25, 2021.
Final Office Action for U.S. Appl. No. 17/179,116 mailed Oct. 31, 2023.
Final Office Action for U.S. Appl. No. 17/444,792 mailed Jun. 15, 2023.
Final Office Action for U.S. Appl. No. 17/446,256 mailed Sep. 19, 2023.
Final Office Action for U.S. Appl. No. 17/448,811 mailed Aug. 3, 2023.
Final Office Action for U.S. Appl. No. 17/450,864 mailed Dec. 28, 2023.
Final Office Action for U.S. Appl. No. 17/451,345 mailed May 3, 2023.
Final Office Action for U.S. Appl. No. 17/451,354 mailed Oct. 30, 2023.
Final Office Action for U.S. Appl. No. 17/453,260 mailed Oct. 5, 2023.
Final Office Action for U.S. Appl. No. 17/501,591 mailed Nov. 14, 2023.
Final Office Action for U.S. Appl. No. 17/646,771 mailed Dec. 21, 2023.
Final Office Action for U.S. Appl. No. 17/653,137 mailed Sep. 21, 2023.
Final Office Action for U.S. Appl. No. 17/655,464 mailed Sep. 1, 2023.
Final Office Action for U.S. Appl. No. 17/661,090 mailed Dec. 11, 2023.
Final Office Action for U.S. Appl. No. 17/662,700 mailed Sep. 30, 2022.
Final Office Action for U.S. Appl. No. 17/663,330 mailed Dec. 12, 2023.
Final Office Action for U.S. Appl. No. 17/664,487 mailed Jan. 4, 2024.
Final Office Action for U.S. Appl. No. 18/139,523 mailed Dec. 22, 2023.
Final Office Action for U.S. Appl. No. 18/140,751 mailed Jan. 17, 2024.
Final Office Action for U.S. Appl. No. 18/164,800 mailed Dec. 6, 2023.
Final Office Action for U.S. Appl. No. 29/624,661 mailed Feb. 18, 2020.
International Search Report and Written Opinion from International Application No. PCT/IB2021/057173 mailed Nov. 5, 2021.
International Search Report and Written Opinion from International Application No. PCT/US2016/049274 mailed Dec. 1, 2016.
International Search Report and Written Opinion from International Application No. PCT/US2017/035625 mailed Aug. 15, 2017.
International Search Report and Written Opinion from International Application No. PCT/US2017/043025 mailed Oct. 18, 2017.
International Search Report and Written Opinion from International Application No. PCT/US2018/015968 mailed Apr. 6, 2018.
International Search Report and Written Opinion from International Application No. PCT/US2019/029608 mailed Sep. 3, 2019.
International Search Report and Written Opinion from International Application No. PCT/US2019/029609 mailed Sep. 3, 2019.
International Search Report and Written Opinion from International Application No. PCT/US2019/029610 mailed Sep. 3, 2019.
International Search Report and Written Opinion from International Application No. PCT/US2019/029611 mailed Jul. 3, 2019.
International Search Report and Written Opinion from International Application No. PCT/US2019/029613 mailed Jul. 3, 2019.
International Search Report and Written Opinion from International Application No. PCT/US2019/029614 mailed Sep. 26, 2019.
International Search Report and Written Opinion from International Application No. PCT/US2019/029616 mailed Aug. 30, 2019.
International Search Report and Written Opinion from International Application No. PCT/US2020/023572 mailed Jul. 6, 2020.
International Search Report and Written Opinion from International Application No. PCT/US2020/033064 mailed Aug. 31, 2020.
International Search Report and Written Opinion from International Application No. PCT/US2020/033122 mailed Aug. 31, 2020.
International Search Report and Written Opinion from International Application No. PCT/US2020/040860 mailed Oct. 2, 2020.
International Search Report and Written Opinion from International Application No. PCT/US2020/041242 mailed Nov. 17, 2020.
International Search Report and Written Opinion from International Application No. PCT/US2020/041249 mailed Oct. 2, 2020.
International Search Report and Written Opinion from International Application No. PCT/US2020/042262 mailed Oct. 14, 2020.
International Search Report and Written Opinion from International Application No. PCT/US2020/043059 mailed Oct. 6, 2020.
International Search Report and Written Opinion from International Application No. PCT/US2020/044024 mailed Nov. 12, 2020.

(56)        References Cited

OTHER PUBLICATIONS

International Search Report and Written Opinion from International Application No. PCT/US2020/046914 mailed Dec. 1, 2020.
International Search Report and Written Opinion from International Application No. PCT/US2020/055680 mailed Dec. 15, 2020.
International Search Report and Written Opinion from International Application No. PCT/US2020/057562 mailed Jan. 27, 2021.
International Search Report and Written Opinion from International Application No. PCT/US2020/061563 mailed Feb. 19, 2021.
International Search Report and Written Opinion from International Application No. PCT/US2020/065234 mailed Apr. 12, 2021.
International Search Report and Written Opinion from International Application No. PCT/US2020/067451 mailed Mar. 25, 2021.
International Search Report and Written Opinion from International Application No. PCT/US2020/067454 mailed Mar. 29, 2021.
International Search Report and Written Opinion from International Application No. PCT/US2020/067455 mailed Mar. 26, 2021.
International Search Report and Written Opinion from International Application No. PCT/US2021/015024 mailed May 18, 2021.
International Search Report and Written Opinion from International Application No. PCT/US2021/015787 mailed May 27, 2021.
International Search Report and Written Opinion from International Application No. PCT/US2021/023001 mailed Jun. 21, 2021.
International Search Report and Written Opinion from International Application No. PCT/US2021/024162 mailed Jul. 8, 2021.
International Search Report and Written Opinion from International Application No. PCT/US2021/026607 mailed Jul. 29, 2021.
International Search Report and Written Opinion from International Application No. PCT/US2021/027061 mailed Jul. 19, 2021.
International Search Report and Written Opinion from International Application No. PCT/US2021/027104 mailed Jul. 6, 2021.
International Search Report and Written Opinion from International Application No. PCT/US2021/027314 mailed Jul. 6, 2021.
International Search Report and Written Opinion from International Application No. PCT/US2021/027422 mailed Aug. 12, 2021.
International Search Report and Written Opinion from International Application No. PCT/US2021/027425 mailed Aug. 11, 2021.
International Search Report and Written Opinion from International Application No. PCT/US2021/027913 mailed Jul. 12, 2021.
International Search Report and Written Opinion from International Application No. PCT/US2021/027917 mailed Aug. 19, 2021.
International Search Report and Written Opinion from International Application No. PCT/US2021/039866 mailed Oct. 7, 2021.
International Search Report and Written Opinion from International Application No. PCT/US2021/043893 mailed Nov. 22, 2021.
International Search Report and Written Opinion from International Application No. PCT/US2021/044699 mailed Nov. 22, 2021.
International Search Report and Written Opinion from International Application No. PCT/US2021/045188 mailed Jan. 26, 2022.
International Search Report and Written Opinion from International Application No. PCT/US2021/047536 mailed Dec. 23, 2021.
International Search Report and Written Opinion from International Application No. PCT/US2021/048211 mailed Dec. 22, 2021.
International Search Report and Written Opinion from International Application No. PCT/US2021/048661 mailed Feb. 14, 2022.
International Search Report and Written Opinion from International Application No. PCT/US2021/049404 mailed Jan. 18, 2022.
International Search Report and Written Opinion from International Application No. PCT/US2021/051456 mailed Jan. 19, 2022.
International Search Report and Written Opinion from International Application No. PCT/US2021/053593 mailed Apr. 11, 2022.
International Search Report and Written Opinion from International Application No. PCT/US2021/055515 mailed Jan. 28, 2022.
International Search Report and Written Opinion from International Application No. PCT/US2021/056566 mailed Feb. 11, 2022.
International Search Report and Written Opinion from International Application No. PCT/US2021/060993 mailed Mar. 18, 2022.
International Search Report and Written Opinion from International Application No. PCT/US2021/062440 mailed Mar. 28, 2022.

International Search Report and Written Opinion from International Application No. PCT/US2022/011108 mailed Apr. 22, 2022.
International Search Report and Written Opinion from International Application No. PCT/US2022/011281 mailed Apr. 25, 2022.
International Search Report and Written Opinion from International Application No. PCT/US2022/011419 mailed Jun. 7, 2022.
International Search Report and Written Opinion from International Application No. PCT/US2022/011421 mailed Jun. 13, 2022.
International Search Report and Written Opinion from International Application No. PCT/US2022/012794 mailed May 3, 2022.
International Search Report and Written Opinion from International Application No. PCT/US2022/014285 mailed Sep. 28, 2022.
International Search Report and Written Opinion from International Application No. PCT/US2022/014749 mailed Sep. 28, 2022.
International Search Report and Written Opinion from International Application No. PCT/US2022/015026 mailed Oct. 31, 2022.
International Search Report and Written Opinion from International Application No. PCT/US2022/015045 mailed Sep. 9, 2022.
International Search Report and Written Opinion from International Application No. PCT/US2022/015073 mailed Sep. 8, 2022.
International Search Report and Written Opinion from International Application No. PCT/US2022/015418 mailed Nov. 11, 2022.
International Search Report and Written Opinion from International Application No. PCT/US2022/015420 mailed Nov. 18, 2022.
International Search Report and Written Opinion from International Application No. PCT/US2022/015471 mailed May 16, 2022.
International Search Report and Written Opinion from International Application No. PCT/US2022/015492 mailed Apr. 26, 2022.
International Search Report and Written Opinion from International Application No. PCT/US2022/015781 mailed May 6, 2022.
International Search Report and Written Opinion from International Application No. PCT/US2022/016942 mailed Jun. 8, 2022.
International Search Report and Written Opinion from International Application No. PCT/US2022/018159 mailed Dec. 12, 2022.
International Search Report and Written Opinion from International Application No. PCT/US2022/018170 mailed May 31, 2022.
International Search Report and Written Opinion from International Application No. PCT/US2022/019254 mailed Jun. 7, 2022.
International Search Report and Written Opinion from International Application No. PCT/US2022/019480 mailed Jun. 13, 2022.
International Search Report and Written Opinion from International Application No. PCT/US2022/021103 mailed Jun. 23, 2022.
International Search Report and Written Opinion from International Application No. PCT/US2022/022111 mailed Oct. 26, 2022.
International Search Report and Written Opinion from International Application No. PCT/US2022/023594 mailed Jul. 12, 2022.
International Search Report and Written Opinion from International Application No. PCT/US2022/026667 mailed Aug. 22, 2022.
International Search Report and Written Opinion from International Application No. PCT/US2022/030685 mailed Oct. 31, 2022.
International Search Report and Written Opinion from International Application No. PCT/US2022/031032 mailed Sep. 9, 2022.
International Search Report and Written Opinion from International Application No. PCT/US2022/032424 mailed Oct. 11, 2022.
International Search Report and Written Opinion from International Application No. PCT/US2022/034457 mailed Oct. 12, 2022.
International Search Report and Written Opinion from International Application No. PCT/US2022/034744 mailed Dec. 9, 2022.
International Search Report and Written Opinion from International Application No. PCT/US2022/039018 mailed Jan. 10, 2023.
International Search Report and Written Opinion from International Application No. PCT/US2022/039022 mailed Jan. 10, 2023.
International Search Report and Written Opinion from International Application No. PCT/US2022/039711 mailed Jan. 12, 2023.
International Search Report and Written Opinion from International Application No. PCT/US2022/039714 mailed Nov. 22, 2022.
International Search Report and Written Opinion from International Application No. PCT/US2022/041085 mailed Mar. 16, 2023.
International Search Report and Written Opinion from International Application No. PCT/US2022/041688 mailed Nov. 21, 2022.
International Search Report and Written Opinion from International Application No. PCT/US2022/042719 mailed Dec. 5, 2022.

(56)        References Cited

OTHER PUBLICATIONS

International Search Report and Written Opinion from International Application No. PCT/US2022/042725 mailed Dec. 19, 2022.

International Search Report and Written Opinion from International Application No. PCT/US2022/043818 mailed Mar. 24, 2023.

International Search Report and Written Opinion from International Application No. PCT/US2022/044107 mailed Dec. 23, 2022.

International Search Report and Written Opinion from International Application No. PCT/US2022/044208 mailed May 8, 2023.

International Search Report and Written Opinion from International Application No. PCT/US2022/044212 mailed Jan. 20, 2023.

International Search Report and Written Opinion from International Application No. PCT/US2022/044243 mailed Feb. 24, 2023.

International Search Report and Written Opinion from International Application No. PCT/US2022/049300 mailed Jun. 6, 2023.

International Search Report and Written Opinion from International Application No. PCT/US2022/050909 mailed Jul. 24, 2023.

International Search Report and Written Opinion from International Application No. PCT/US2023/012696 mailed Jul. 6, 2023.

International Search Report and Written Opinion from International Application No. PCT/US2023/018474 mailed Sep. 11, 2023.

International Search Report and Written Opinion from International Application No. PCT/US2023/024805 mailed Dec. 14, 2023.

Issue Notification for U.S. Appl. No. 14/952,591 mailed Jul. 28, 2021.

Issue Notification for U.S. Appl. No. 15/171,968 mailed Mar. 3, 2021.

Issue Notification for U.S. Appl. No. 15/221,106 mailed Jul. 24, 2019.

Issue Notification for U.S. Appl. No. 15/238,427 mailed Jul. 24, 2019.

Issue Notification for U.S. Appl. No. 15/260,103 mailed Aug. 7, 2019.

Issue Notification for U.S. Appl. No. 15/611,587 mailed Feb. 20, 2019.

Issue Notification for U.S. Appl. No. 15/612,325 mailed Mar. 24, 2021.

Issue Notification for U.S. Appl. No. 16/245,726 mailed Oct. 18, 2023.

Issue Notification for U.S. Appl. No. 16/899,956 mailed Mar. 29, 2023.

Issue Notification for U.S. Appl. No. 16/905,400 mailed Nov. 30, 2022.

Issue Notification for U.S. Appl. No. 17/088,272 mailed Jun. 15, 2022.

Issue Notification for U.S. Appl. No. 17/330,657 mailed Jun. 22, 2022.

Issue Notification for U.S. Appl. No. 17/461,036 mailed Oct. 11, 2023.

Issue Notification for U.S. Appl. No. 17/663,046 mailed Dec. 20, 2023.

Issue Notification for U.S. Appl. No. 29/624,661 mailed Aug. 4, 2021.

Non-Final Office Action for U.S. Appl. No. 14/947,759 mailed Mar. 17, 2016.

Non-Final Office Action for U.S. Appl. No. 14/952,591 mailed Aug. 1, 2017.

Non-Final Office Action for U.S. Appl. No. 14/952,591 mailed Mar. 20, 2020.

Non-Final Office Action for U.S. Appl. No. 14/952,591 mailed Mar. 21, 2019.

Non-Final Office Action for U.S. Appl. No. 14/952,591 mailed Sep. 28, 2018.

Non-Final Office Action for U.S. Appl. No. 15/171,968 mailed May 11, 2020.

Non-Final Office Action for U.S. Appl. No. 15/171,968 mailed Aug. 20, 2019.

Non-Final Office Action for U.S. Appl. No. 15/171,968 mailed Jun. 12, 2018.

Non-Final Office Action for U.S. Appl. No. 15/221,106 mailed Jun. 5, 2018.

Non-Final Office Action for U.S. Appl. No. 15/238,427 mailed Aug. 8, 2018.

Non-Final Office Action for U.S. Appl. No. 15/260,103 mailed Sep. 26, 2018.

Non-Final Office Action for U.S. Appl. No. 15/611,587 mailed Dec. 29, 2017.

Non-Final Office Action for U.S. Appl. No. 15/611,587 mailed Jul. 13, 2018.

Non-Final Office Action for U.S. Appl. No. 15/612,325 mailed Mar. 19, 2020.

Non-Final Office Action for U.S. Appl. No. 16/245,726 mailed Jan. 21, 2022.

Non-Final Office Action for U.S. Appl. No. 16/369,676 mailed Mar. 31, 2022.

Non-Final Office Action for U.S. Appl. No. 16/433,773 mailed Apr. 11, 2023.

Non-Final Office Action for U.S. Appl. No. 16/433,773 mailed Apr. 21, 2022.

Non-Final Office Action for U.S. Appl. No. 16/449,039 mailed Apr. 27, 2023.

Non-Final Office Action for U.S. Appl. No. 16/449,039 mailed Dec. 8, 2021.

Non-Final Office Action for U.S. Appl. No. 16/452,145 mailed Mar. 28, 2023.

Non-Final Office Action for U.S. Appl. No. 16/452,145 mailed Nov. 2, 2023.

Non-Final Office Action for U.S. Appl. No. 16/452,145 mailed Sep. 28, 2021.

Non-Final Office Action for U.S. Appl. No. 16/452,258 mailed Apr. 26, 2023.

Non-Final Office Action for U.S. Appl. No. 16/452,258 mailed Sep. 28, 2021.

Non-Final Office Action for U.S. Appl. No. 16/478,180 mailed Dec. 20, 2022.

Non-Final Office Action for U.S. Appl. No. 16/478,180 mailed Nov. 7, 2023.

Non-Final Office Action for U.S. Appl. No. 16/478,180 mailed Oct. 22, 2021.

Non-Final Office Action for U.S. Appl. No. 16/899,956 mailed Oct. 16, 2020.

Non-Final Office Action for U.S. Appl. No. 16/899,956 mailed Sep. 2, 2021.

Non-Final Office Action for U.S. Appl. No. 16/904,868 mailed Mar. 15, 2023.

Non-Final Office Action for U.S. Appl. No. 16/904,868 mailed Nov. 25, 2020.

Non-Final Office Action for U.S. Appl. No. 16/904,868 mailed Oct. 5, 2021.

Non-Final Office Action for U.S. Appl. No. 16/905,400 mailed Apr. 27, 2022.

Non-Final Office Action for U.S. Appl. No. 16/905,400 mailed Dec. 2, 2020.

Non-Final Office Action for U.S. Appl. No. 16/905,400 mailed Jul. 22, 2021.

Non-Final Office Action for U.S. Appl. No. 17/051,399 mailed Aug. 18, 2023.

Non-Final Office Action for U.S. Appl. No. 17/051,550 mailed Dec. 15, 2022.

Non-Final Office Action for U.S. Appl. No. 17/051,550 mailed Oct. 24, 2023.

Non-Final Office Action for U.S. Appl. No. 17/051,585 mailed Jan. 8, 2024.

Non-Final Office Action for U.S. Appl. No. 17/051,585 mailed Mar. 29, 2023.

Non-Final Office Action for U.S. Appl. No. 17/051,600 mailed Jan. 17, 2024.

Non-Final Office Action for U.S. Appl. No. 17/088,272 mailed Jan. 25, 2021.

Non-Final Office Action for U.S. Appl. No. 17/179,116 mailed Mar. 24, 2023.

(56) References Cited

OTHER PUBLICATIONS

Non-Final Office Action for U.S. Appl. No. 17/326,980 mailed Jul. 11, 2023.

Non-Final Office Action for U.S. Appl. No. 17/330,657 mailed Aug. 11, 2021.

Non-Final Office Action for U.S. Appl. No. 17/444,792 mailed Feb. 10, 2023.

Non-Final Office Action for U.S. Appl. No. 17/444,792 mailed Nov. 17, 2023.

Non-Final Office Action for U.S. Appl. No. 17/446,256 mailed Apr. 13, 2023.

Non-Final Office Action for U.S. Appl. No. 17/446,654 mailed Sep. 8, 2023.

Non-Final Office Action for U.S. Appl. No. 17/447,123 mailed Jan. 24, 2024.

Non-Final Office Action for U.S. Appl. No. 17/448,811 mailed Jan. 17, 2024.

Non-Final Office Action for U.S. Appl. No. 17/448,811 mailed Mar. 1, 2023.

Non-Final Office Action for U.S. Appl. No. 17/450,864 mailed May 10, 2023.

Non-Final Office Action for U.S. Appl. No. 17/451,345 mailed Dec. 7, 2022.

Non-Final Office Action for U.S. Appl. No. 17/451,345 mailed Jan. 17, 2024.

Non-Final Office Action for U.S. Appl. No. 17/451,354 mailed May 3, 2023.

Non-Final Office Action for U.S. Appl. No. 17/453,260 mailed Mar. 14, 2023.

Non-Final Office Action for U.S. Appl. No. 17/453,560 mailed Oct. 16, 2023.

Non-Final Office Action for U.S. Appl. No. 17/501,591 mailed Apr. 25, 2023.

Non-Final Office Action for U.S. Appl. No. 17/645,821 mailed Oct. 25, 2023.

Non-Final Office Action for U.S. Appl. No. 17/646,771 mailed Jul. 5, 2023.

Non-Final Office Action for U.S. Appl. No. 17/653,137 mailed Apr. 7, 2023.

Non-Final Office Action for U.S. Appl. No. 17/653,137 mailed Jan. 18, 2024.

Non-Final Office Action for U.S. Appl. No. 17/655,464 mailed Mar. 14, 2023.

Non-Final Office Action for U.S. Appl. No. 17/657,474 mailed Sep. 12, 2023.

Non-Final Office Action for U.S. Appl. No. 17/661,090 mailed Jul. 6, 2023.

Non-Final Office Action for U.S. Appl. No. 17/662,700 mailed Jul. 22, 2022.

Non-Final Office Action for U.S. Appl. No. 17/663,330 mailed Jun. 29, 2023.

Non-Final Office Action for U.S. Appl. No. 17/664,487 mailed Jun. 8, 2023.

Non-Final Office Action for U.S. Appl. No. 17/808,354 mailed Nov. 28, 2023.

Non-Final Office Action for U.S. Appl. No. 18/134,857 mailed Jan. 25, 2024.

Non-Final Office Action for U.S. Appl. No. 18/139,523 mailed Aug. 17, 2023.

Non-Final Office Action for U.S. Appl. No. 18/140,163 mailed Nov. 9, 2023.

Non-Final Office Action for U.S. Appl. No. 18/140,751 mailed Sep. 14, 2023.

Non-Final Office Action for U.S. Appl. No. 18/198,464 mailed Dec. 7, 2023.

Non-Final Office Action for U.S. Appl. No. 29/624,661 mailed Jul. 18, 2019.

Non-Final Office Action for U.S. Appl. No. 29/694,002 mailed Jun. 24, 2020.

Non-Final Office Action for U.S. Appl. No. 29/741,751 mailed Jan. 18, 2022.

Notice of Allowance for U.S. Appl. No. 14/952,591 mailed Apr. 5, 2021.

Notice of Allowance for U.S. Appl. No. 14/952,591 mailed Jul. 8, 2021.

Notice of Allowance for U.S. Appl. No. 15/171,968 mailed Feb. 16, 2021.

Notice of Allowance for U.S. Appl. No. 15/171,968 mailed Nov. 6, 2020.

Notice of Allowance for U.S. Appl. No. 15/221,106 mailed May 1, 2019.

Notice of Allowance for U.S. Appl. No. 15/238,427 mailed May 23, 2019.

Notice of Allowance for U.S. Appl. No. 15/260,103 mailed Jun. 7, 2019.

Notice of Allowance for U.S. Appl. No. 15/611,587 mailed Dec. 21, 2018.

Notice of Allowance for U.S. Appl. No. 15/612,325 mailed Feb. 19, 2021.

Notice of Allowance for U.S. Appl. No. 15/612,325 mailed Jan. 21, 2021.

Notice of Allowance for U.S. Appl. No. 16/245,726 mailed Jul. 6, 2023.

Notice of Allowance for U.S. Appl. No. 16/369,676 mailed Nov. 14, 2023.

Notice of Allowance for U.S. Appl. No. 16/449,039 mailed Dec. 15, 2022.

Notice of Allowance for U.S. Appl. No. 16/899,956 mailed Apr. 19, 2022.

Notice of Allowance for U.S. Appl. No. 16/899,956 mailed Aug. 10, 2022.

Notice of Allowance for U.S. Appl. No. 16/899,956 mailed Dec. 1, 2022.

Notice of Allowance for U.S. Appl. No. 16/899,956 mailed Dec. 29, 2021.

Notice of Allowance for U.S. Appl. No. 16/905,400 mailed Aug. 17, 2022.

Notice of Allowance for U.S. Appl. No. 17/051,554 mailed Jul. 6, 2023.

Notice of Allowance for U.S. Appl. No. 17/051,554 mailed Oct. 18, 2023.

Notice of Allowance for U.S. Appl. No. 17/088,272 mailed Aug. 5, 2021.

Notice of Allowance for U.S. Appl. No. 17/088,272 mailed Mar. 4, 2022.

Notice of Allowance for U.S. Appl. No. 17/088,272 mailed Nov. 24, 2021.

Notice of Allowance for U.S. Appl. No. 17/326,980 mailed Jan. 29, 2024.

Notice of Allowance for U.S. Appl. No. 17/330,657 mailed Mar. 16, 2022.

Notice of Allowance for U.S. Appl. No. 17/330,657 mailed Nov. 26, 2021.

Notice of Allowance for U.S. Appl. No. 17/461,036 mailed Feb. 22, 2023.

Notice of Allowance for U.S. Appl. No. 17/461,036 mailed Jun. 30, 2023.

Notice of Allowance for U.S. Appl. No. 17/461,036 mailed Oct. 6, 2022.

Notice of Allowance for U.S. Appl. No. 17/662,700 mailed Jul. 28, 2023.

Notice of Allowance for U.S. Appl. No. 17/662,700 mailed Mar. 28, 2023.

Notice of Allowance for U.S. Appl. No. 17/662,700 mailed Nov. 15, 2023.

Notice of Allowance for U.S. Appl. No. 17/663,046 mailed Jan. 30, 2023.

Notice of Allowance for U.S. Appl. No. 18/299,788 mailed Jul. 24, 2023.

Notice of Allowance for U.S. Appl. No. 18/299,788 mailed Nov. 6, 2023.

(56)　　　References Cited

OTHER PUBLICATIONS

Notice of Allowance for U.S. Appl. No. 29/624,661 mailed Apr. 28, 2021.
Notice of Allowance for U.S. Appl. No. 29/624,661 mailed Jul. 10, 2020.
Notice of Allowance for U.S. Appl. No. 29/624,661 mailed May 14, 2020.
Notice of Allowance for U.S. Appl. No. 29/624,661 mailed Sep. 29, 2020.
Notice of Allowance for U.S. Appl. No. 29/694,002 mailed Apr. 29, 2021.
Notice of Allowance for U.S. Appl. No. 29/694,002 mailed Jan. 29, 2021.
Notice of Allowance for U.S. Appl. No. 29/694,002 mailed Oct. 16, 2020.
Notice of Allowance for U.S. Appl. No. 29/741,751 mailed Jun. 9, 2022.
Notice to File Missing Parts for U.S. Appl. No. 17/179,116 mailed Mar. 3, 2021.
Restriction Requirement for U.S. Appl. No. 16/433,773 mailed Dec. 7, 2021.
Restriction Requirement for U.S. Appl. No. 16/478,180 mailed May 25, 2021.
Restriction Requirement for U.S. Appl. No. 17/051,600 mailed Sep. 21, 2023.
Restriction Requirement for U.S. Appl. No. 17/326,980 mailed Mar. 20, 2023.
Restriction Requirement for U.S. Appl. No. 17/446,256 mailed Jan. 23, 2023.
Restriction Requirement for U.S. Appl. No. 17/645,821 mailed Jul. 12, 2023.
Restriction Requirement for U.S. Appl. No. 17/646,771 mailed Apr. 6, 2023.
Restriction Requirement for U.S. Appl. No. 17/657,474 mailed Jun. 30, 2023.
Restriction Requirement for U.S. Appl. No. 18/134,857 mailed Oct. 23, 2023.
Submission in Opposition Proceedings for European Application No. 17807547.9 filed Jan. 10, 2024.
Text Messages to Lorena Eckert Re Prototype PureWick Holder dated Apr. 16, 2022.
U.S. Appl. No. 14/625,469, filed Feb. 28, 2015.
U.S. Appl. No. 14/947,759, filed Nov. 20, 2015.
U.S. Appl. No. 14/952,591, filed Nov. 25, 2015.
U.S. Appl. No. 15/171,968, filed Jun. 2, 2016.
U.S. Appl. No. 15/221,106, filed Jul. 27, 2016.
U.S. Appl. No. 15/260,103, filed Sep. 8, 2016.
U.S. Appl. No. 15/384,196, filed Dec. 19, 2016.
U.S. Appl. No. 15/612,325, filed Jun. 2, 2017.
U.S. Appl. No. 16/245,726, filed Jan. 11, 2019.
U.S. Appl. No. 16/369,676, filed Mar. 29, 2019.
U.S. Appl. No. 16/433,773, filed Jun. 6, 2019.
U.S. Appl. No. 16/449,039, filed Jun. 21, 2019.
U.S. Appl. No. 16/452,145, filed Jun. 25, 2019.
U.S. Appl. No. 16/452,258, filed Jun. 25, 2019.
U.S. Appl. No. 16/478,180, filed Jul. 16, 2019.
U.S. Appl. No. 16/904,868, filed Jun. 18, 2020.
U.S. Appl. No. 16/905,400, filed Jun. 18, 2020.
U.S. Appl. No. 17/051,550, filed Oct. 29, 2020.
U.S. Appl. No. 17/051,554, filed Oct. 29, 2020.
U.S. Appl. No. 17/051,585, filed Oct. 29, 2020.
U.S. Appl. No. 17/051,600, filed Oct. 29, 2020.
U.S. Appl. No. 17/088,272, filed Nov. 3, 2020.
U.S. Appl. No. 17/179,116, filed Feb. 18, 2021.
U.S. Appl. No. 17/330,657, filed May 26, 2021.
U.S. Appl. No. 17/378,015, filed Jul. 16, 2021.
U.S. Appl. No. 17/394,055, filed Aug. 4, 2021.
U.S. Appl. No. 17/444,825, filed Aug. 10, 2021.
U.S. Appl. No. 17/446,256, filed Aug. 27, 2021.
U.S. Appl. No. 17/446,654, filed Sep. 1, 2021.
U.S. Appl. No. 17/447,123, filed Sep. 8, 2021.
U.S. Appl. No. 17/450,864, filed Oct. 14, 2021.
U.S. Appl. No. 17/451,345, filed Oct. 19, 2021.
U.S. Appl. No. 17/451,354, filed Oct. 19, 2021.
U.S. Appl. No. 17/451,719, filed Oct. 19, 2021.
U.S. Appl. No. 17/453,260, filed Nov. 2, 2021.
U.S. Appl. No. 17/453,560, filed Nov. 4, 2021.
U.S. Appl. No. 17/461,036 mailed Aug. 30, 2021.
U.S. Appl. No. 17/501,591, filed Oct. 14, 2021.
U.S. Appl. No. 17/595,747, filed Nov. 23, 2021.
U.S. Appl. No. 17/597,408, filed Jan. 5, 2022.
U.S. Appl. No. 17/597,673, filed Jan. 18, 2022.
U.S. Appl. No. 17/614,173, filed Nov. 24, 2021.
U.S. Appl. No. 17/631,619, filed Jan. 31, 2022.
U.S. Appl. No. 17/645,821, filed Dec. 23, 2021.
U.S. Appl. No. 17/646,771, filed Jan. 3, 2022.
U.S. Appl. No. 17/653,314, filed Mar. 3, 2022.
U.S. Appl. No. 17/653,920, filed Mar. 8, 2022.
U.S. Appl. No. 17/655,464, filed Mar. 18, 2022.
U.S. Appl. No. 17/657,474, filed Mar. 31, 2022.
U.S. Appl. No. 17/661,090, filed Apr. 28, 2022.
U.S. Appl. No. 17/662,700, filed May 10, 2022.
U.S. Appl. No. 17/663,046, filed May 12, 2022.
U.S. Appl. No. 17/664,487, filed May 23, 2022.
U.S. Appl. No. 17/664,914, filed May 25, 2022.
U.S. Appl. No. 17/749,340, filed May 20, 2022.
U.S. Appl. No. 17/754,736, filed Apr. 11, 2022.
U.S. Appl. No. 17/756,201, filed May 19, 2022.
U.S. Appl. No. 17/758,152, filed Jun. 29, 2022.
U.S. Appl. No. 17/758,316, filed Jul. 1, 2022.
U.S. Appl. No. 17/759,697, filed Jul. 28, 2022.
U.S. Appl. No. 17/878,268, filed Aug. 1, 2022.
U.S. Appl. No. 17/907,125, filed Sep. 23, 2022.
U.S. Appl. No. 17/912,147, filed Sep. 16, 2022.
U.S. Appl. No. 17/929,887, filed Sep. 6, 2022.
U.S. Appl. No. 17/930,238, filed Sep. 7, 2022.
U.S. Appl. No. 17/933,590, filed Sep. 20, 2022.
U.S. Appl. No. 17/996,064, filed Oct. 12, 2022.
U.S. Appl. No. 17/996,155, filed Oct. 13, 2022.
U.S. Appl. No. 17/996,253, filed Oct. 14, 2022.
U.S. Appl. No. 17/996,468, filed Oct. 18, 2022.
U.S. Appl. No. 17/996,556, filed Oct. 19, 2022.
U.S. Appl. No. 18/003,029, filed Dec. 22, 2022.
U.S. Appl. No. 18/006,807, filed Jan. 25, 2023.
U.S. Appl. No. 18/007,105, filed Jan. 27, 2023.
U.S. Appl. No. 18/041,109, filed Feb. 9, 2023.
U.S. Appl. No. 18/042,842, filed Feb. 24, 2023.
U.S. Appl. No. 18/043,618, filed Mar. 1, 2023.
U.S. Appl. No. 18/115,444, filed Feb. 28, 2023.
U.S. Appl. No. 18/134,857, filed Apr. 14, 2023.
U.S. Appl. No. 18/140,163, filed Apr. 27, 2023.
U.S. Appl. No. 18/140,751, filed Apr. 28, 2023.
U.S. Appl. No. 18/164,800, filed Feb. 6, 2023.
U.S. Appl. No. 18/198,464, filed May 17, 2023.
U.S. Appl. No. 18/246,121, filed Mar. 21, 2023.
U.S. Appl. No. 18/247,986, filed Apr. 5, 2023.
U.S. Appl. No. 18/259,626, filed Jun. 28, 2023.
U.S. Appl. No. 18/260,122, filed Jun. 30, 2023.
U.S. Appl. No. 18/260,391, filed Jul. 5, 2023.
U.S. Appl. No. 18/260,394, filed Jul. 5, 2023.
U.S. Appl. No. 18/263,800, filed Aug. 1, 2023.
U.S. Appl. No. 18/264,004, filed Aug. 2, 2023.
U.S. Appl. No. 18/265,736, filed Jun. 7, 2023.
U.S. Appl. No. 18/299,788, filed Apr. 13, 2023.
U.S. Appl. No. 18/335,579, filed Jun. 15, 2023.
U.S. Appl. No. 18/373,424, filed Sep. 27, 2023.
U.S. Appl. No. 18/376,274, filed Oct. 3, 2023.
U.S. Appl. No. 18/389,009, filed Nov. 13, 2023.
U.S. Appl. No. 18/415,080, filed Jan. 17, 2024.
U.S. Appl. No. 18/426,795, filed Jan. 30, 2024.
U.S. Appl. No. 18/548,152, filed Aug. 28, 2023.
U.S. Appl. No. 18/549,387, filed Sep. 7, 2023.
U.S. Appl. No. 18/549,658, filed Sep. 8, 2023.

(56)　　　References Cited

OTHER PUBLICATIONS

U.S. Appl. No. 18/553,625, filed Oct. 2, 2023.
U.S. Appl. No. 18/556,945, filed Oct. 24, 2023.
U.S. Appl. No. 18/558,502, filed Nov. 1, 2023.
U.S. Appl. No. 18/562,626, filed Nov. 20, 2023.
U.S. Appl. No. 18/563,672, filed Nov. 22, 2023.
U.S. Appl. No. 18/569,711, filed Dec. 13, 2023.
U.S. Appl. No. 18/569,778, filed Dec. 13, 2023.
U.S. Appl. No. 29/741,751, filed Jul. 15, 2020.
U.S. Appl. No. 61/955,537, filed Mar. 19, 2014.
U.S. Appl. No. 62/082,279, filed Nov. 20, 2014.
U.S. Appl. No. 62/084,078, filed Nov. 25, 2014.
U.S. Appl. No. 62/414,963, filed Oct. 31, 2016.
U.S. Appl. No. 62/452,437, filed Jan. 31, 2017.
U.S. Appl. No. 62/485,578, filed Apr. 14, 2017.
U.S. Appl. No. 62/665,297, filed May 1, 2018.
U.S. Appl. No. 62/665,302, filed May 1, 2018.
U.S. Appl. No. 62/665,317, filed May 1, 2018.
U.S. Appl. No. 62/665,321, filed May 1, 2018.
U.S. Appl. No. 62/665,331, filed May 1, 2018.
U.S. Appl. No. 62/665,335, filed May 1, 2018.
U.S. Appl. No. 62/853,279, filed May 28, 2019.
U.S. Appl. No. 62/853,889, filed May 29, 2019.
U.S. Appl. No. 62/864,656, filed Jun. 21, 2019.
U.S. Appl. No. 62/873,045, filed Jul. 11, 2019.
U.S. Appl. No. 62/873,048, filed Jul. 11, 2019.
U.S. Appl. No. 62/876,500, filed Jul. 19, 2019.
U.S. Appl. No. 62/877,558, filed Jul. 23, 2019.
U.S. Appl. No. 62/883,172, filed Aug. 6, 2019.
U.S. Appl. No. 62/889,149, filed Aug. 20, 2019.
U.S. Appl. No. 62/923,279, filed Oct. 18, 2019.
U.S. Appl. No. 62/926,767, filed Oct. 28, 2019.
U.S. Appl. No. 62/935,337, filed Nov. 14, 2019.
U.S. Appl. No. 62/938,447, filed Nov. 21, 2019.
U.S. Appl. No. 62/949,187, filed Dec. 17, 2019.
U.S. Appl. No. 62/956,756, filed Jan. 3, 2020.
U.S. Appl. No. 62/956,767, filed Jan. 3, 2020.
U.S. Appl. No. 62/956,770, filed Jan. 3, 2020.
U.S. Appl. No. 62/967,158, filed Jan. 26, 2020.
U.S. Appl. No. 62/967,977, filed Jan. 30, 2020.
U.S. Appl. No. 62/991,754, filed Mar. 19, 2020.
U.S. Appl. No. 62/994,912, filed Mar. 26, 2020.
U.S. Appl. No. 63/008,112, filed Apr. 10, 2020.
U.S. Appl. No. 63/011,445, filed Apr. 17, 2020.
U.S. Appl. No. 63/011,487, filed Apr. 17, 2020.
U.S. Appl. No. 63/011,571, filed Apr. 17, 2020.
U.S. Appl. No. 63/011,657, filed Apr. 17, 2020.
U.S. Appl. No. 63/011,760, filed Apr. 17, 2020.
U.S. Appl. No. 63/012,347, filed Apr. 20, 2020.
U.S. Appl. No. 63/012,384, filed Apr. 20, 2020.
U.S. Appl. No. 63/030,685, filed May 27, 2020.
U.S. Appl. No. 63/047,374, filed Jul. 2, 2020.
U.S. Appl. No. 63/061,241, filed Aug. 5, 2020.
U.S. Appl. No. 63/061,244, filed Aug. 5, 2020.
U.S. Appl. No. 63/061,834, filed Aug. 6, 2020.
U.S. Appl. No. 63/064,017, filed Aug. 11, 2020.
U.S. Appl. No. 63/064,126, filed Aug. 11, 2020.
U.S. Appl. No. 63/067,542, filed Aug. 19, 2020.
U.S. Appl. No. 63/071,438, filed Aug. 28, 2020.
U.S. Appl. No. 63/073,545, filed Sep. 2, 2020.
U.S. Appl. No. 63/073,553, filed Sep. 2, 2020.
U.S. Appl. No. 63/074,051, filed Sep. 3, 2020.
U.S. Appl. No. 63/074,066, filed Sep. 3, 2020.
U.S. Appl. No. 63/076,032, filed Sep. 9, 2020.
U.S. Appl. No. 63/076,474, filed Sep. 10, 2020.
U.S. Appl. No. 63/076,477, filed Sep. 10, 2020.
U.S. Appl. No. 63/082,261, filed Sep. 23, 2020.
U.S. Appl. No. 63/088,506, filed Oct. 7, 2020.
U.S. Appl. No. 63/088,511, filed Oct. 7, 2020.
U.S. Appl. No. 63/094,464, filed Oct. 21, 2020.

U.S. Appl. No. 63/094,498, filed Oct. 21, 2020.
U.S. Appl. No. 63/094,594, filed Oct. 21, 2020.
U.S. Appl. No. 63/094,608, filed Oct. 21, 2020.
U.S. Appl. No. 63/094,626, filed Oct. 21, 2020.
U.S. Appl. No. 63/094,646, filed Oct. 21, 2020.
U.S. Appl. No. 63/109,066, filed Nov. 3, 2020.
U.S. Appl. No. 63/109,084, filed Nov. 3, 2020.
U.S. Appl. No. 63/112,417, filed Nov. 11, 2020.
U.S. Appl. No. 63/119,161, filed Nov. 30, 2020.
U.S. Appl. No. 63/124,271, filed Dec. 11, 2020.
U.S. Appl. No. 63/133,892, filed Jan. 5, 2021.
U.S. Appl. No. 63/134,287, filed Jan. 6, 2021.
U.S. Appl. No. 63/134,450, filed Jan. 6, 2021.
U.S. Appl. No. 63/134,631, filed Jan. 7, 2021.
U.S. Appl. No. 63/134,632, filed Jan. 7, 2021.
U.S. Appl. No. 63/134,754, filed Jan. 7, 2021.
U.S. Appl. No. 63/138,878, filed Jan. 19, 2021.
U.S. Appl. No. 63/146,946, filed Feb. 8, 2021.
U.S. Appl. No. 63/147,013, filed Feb. 8, 2021.
U.S. Appl. No. 63/147,299, filed Feb. 9, 2021.
U.S. Appl. No. 63/148,723, filed Feb. 12, 2021.
U.S. Appl. No. 63/150,640, filed Feb. 18, 2021.
U.S. Appl. No. 63/154,248, filed Feb. 26, 2021.
U.S. Appl. No. 63/155,395, filed Mar. 2, 2021.
U.S. Appl. No. 63/157,007, filed Mar. 5, 2021.
U.S. Appl. No. 63/157,014, filed Mar. 5, 2021.
U.S. Appl. No. 63/159,142, filed Mar. 10, 2021.
U.S. Appl. No. 63/159,186, filed Mar. 10, 2021.
U.S. Appl. No. 63/159,210, filed Mar. 10, 2021.
U.S. Appl. No. 63/165,273, filed Mar. 24, 2021.
U.S. Appl. No. 63/165,384, filed Mar. 24, 2021.
U.S. Appl. No. 63/171,165, filed Apr. 6, 2021.
U.S. Appl. No. 63/172,975, filed Apr. 9, 2021.
U.S. Appl. No. 63/181,695, filed Apr. 29, 2021.
U.S. Appl. No. 63/191,558, filed May 21, 2021.
U.S. Appl. No. 63/192,274, filed May 24, 2021.
U.S. Appl. No. 63/192,289, filed May 24, 2021.
U.S. Appl. No. 63/193,235, filed May 26, 2021.
U.S. Appl. No. 63/193,406, filed May 26, 2021.
U.S. Appl. No. 63/193,891, filed May 27, 2021.
U.S. Appl. No. 63/208,262, filed Jun. 8, 2021.
U.S. Appl. No. 63/214,551, filed Jun. 24, 2021.
U.S. Appl. No. 63/214,570, filed Jun. 24, 2021.
U.S. Appl. No. 63/215,017, filed Jun. 25, 2021.
U.S. Appl. No. 63/228,244, filed Aug. 2, 2021.
U.S. Appl. No. 63/228,252, filed Aug. 2, 2021.
U.S. Appl. No. 63/228,258, filed Aug. 2, 2021.
U.S. Appl. No. 63/230,894, filed Aug. 9, 2021.
U.S. Appl. No. 63/230,897, filed Aug. 9, 2021.
U.S. Appl. No. 63/238,457, filed Aug. 30, 2021.
U.S. Appl. No. 63/238,477, filed Aug. 30, 2021.
U.S. Appl. No. 63/241,328, filed Sep. 7, 2021.
U.S. Appl. No. 63/241,562, filed Sep. 8, 2021.
U.S. Appl. No. 63/241,564, filed Sep. 8, 2021.
U.S. Appl. No. 63/241,575, filed Sep. 8, 2021.
U.S. Appl. No. 63/246,972, filed Sep. 22, 2021.
U.S. Appl. No. 63/247,375, filed Sep. 23, 2021.
U.S. Appl. No. 63/247,478, filed Sep. 23, 2021.
U.S. Appl. No. 63/247,491, filed Sep. 23, 2021.
U.S. Appl. No. 63/299,208, filed Jan. 13, 2022.
U.S. Appl. No. 63/308,190, filed Feb. 9, 2022.
U.S. Appl. No. 63/596,012, filed Nov. 3, 2023.
U.S. Appl. No. 63/608,553, filed Dec. 11, 2023.
Defendant and Counterclaim Plaintiff Sage Products, LLC's Answer, Defenses, and Counterclaims to Plaintiff's Amended Complaint, Nov. 1, 2019.
*PureWick Corporation* v. *Sage Products*, LLC Transcripts vol. 2, Mar. 29, 2022.
*PureWick Corporation* v. *Sage Products*, LLC Transcripts vol. 3, Mar. 30, 2022.
*PureWick Corporation* v. *Sage Products*, LLC Transcripts vol. 4, Mar. 31, 2022.
Memorandum Order, Feb. 2021.

(56) References Cited

OTHER PUBLICATIONS

Sage's Initial Invalidity Contentions Regarding U.S. Pat. Nos. 8,287,508; 10,226,375; and 10,390,989, May 29, 2020.
Sage's Supplemental and Initial Invalidity Contentions Regarding U.S. Pat. Nos. 8,287,508; 10,226,375; 10,390,989 and Initial Invalidity Contentions Regarding U.S. Pat. No. 10,376,407, Aug. 21, 2020.
Sage's Second Supplemental Invalidity Contentions Regarding U.S. Appl. Nos. 8,287,508, 10,226,375, 10,390,989, and 10,376,407.
Boehringer CareDry System—Second Generation for Non-Invasive Urinary Management for Females, Mar. 2021.
*PureWick Corporation* v. *Sage Products*, LLC Transcripts vol. 5, Apr. 1, 2022.
Excerpts from the 508 (U.S. Pat. No. 8,278,508) Patent's Prosecution History, 2020.
*PureWick Corporation* v. *Sage Products*, LLC Transcripts vol. 1, Mar. 28, 2022.
Plaintiff's Opening Claim Construction Brief, Oct. 16, 2020.
Plaintiff's Identification of Claim Terms and Proposed Constructions.
PureWick's Response to Interrogatory No. 9 in *PureWick, LLC* v. *Sage Products, LLC*, Mar. 23, 2020.
Sage's Preliminary Identification of Claim Elements and Proposed Constructions for U.S. Pat. Nos. 8,287,508, 10,226,376, 10,390,989 and 10,376,407.
Decision Granting Institution of Inter Partes Review for U.S. Pat. No. 8,287,508, Feb. 17, 2021.
Corrected Certificate of Service, 2020.
Declaration of Diane K. Newman Curriculum Vitae, 2020.
"3 Devices Take Top Honors in Dare-To-Dream Medtech Design Contest", R+D Digest, Nov. 2013, 1 page.
"Advanced Mission Extender Device (AMDX) Products", Omni Medical Systems, Inc., 15 pages.
"AMXD Control Starter Kit", Omni Medical Systems, Inc., 1 page.
"AMXD Control Starter Kit Brochure", https://www.omnimedicalsys.com/index.php?page=products, 8 pages.
"AMXDmax Advanced Mission Extender Device User & Maintenance Guide", Omni Medical, Jan. 11, 2010, 10 pages.
"AMXDmax Development History 2002-2014", Omni Medical Systems, Inc., 2 pages.
"AMXDmax In-Flight Bladder Relief", Omni Medical; Omni Medical Systems, Inc., 2015.
"AMXDX—Advanced Mission Extender Device Brochure", Omni Medical, 2 pages.
"Combat Force Multiplier in Flight Bladder Relief Cockpit Essential Equipment Brochure", Omni Medical, 20 pages.
"External Urine Management for Female Anatomy", https://www.stryker.com/us/en/sage/products/sage-primafit.html, Jul. 2020, 4 pages.
"GSA Price List", Omni Medical, Apr. 2011, 2 pages.
"High Absorbancy Cellulose Acetate Electrospun Nanofibers for Feminine Hygiene Application" https://www.sciencedirect.com/science/article/abs/pii/S2352940716300701?via%3Dihub , Jul. 2016, 3 pages.
"How is Polypropylene Fiber Made", https:www.yarnsandfibers.com/textile-resources/synthetic-fibers/polypropylene-fiber/polypropylene-fiber-production-raw-materials/how-is-polypropylene-fiber-made/ last accessed 2020 , Oct. 7, 2020, 3 pages.
"How Period Panties Work", www.shethinx.com/pages/thinx-itworks, 2020, 10 pages.
"Hydrogel properties of electrospun polyvinylpyrrolidone and polyvinylpyrrolidone/poly(acrylic acid) blend nanofibers", https://pubs.rsc.org/en/content/articlelanding/2015/ra/c5ra07514a#!divAbstract, 2015, 5 pages.
"In Flight Bladder Relief", Omni Medical, 14 pages.
"Letter to Mark Harvie of Omni Measurement Systems", Department of Veterans Affairs, Nov. 1, 2007, 11 pages.
"Making Women's Sanitary Products Safer and Cheaper", https://www.elsevier.com/connect/making-womens-sanitary-products-safer-and-cheaper, Sep. 2016, 10 pages.

"Novel Nanofibers Make Safe and Effective Absorbent for Sanitary Products", https://www.materialstoday.com/nanomaterials/news/nanofibers-make-safe-and-effective-absorbent/, Oct. 2016, 3 pages.
"Research and Development Work Relating to Assistive Technology Jun. 2005", British Department of Health, Nov. 2006, 40 pages.
"Revised AMXDmax Advanced Mission Extender Device User & Maintenance Guide", Omni Medical Systems, Oct. 8, 2019, 52 pages.
"Rising Warrior Insulated Gallon Jug Cover", https://www.amazon.com/Rising-Warrior-Insulated-Sleeve, 2021, 2 pages.
"Step by Step How Ur24 WorksHome", http://medicalpatentur24.com, Aug. 30, 2017, 4 pages.
"Underwear that absorbs your period", Thinx!, 7 pages.
"Urine Bag Cover-Catheter Bag Cover 2000 ml Volume-Medline Style-Multiple Sclerosis-Spine Injury-Suprapublic Catheter-Bladder Incontinence", https://www.etsy.com/listing/1142934658/urine-bag-cover-caatheter-bag-cover-2000, 2022, 1 page.
"User & Maintenance Guide", Omni Medical, 2007, 16 pages.
"Vinyl Dust Cover, Janome #741811000, Janome, Sewing Parts Online", https://www.sewingpartsonline.com/vinyl-dust-cover-janome-74181000, 2020, 2 pages.
"Winners Announced for Dare-to-Dream Medtech Design Challenge", https://www.mddionline.com/design-engineering/winners-announced-dare-dream-medtech-design-challenge, 2014, 4 pages.
Ali, "Sustainability Assessment: Seventh Generation Diapers versus gDiapers", The University of Vermont, Dec. 6, 2011, pp. 1-31.
Autumn, et al., "Frictional adhesion: a new angle on gecko attachment", The Journal of Experimental Biology, 2006, pp. 3569-3579.
Cañas, et al., "Effect of nano- and micro-roughness on adhesion of bioinspired micropatterned surfaces", Acta Biomaterialia 8, 2012, pp. 282-288.
Chaudhary, et al., "Bioinspired dry adhesive: Poly(dimethylsiloxane) grafted with poly(2-ethylhexyl acrylate) brushes", European Polymer Journal, 2015, pp. 432-440.
Dai, et al., "Non-sticky and Non-slippery Biomimetic Patterned Surfaces", Journal of Bionic Engineering, Mar. 2020, pp. 326-334.
Espinoza-Ramirez, "Nanobiodiversity and Biomimetic Adhesives Development: From Nature to Production and Application", Journal of Biomaterials and Nanobiotechnology, pp. 78-101,2019.
Hollister, "Female Urinary and Pouch and Male Urinary Pouch Brochure", www.hollister.com, 2011, 1 page.
Hollister, "Male Urinary Pouch External Collection Device", http://www.hollister.com/en/products/Continence-Care-Products/Urine-Collectors/Urine-Collection-Accessories/Male-Urinary-Pouch-External-Collection-Device.
Hollister, "Retracted Penis Pouch by Hollister", Vitality Medical.com.
Hwang, et al., "Multifunctional Smart Skin Adhesive Patches for Advanced Health Care", Adv. Healthcare Mater, 2018, pp. 1-20.
Jagota, et al., "Adhesion, friction, and compliance of bio-mimetic and bio-inspired structured interfaces", Materials Science and Engineering, 2011, pp. 253-292.
Jeong, et al., "A nontransferring dry adhesive with hierarchical polymer nanohairs", PNAS, Apr. 7, 2009, pp. 5639-5644.
Jeong, et al., "Nanohairs and nanotubes: Efficient structural elements for gecko-inspired artificial dry adhesives", Science Direct , 2009, pp. 335-346.
Karp, et al., "Dry solution to a sticky problem", Nature., 2011, pp. 42-43.
Lee, et al., "Continuous Fabrication of Wide-Tip Microstructures for Bio-Inspired Dry Adhesives via Tip Inking Process", Journal of Chemistry, Jan. 2, 2019, pp. 1-5.
Macaulay, et al., "A Noninvasive Continence Management System: Development and Evaluation of a Novel Toileting Device for Women", The Wound, Ostomy and Continence Nurses Society, 2007, pp. 641-648.
Merriam-Webster Dictionary, "Embed Definition & Meaning", https://www.merriam-webster.com/dictionary/embed last accessed Aug. 3, 2023, 2003.
Newman, et al., "The Urinary Incontinence Sourcebook", Petition for Interparties Review, 1997, 23 pages.

(56)                  References Cited

OTHER PUBLICATIONS

Newton, et al., "Measuring Safety, Effectiveness and Ease of Use of PureWick in the Management of Urinary Incontinence in Bedbound Women: Case Studies", 11 pages.
Parmar, "10 Finalists Chosen for Dare-to-Dream Medtech Design Challenge (PureWick)", Design Services, Nov. 10, 2014, 3 pages.
Parness, et al., "A microfabricated wedge-shaped adhesive array displaying gecko-like dynamic adhesion, directionality", J.R. Soc. Interface, 2009, pp. 1223-1232.
Pieper, et al., "An external urine-collection device for women: A clinical trial", Journal of ER Nursing, vol. 20, No. 2, Mar./Apr. 1993, pp. 51-55.
Purewick, "Incontinence Relief for Women", Presentation, Sep. 23, 2015, 7 pages.
Pytlik, "Super Absorbent Polymers", University of Buffalo.
Sachtman, "New Relief for Pilots? It Depends", Wired, 2008, 2 pages.
Tsipenyuk, et al., "Use of biomimetic hexagonal surface texture in friction against lubricated skin", Journal of the Royal Society—Interface, 2014, pp. 1-6.
Vinas, "A Solution for an Awkward—But Serious—Subject", http://www.aero-news.net/index.cfm?do=main.textpost&id=69ae2bb1-838b-4098-a7b5-7flbb2505688 last accessed Feb. 8, 2021.
Wikipedia Article, "Zylinder (Geometrie)", https://de.wikipedia.org/w/index.php?title=Zylinder (Geometrie)&oldid=154862081, version of Jun. 1, 2016, 7 pages.
Advisory Action for U.S. Appl. No. 17/051,585 mailed Oct. 8, 2024.
Advisory Action for U.S. Appl. No. 17/446,256 mailed Nov. 19, 2024.
Advisory Action for U.S. Appl. No. 17/597,673 mailed Jan. 7, 2025.
Advisory Action for U.S. Appl. No. 17/653,137 mailed Nov. 20, 2024.
Advisory Action for U.S. Appl. No. 17/653,920 mailed Oct. 28, 2024.
Advisory Action for U.S. Appl. No. 18/003,029 mailed Jan. 8, 2025.
Advisory Action for U.S. Appl. No. 18/134,857 mailed Oct. 23, 2024.
Advisory Action for U.S. Appl. No. 18/164,800 mailed Jan. 8, 2025.
Corrected Notice of Allowability for U.S. Appl. No. 17/450,864 mailed Oct. 24, 2024.
Corrected Notice of Allowability for U.S. Appl. No. 17/501,591 mailed Aug. 9, 2024.
Corrected Notice of Allowability for U.S. Appl. No. 17/646,771 mailed Jan. 17, 2025.
Corrected Notice of Allowability for U.S. Appl. No. 17/664,914 mailed Aug. 9, 2024.
Corrected Notice of Allowability for U.S. Appl. No. 18/426,795 mailed Dec. 4, 2024.
Final Office Action for U.S. Appl. No. 16/433,773 mailed Sep. 9, 2024.
Final Office Action for U.S. Appl. No. 16/452,258 mailed Jan. 6, 2025.
Final Office Action for U.S. Appl. No. 17/446,256 mailed Aug. 7, 2024.
Final Office Action for U.S. Appl. No. 17/446,654 mailed Dec. 18, 2024.
Final Office Action for U.S. Appl. No. 17/451,345 mailed Feb. 6, 2025.
Final Office Action for U.S. Appl. No. 17/451,354 mailed Oct. 28, 2024.
Final Office Action for U.S. Appl. No. 17/595,747 mailed Dec. 12, 2024.
Final Office Action for U.S. Appl. No. 17/597,673 mailed Oct. 22, 2024.
Final Office Action for U.S. Appl. No. 17/625,941 mailed Feb. 18, 2025.
Final Office Action for U.S. Appl. No. 17/653,137 mailed Aug. 7, 2024.
Final Office Action for U.S. Appl. No. 17/653,314 mailed Jan. 30, 2025.
Final Office Action for U.S. Appl. No. 17/653,920 mailed Aug. 14, 2024.
Final Office Action for U.S. Appl. No. 17/655,464 mailed Nov. 29, 2024.
Final Office Action for U.S. Appl. No. 17/664,487 mailed Jan. 13, 2025.
Final Office Action for U.S. Appl. No. 18/003,029 mailed Oct. 22, 2024.
Final Office Action for U.S. Appl. No. 18/134,857 mailed Jul. 25, 2024.
Final Office Action for U.S. Appl. No. 18/164,800 mailed Oct. 22, 2024.
International Search Report and Written Opinion from International Application No. PCT/US2023/031432 mailed Feb. 29, 2024.
International Search Report and Written Opinion from International Application No. PCT/US2023/036238 mailed Jul. 22, 2024.
International Search Report and Written Opinion from International Application No. PCT/US2023/077168 mailed Jun. 24, 2024.
International Search Report and Written Opinion from International Application No. PCT/US2023/080680 mailed Jul. 22, 2024.
International Search Report and Written Opinion from International Application No. PCT/US2023/085516 mailed Aug. 26, 2024.
International Search Report and Written Opinion from International Application No. PCT/US2024/053681 mailed Jan. 27, 2025.
Issue Notification for U.S. Appl. No. 16/369,676 mailed Oct. 2, 2024.
Issue Notification for U.S. Appl. No. 16/452,145 mailed Oct. 23, 2024.
Issue Notification for U.S. Appl. No. 17/179,116 mailed Dec. 25, 2024.
Issue Notification for U.S. Appl. No. 17/447,123 mailed Nov. 13, 2024.
Issue Notification for U.S. Appl. No. 17/450,864 mailed Jan. 8, 2025.
Issue Notification for U.S. Appl. No. 17/453,560 mailed Aug. 7, 2024.
Issue Notification for U.S. Appl. No. 17/529,769 mailed Feb. 19, 2025.
Issue Notification for U.S. Appl. No. 17/661,090 mailed Feb. 5, 2025.
Issue Notification for U.S. Appl. No. 17/662,700 mailed Oct. 23, 2024.
Issue Notification for U.S. Appl. No. 17/664,914 mailed Nov. 6, 2024.
Issue Notification for U.S. Appl. No. 17/667,097 mailed Dec. 11, 2024.
Issue Notification for U.S. Appl. No. 18/140,163 mailed Dec. 4, 2024.
Issue Notification for U.S. Appl. No. 18/140,751 mailed Feb. 12, 2025.
Issue Notification for U.S. Appl. No. 18/198,464 mailed Nov. 20, 2024.
Issue Notification for U.S. Appl. No. 18/389,009 mailed Dec. 18, 2024.
Issue Notification for U.S. Appl. No. 18/426,795 mailed Feb. 19, 2025.
Non-Final Office Action for U.S. Appl. No. 16/478,180 mailed Aug. 7, 2024.
Non-Final Office Action for U.S. Appl. No. 17/444,792 mailed Oct. 30, 2024.
Non-Final Office Action for U.S. Appl. No. 17/446,256 mailed Dec. 13, 2024.
Non-Final Office Action for U.S. Appl. No. 17/451,345 mailed Jul. 25, 2024.
Non-Final Office Action for U.S. Appl. No. 17/597,408 mailed Aug. 15, 2024.
Non-Final Office Action for U.S. Appl. No. 17/614,173 mailed Sep. 24, 2024.
Non-Final Office Action for U.S. Appl. No. 17/625,941 mailed Nov. 4, 2024.
Non-Final Office Action for U.S. Appl. No. 17/628,411 mailed Sep. 23, 2024.

(56) References Cited

OTHER PUBLICATIONS

Non-Final Office Action for U.S. Appl. No. 17/645,821 mailed Sep. 6, 2024.
Non-Final Office Action for U.S. Appl. No. 17/653,137 mailed Jan. 28, 2025.
Non-Final Office Action for U.S. Appl. No. 17/653,314 mailed Aug. 29, 2024.
Non-Final Office Action for U.S. Appl. No. 17/653,920 mailed Nov. 27, 2024.
Non-Final Office Action for U.S. Appl. No. 17/749,340 mailed Aug. 14, 2024.
Non-Final Office Action for U.S. Appl. No. 17/757,311 mailed Oct. 22, 2024.
Non-Final Office Action for U.S. Appl. No. 17/758,316 mailed Aug. 28, 2024.
Non-Final Office Action for U.S. Appl. No. 17/759,697 mailed Dec. 4, 2024.
Non-Final Office Action for U.S. Appl. No. 17/808,354 mailed Dec. 13, 2024.
Non-Final Office Action for U.S. Appl. No. 17/907,125 mailed Dec. 13, 2024.
Non-Final Office Action for U.S. Appl. No. 18/139,523 mailed Aug. 26, 2024.
Non-Final Office Action for U.S. Appl. No. 18/426,795 mailed Aug. 9, 2024.
Non-Final Office Action for U.S. Appl. No. 18/451,080 mailed Jul. 30, 2024.
Non-Final Office Action for U.S. Appl. No. 18/584,002 mailed Sep. 19, 2024.
Notice of Allowance for U.S. Appl. No. 16/478,180 mailed Dec. 16, 2024.
Notice of Allowance for U.S. Appl. No. 16/904,868 mailed Jan. 21, 2025.
Notice of Allowance for U.S. Appl. No. 16/904,868 mailed Sep. 29, 2024.
Notice of Allowance for U.S. Appl. No. 17/051,585 mailed Dec. 26, 2024.
Notice of Allowance for U.S. Appl. No. 17/179,116 mailed Sep. 13, 2024.
Notice of Allowance for U.S. Appl. No. 17/447,123 mailed Jul. 26, 2024.
Notice of Allowance for U.S. Appl. No. 17/450,864 mailed Sep. 18, 2024.
Notice of Allowance for U.S. Appl. No. 17/501,591 mailed Jul. 31, 2024.
Notice of Allowance for U.S. Appl. No. 17/501,591 mailed Nov. 20, 2024.
Notice of Allowance for U.S. Appl. No. 17/527,769 mailed Nov. 20, 2024.
Notice of Allowance for U.S. Appl. No. 17/596,629 mailed Jan. 29, 2025.
Notice of Allowance for U.S. Appl. No. 17/646,771 mailed Dec. 17, 2024.
Notice of Allowance for U.S. Appl. No. 17/661,090 mailed Oct. 30, 2024.
Notice of Allowance for U.S. Appl. No. 17/663,330 mailed Nov. 20, 2024.
Notice of Allowance for U.S. Appl. No. 17/664,914 mailed Jul. 26, 2024.
Notice of Allowance for U.S. Appl. No. 17/667,097 mailed Aug. 28, 2024.
Notice of Allowance for U.S. Appl. No. 17/749,340 mailed Feb. 14, 2025.
Notice of Allowance for U.S. Appl. No. 18/134,857 mailed Feb. 20, 2025.
Notice of Allowance for U.S. Appl. No. 18/140,163 mailed Aug. 21, 2024.
Notice of Allowance for U.S. Appl. No. 18/140,751 mailed Nov. 1, 2024.
Notice of Allowance for U.S. Appl. No. 18/198,464 mailed Jul. 30, 2024.
Notice of Allowance for U.S. Appl. No. 18/389,009 mailed Aug. 28, 2024.
Notice of Allowance for U.S. Appl. No. 18/415,080 mailed Dec. 30, 2024.
Notice of Allowance for U.S. Appl. No. 18/426,795 mailed Nov. 20, 2024.
Notice of Allowance for U.S. Appl. No. 18/584,002 mailed Jan. 8, 2025.
Restriction Requirement for U.S. Appl. No. 17/596,629 mailed Sep. 19, 2024.
Restriction Requirement for U.S. Appl. No. 17/625,941 mailed Aug. 7, 2024.
Restriction Requirement for U.S. Appl. No. 17/754,736 mailed Nov. 20, 2024.
Restriction Requirement for U.S. Appl. No. 17/756,201 mailed Oct. 4, 2024.
Restriction Requirement for U.S. Appl. No. 17/758,152 mailed Nov. 5, 2024.
Restriction Requirement for U.S. Appl. No. 17/809,083 mailed Dec. 31, 2024.
Restriction Requirement for U.S. Appl. No. 17/878,268 mailed Sep. 20, 2024.
U.S. Appl. No. 15/611,587, filed Jun. 1, 2017.
U.S. Appl. No. 17/013,822, filed Sep. 7, 2020.
U.S. Appl. No. 18/828,559, filed Sep. 9, 2024.
U.S. Appl. No. 18/834,115, filed Jul. 29, 2024.
U.S. Appl. No. 18/834,176, filed Jul. 29, 2024.
U.S. Appl. No. 18/834,340, filed Jul. 30, 2024.
U.S. Appl. No. 18/835,068, filed Aug. 1, 2024.
U.S. Appl. No. 18/835,444, filed Aug. 2, 2024.
U.S. Appl. No. 18/836,204, filed Aug. 6, 2024.
U.S. Appl. No. 18/841,630, filed Aug. 26, 2024.
U.S. Appl. No. 18/851,197, filed Sep. 26, 2024.
U.S. Appl. No. 18/886,306, filed Sep. 16, 2024.
U.S. Appl. No. 18/903,592, filed Oct. 1, 2024.
U.S. Appl. No. 18/925,921, filed Oct. 24, 2024.
U.S. Appl. No. 18/930,014, filed Oct. 29, 2024.
U.S. Appl. No. 18/931,853, filed Oct. 30, 2024.
U.S. Appl. No. 18/951,944, filed Nov. 19, 2024.
U.S. Appl. No. 18/957,011, filed Nov. 22, 2024.
U.S. Appl. No. 18/974,367, filed Dec. 9, 2024.
U.S. Appl. No. 18/982,930, filed Dec. 16, 2024.
U.S. Appl. No. 19/038,774, filed Jan. 28, 2025.
U.S. Appl. No. 19/039,165, filed Jan. 28, 2025.
U.S. Appl. No. 19/046,047, filed Feb. 5, 2025.
U.S. Appl. No. 19/047,728, filed Feb. 7, 2025.
U.S. Appl. No. 19/048,004, filed Feb. 7, 2025.
U.S. Appl. No. 19/049,501, filed Feb. 10, 2025.
U.S. Appl. No. 19/049,783, filed Feb. 10, 2025.
U.S. Appl. No. 19/058,726, filed Feb. 20, 2025.
U.S. Appl. No. 19/103,165, filed Feb. 11, 2025.
U.S. Appl. No. 63/564,696, filed Mar. 13, 2024.
U.S. Appl. No. 63/181,709, filed Apr. 29, 2021.
U.S. Appl. No. 63/568,615, filed Mar. 22, 2024.
U.S. Appl. No. 63/683,428, filed Aug. 15, 2024.
U.S. Appl. No. 63/711,438, filed Oct. 24, 2024.
U.S. Appl. No. 63/711,445, filed Oct. 24, 2024.
U.S. Appl. No. 63/720,004, filed Nov. 13, 2024.
"Dictionary.com, ABUT Definition and Meaning", Dictionary.com, https://www.dictionary.com/browse/abut, 2024, 1 page.
"Surface Energy Data for Cellulose acetate, CAS # 9004-35-7", Diviersified Enterprises, 2009, 1 page.
"TUBE Definition & Meaning" Merriam Webster Dictionary, 2025, <https://www.merriam-webster.com/dictionary/tube>.
Advisory Action for U.S. Appl. No. 16/452,258 mailed May 5, 2025.
Advisory Action for U.S. Appl. No. 17/378,015 mailed Oct. 28, 2025.
Advisory Action for U.S. Appl. No. 17/394,055 mailed Jan. 9, 2026.
Advisory Action for U.S. Appl. No. 17/446,256 mailed Nov. 6, 2025.

(56) References Cited

OTHER PUBLICATIONS

Advisory Action for U.S. Appl. No. 17/446,654 mailed Feb. 28, 2025.

Advisory Action for U.S. Appl. No. 17/451,345 mailed May 13, 2025.

Advisory Action for U.S. Appl. No. 17/595,747 mailed Mar. 17, 2025.

Advisory Action for U.S. Appl. No. 17/653,314 mailed Apr. 8, 2025.

Advisory Action for U.S. Appl. No. 17/655,464 mailed Feb. 25, 2025.

Advisory Action for U.S. Appl. No. 17/664,487 mailed Apr. 24, 2025.

Advisory Action for U.S. Appl. No. 17/757,311 mailed Jul. 2, 2025.

Corrected Notice of Allowability for U.S. Appl. No. 17/444,792 mailed Jun. 24, 2025.

Corrected Notice of Allowability for U.S. Appl. No. 17/653,314 mailed Oct. 29, 2025.

Corrected Notice of Allowability for U.S. Appl. No. 17/808,354 mailed Nov. 25, 2025.

Corrected Notice of Allowability for U.S. Appl. No. 17/996,253 mailed Apr. 28, 2025.

Corrected Notice of Allowability for U.S. Appl. No. 18/134,857 mailed Mar. 14, 2025.

Corrected Notice of Allowability for U.S. Appl. No. 18/260,122 mailed Aug. 11, 2025.

Di Mauro, et al., "Penile length and circumference dimensions: A large study in young Italian men" Reconstructive Urology, Men's Health Working Parties of the European Association of Urology (EAU) Young Academic Urologists (YAU). pp. 1-7, Mar. 8, 2021.

Final Office Action for U.S. Appl. No. 17/051,600 mailed Aug. 6, 2025.

Final Office Action for U.S. Appl. No. 17/378,015 mailed Jun. 18, 2025.

Final Office Action for U.S. Appl. No. 17/394,055 mailed Sep. 24, 2025.

Final Office Action for U.S. Appl. No. 17/446,256 mailed Jun. 11, 2025.

Final Office Action for U.S. Appl. No. 17/446,654 mailed Dec. 22, 2025.

Final Office Action for U.S. Appl. No. 17/597,408 mailed Mar. 24, 2025.

Final Office Action for U.S. Appl. No. 17/614,173 mailed May 20, 2025.

Final Office Action for U.S. Appl. No. 17/628,411 mailed Apr. 30, 2025.

Final Office Action for U.S. Appl. No. 17/631,619 mailed Oct. 1, 2025.

Final Office Action for U.S. Appl. No. 17/653,137 mailed Jun. 25, 2025.

Final Office Action for U.S. Appl. No. 17/653,920 mailed Apr. 24, 2025.

Final Office Action for U.S. Appl. No. 17/664,487 mailed Jan. 5, 2026.

Final Office Action for U.S. Appl. No. 17/756,201 mailed Dec. 30, 2025.

Final Office Action for U.S. Appl. No. 17/757,311 mailed Mar. 31, 2025.

Final Office Action for U.S. Appl. No. 17/759,697 mailed Jun. 4, 2025.

Final Office Action for U.S. Appl. No. 17/808,354 mailed Jun. 13, 2025.

Final Office Action for U.S. Appl. No. 17/907,125 mailed Apr. 30, 2025.

Final Office Action for U.S. Appl. No. 17/929,887, filed Jan. 13, 2026.

Final Office Action for U.S. Appl. No. 18/003,029 mailed Nov. 26, 2025.

Final Office Action for U.S. Appl. No. 18/006,807 mailed Dec. 23, 2025.

Final Office Action for U.S. Appl. No. 18/043,618 mailed Nov. 26, 2025.

Final Office Action for U.S. Appl. No. 18/139,523 mailed May 8, 2025.

Final Office Action for U.S. Appl. No. 18/164,800 mailed Dec. 5, 2025.

Final Office Action for U.S. Appl. No. 18/247,986 mailed Jan. 7, 2026.

Final Office Action for U.S. Appl. No. 18/265,736 mailed Dec. 1, 2025.

Foamtech, "Foam Packaging Isnert: Best Selection Guide", https://web/archive.org/web/20170922162235/http://www.foamtechchina/com:80/foam-packaging-insert/, Sep. 22, 2017, 25 pages.

International Search Report and Written Opinion from International Application No. PCT/US2023/036875 mailed May 31, 2024.

International Search Report and Written Opinion from International Application No. PCT/US2023/077205 mailed Jul. 19, 2024.

International Search Report and Written Opinion from International Application No. PCT/US2024/058598 mailed Mar. 28, 2025.

International Search Report and Written Opinion from International Application No. PCT/US2025/018907 mailed May 16, 2025.

International Search Report and Written Opinion from International Application No. PCT/US2025/018909 mailed May 20, 2025.

International Search Report and Written Opinion from International Application No. PCT/US2025/018913 mailed Jun. 18, 2025.

Issue Notification for U.S. Appl. No. 16/433,773 mailed Jan. 21, 2026.

Issue Notification for U.S. Appl. No. 16/478,180 mailed Mar. 5, 2025.

Issue Notification for U.S. Appl. No. 16/904,868 mailed Apr. 30, 2025.

Issue Notification for U.S. Appl. No. 17/051,585 mailed Mar. 26, 2025.

Issue Notification for U.S. Appl. No. 17/444,792 mailed Jun. 25, 2025.

Issue Notification for U.S. Appl. No. 17/501,591 mailed Mar. 5, 2025.

Issue Notification for U.S. Appl. No. 17/597,673 mailed Jun. 4, 2025.

Issue Notification for U.S. Appl. No. 17/646,771 mailed Mar. 19, 2025.

Issue Notification for U.S. Appl. No. 17/653,920 mailed Oct. 22, 2025.

Issue Notification for U.S. Appl. No. 17/663,330 mailed Feb. 26, 2025.

Issue Notification for U.S. Appl. No. 17/749,340 mailed May 28, 2025.

Issue Notification for U.S. Appl. No. 17/755,236 mailed Oct. 29, 2025.

Issue Notification for U.S. Appl. No. 17/758,316 mailed Jun. 25, 2025.

Issue Notification for U.S. Appl. No. 17/907,125 mailed Dec. 30, 2025.

Issue Notification for U.S. Appl. No. 17/996,064 mailed Nov. 5, 2025.

Issue Notification for U.S. Appl. No. 17/996,155 mailed Oct. 8, 2025.

Issue Notification for U.S. Appl. No. 17/996,253 mailed Oct. 29, 2025.

Issue Notification for U.S. Appl. No. 17/996,468 mailed Nov. 26, 2025.

Issue Notification for U.S. Appl. No. 18/007,105 mailed Oct. 1, 2025.

Issue Notification for U.S. Appl. No. 18/044,413 mailed Dec. 30, 2025.

Issue Notification for U.S. Appl. No. 18/134,857 mailed May 28, 2025.

Issue Notification for U.S. Appl. No. 18/260,122 mailed Nov. 12, 2025.

Issue Notification for U.S. Appl. No. 18/415,080 mailed Apr. 9, 2025.

Issue Notification for U.S. Appl. No. 18/584,002 mailed Apr. 16, 2025.

(56)     References Cited

OTHER PUBLICATIONS

Non-Final Office Action for U.S. Appl. No. 16/433,773 mailed Feb. 28, 2025.

Non-Final Office Action for U.S. Appl. No. 16/452,258 mailed Sep. 24, 2025.

Non-Final Office Action for U.S. Appl. No. 17/051,600 mailed Feb. 28, 2025.

Non-Final Office Action for U.S. Appl. No. 17/378,015 mailed Dec. 12, 2025.

Non-Final Office Action for U.S. Appl. No. 17/394,055 mailed Mar. 13, 2025.

Non-Final Office Action for U.S. Appl. No. 17/394,055 mailed Mar. 19, 2025.

Non-Final Office Action for U.S. Appl. No. 17/446,256 mailed Dec. 2, 2025.

Non-Final Office Action for U.S. Appl. No. 17/446,654 mailed May 1, 2025.

Non-Final Office Action for U.S. Appl. No. 17/451,354 mailed Mar. 19, 2025.

Non-Final Office Action for U.S. Appl. No. 17/595,747 mailed Jun. 12, 2025.

Non-Final Office Action for U.S. Appl. No. 17/614,173 mailed Dec. 29, 2025.

Non-Final Office Action for U.S. Appl. No. 17/628,411 mailed Dec. 22, 2025.

Non-Final Office Action for U.S. Appl. No. 17/631,619 mailed Mar. 19, 2025.

Non-Final Office Action for U.S. Appl. No. 17/635,866 mailed Jul. 29, 2025.

Non-Final Office Action for U.S. Appl. No. 17/645,821 mailed Mar. 31, 2025.

Non-Final Office Action for U.S. Appl. No. 17/653,314 mailed May 8, 2025.

Non-Final Office Action for U.S. Appl. No. 17/655,464 mailed Mar. 20, 2025.

Non-Final Office Action for U.S. Appl. No. 17/664,487 mailed May 19, 2025.

Non-Final Office Action for U.S. Appl. No. 17/754,736 mailed Mar. 31, 2025.

Non-Final Office Action for U.S. Appl. No. 17/756,201 mailed Apr. 24, 2025.

Non-Final Office Action for U.S. Appl. No. 17/758,152 mailed Apr. 8, 2025.

Non-Final Office Action for U.S. Appl. No. 17/759,697 mailed Sep. 17, 2025.

Non-Final Office Action for U.S. Appl. No. 17/809,083 mailed Apr. 2, 2025.

Non-Final Office Action for U.S. Appl. No. 17/809,083 mailed Mar. 7, 2025.

Non-Final Office Action for U.S. Appl. No. 17/878,268 mailed Mar. 17, 2025.

Non-Final Office Action for U.S. Appl. No. 17/912,147 mailed May 29, 2025.

Non-Final Office Action for U.S. Appl. No. 17/929,887 mailed Jun. 25, 2025.

Non-Final Office Action for U.S. Appl. No. 17/930,238 mailed Jun. 30, 2025.

Non-Final Office Action for U.S. Appl. No. 17/933,590 mailed Jul. 29, 2025.

Non-Final Office Action for U.S. Appl. No. 17/996,064 mailed Mar. 6, 2025.

Non-Final Office Action for U.S. Appl. No. 17/996,556 mailed Dec. 22, 2025.

Non-Final Office Action for U.S. Appl. No. 18/003,029 mailed Apr. 18, 2025.

Non-Final Office Action for U.S. Appl. No. 18/006,807 mailed May 29, 2025.

Non-Final Office Action for U.S. Appl. No. 18/042,842 mailed May 22, 2025.

Non-Final Office Action for U.S. Appl. No. 18/043,618 mailed May 19, 2025.

Non-Final Office Action for U.S. Appl. No. 18/115,444 mailed Oct. 22, 2025.

Non-Final Office Action for U.S. Appl. No. 18/139,523 mailed Nov. 19, 2025.

Non-Final Office Action for U.S. Appl. No. 18/150,360 mailed Nov. 5, 2025.

Non-Final Office Action for U.S. Appl. No. 18/164,800 mailed Apr. 25, 2025.

Non-Final Office Action for U.S. Appl. No. 18/246,121 mailed Jan. 22, 2026.

Non-Final Office Action for U.S. Appl. No. 18/247,986 mailed Jun. 4, 2025.

Non-Final Office Action for U.S. Appl. No. 18/249,577 mailed Nov. 17, 2025.

Non-Final Office Action for U.S. Appl. No. 18/254,638 mailed Nov. 17, 2025.

Non-Final Office Action for U.S. Appl. No. 18/259,626 mailed Jul. 11, 2025.

Non-Final Office Action for U.S. Appl. No. 18/260,394, filed Jan. 13, 2026.

Non-Final Office Action for U.S. Appl. No. 18/264,004 mailed May 15, 2025.

Non-Final Office Action for U.S. Appl. No. 18/264,278 mailed Nov. 10, 2025.

Non-Final Office Action for U.S. Appl. No. 18/265,736 mailed Jul. 1, 2025.

Non-Final Office Action for U.S. Appl. No. 18/548,152 mailed Sep. 16, 2025.

Non-Final Office Action for U.S. Appl. No. 18/553,625 mailed Oct. 2, 2025.

Non-Final Office Action for U.S. Appl. No. 18/556,945 mailed Dec. 19, 2025.

Non-Final Office Action for U.S. Appl. No. 18/757,964 mailed Aug. 20, 2025.

Notice of Allowance for U.S. Appl. No. 16/433,773 mailed Oct. 10, 2025.

Notice of Allowance for U.S. Appl. No. 17/051,399 mailed Nov. 17, 2025.

Notice of Allowance for U.S. Appl. No. 17/051,600 mailed Jan. 5, 2026.

Notice of Allowance for U.S. Appl. No. 17/444,792 mailed Mar. 28, 2025.

Notice of Allowance for U.S. Appl. No. 17/451,345 mailed Jun. 24, 2025.

Notice of Allowance for U.S. Appl. No. 17/451,354 mailed Nov. 18, 2025.

Notice of Allowance for U.S. Appl. No. 17/596,629 mailed May 27, 2025.

Notice of Allowance for U.S. Appl. No. 17/597,673 mailed Feb. 26, 2025.

Notice of Allowance for U.S. Appl. No. 17/625,941 mailed Nov. 13, 2025.

Notice of Allowance for U.S. Appl. No. 17/645,821 mailed Nov. 24, 2025.

Notice of Allowance for U.S. Appl. No. 17/653,137 mailed Oct. 22, 2025.

Notice of Allowance for U.S. Appl. No. 17/653,314 mailed Oct. 20, 2025.

Notice of Allowance for U.S. Appl. No. 17/653,920 mailed Jul. 9, 2025.

Notice of Allowance for U.S. Appl. No. 17/755,236 mailed Jul. 17, 2025.

Notice of Allowance for U.S. Appl. No. 17/758,316 mailed Mar. 24, 2025.

Notice of Allowance for U.S. Appl. No. 17/808,354 mailed Nov. 12, 2025.

Notice of Allowance for U.S. Appl. No. 17/878,268 mailed Oct. 15, 2025.

Notice of Allowance for U.S. Appl. No. 17/907,125 mailed Sep. 26, 2025.

(56)        References Cited

OTHER PUBLICATIONS

Notice of Allowance for U.S. Appl. No. 17/912,147 mailed Dec. 3, 2025.
Notice of Allowance for U.S. Appl. No. 17/930,238 mailed Dec. 16, 2025.
Notice of Allowance for U.S. Appl. No. 17/996,064 mailed Jul. 29, 2025.
Notice of Allowance for U.S. Appl. No. 17/996,155 mailed Jun. 24, 2025.
Notice of Allowance for U.S. Appl. No. 17/996,155 mailed Mar. 11, 2025.
Notice of Allowance for U.S. Appl. No. 17/996,253 mailed Apr. 11, 2025.
Notice of Allowance for U.S. Appl. No. 17/996,253 mailed Jul. 11, 2025.
Notice of Allowance for U.S. Appl. No. 17/996,468 mailed Apr. 14, 2025.
Notice of Allowance for U.S. Appl. No. 17/996,468 mailed Jul. 15, 2025.
Notice of Allowance for U.S. Appl. No. 18/007,105 mailed Jun. 17, 2025.
Notice of Allowance for U.S. Appl. No. 18/044,413 mailed Sep. 16, 2025.
Notice of Allowance for U.S. Appl. No. 18/260,122 mailed Jul. 30, 2025.
Restriction Requirement for U.S. Appl. No. 17/625,887 mailed Sep. 2, 2025.
Restriction Requirement for U.S. Appl. No. 17/755,236 mailed Apr. 24, 2025.
Restriction Requirement for U.S. Appl. No. 17/929,887 mailed Mar. 10, 2025.
Restriction Requirement for U.S. Appl. No. 17/930,238 mailed Apr. 17, 2025.
Restriction Requirement for U.S. Appl. No. 17/996,556 mailed Aug. 11, 2025.
Restriction Requirement for U.S. Appl. No. 18/034,902 mailed Nov. 6, 2025.
Restriction Requirement for U.S. Appl. No. 18/041,109 mailed Jun. 4, 2025.
Restriction Requirement for U.S. Appl. No. 18/041,109 mailed Oct. 23, 2025.
Restriction Requirement for U.S. Appl. No. 18/150,360 mailed May 19, 2025.
Restriction Requirement for U.S. Appl. No. 18/246,121 mailed Jul. 25, 2025.
Restriction Requirement for U.S. Appl. No. 18/249,577 mailed Aug. 25, 2025.
Restriction Requirement for U.S. Appl. No. 18/254,638 mailed Jul. 21, 2025.
Restriction Requirement for U.S. Appl. No. 18/260,394 mailed Jul. 25, 2025.
Restriction Requirement for U.S. Appl. No. 18/335,579 mailed Nov. 26, 2025.
Restriction Requirement for U.S. Appl. No. 18/373,424 mailed Nov. 14, 2025.
Restriction Requirement for U.S. Appl. No. 18/376,274 mailed Dec. 10, 2025.
Restriction Requirement for U.S. Appl. No. 18/549,387 mailed Dec. 9, 2025.
Restriction Requirement for U.S. Appl. No. 18/551,492 mailed Nov. 10, 2025.
Restriction Requirement for U.S. Appl. No. 18/569,711 mailed Jan. 6, 2026.
Restriction Requirement for U.S. Appl. No. 18/569,778 mailed Jan. 15, 2026.
Restriction Requirement for U.S. Appl. No. 18/662,216 mailed Nov. 26, 2025.
Restriction Requirement for U.S. Appl. No. 19/237,638 mailed Dec. 18, 2025.
Supplemental Notice of Allowance for U.S. Appl. No. 17/597,673 mailed Apr. 10, 2025.
U.S. Appl. No. 17/596,629, filed Dec. 15, 2021.
U.S. Appl. No. 18/034,902, filed May 2, 2023.
U.S. Appl. No. 19/069,480, filed Mar. 4, 2025.
U.S. Appl. No. 19/078,602, filed Mar. 13, 2025.
U.S. Appl. No. 19/092,262, filed Mar. 27, 2025.
U.S. Appl. No. 19/110,938, filed Mar. 12, 2025.
U.S. Appl. No. 19/111,921, filed Mar. 14, 2025.
U.S. Appl. No. 19/127,234, filed May 5, 2025.
U.S. Appl. No. 19/171,983, filed Apr. 7, 2025.
U.S. Appl. No. 19/179,540, filed Apr. 15, 2025.
U.S. Appl. No. 19/202,862, filed May 8, 2025.
U.S. Appl. No. 19/207,699, filed May 14, 2025.
U.S. Appl. No. 19/215,723, filed May 22, 2025.
U.S. Appl. No. 19/237,368, filed Jun. 13, 2025.
U.S. Appl. No. 19/240,380, filed Jun. 17, 2025.
U.S. Appl. No. 19/329,723, filed Sep. 16, 2025.
U.S. Appl. No. 19/337,217, filed Sep. 23, 2025.
U.S. Appl. No. 19/356,506, filed Oct. 13, 2025.
U.S. Appl. No. 19/358,647, filed Oct. 15, 2025.
U.S. Appl. No. 19/370,361, filed Oct. 27, 2025.
U.S. Appl. No. 19/418,150, filed Dec. 12, 2025.
U.S. Appl. No. 19/443,729, filed Jan. 8, 2026.
U.S. Appl. No. 19/447,347, filed Jan. 13, 2026.
U.S. Appl. No. 19/451,614, filed Jan. 16, 2026.
U.S. Appl. No. 19/491,481, filed Dec. 9, 2025.
U.S. Appl. No. 19/494,631, filed Dec. 18, 2025.

* cited by examiner

800

EXTRUDING A SUPPORT — 810

SECURING A BODY INCLUDING THE SUPPORT TO A FLUID IMPERMEABLE BARRIER HAVING DISTAL END REGION AND A PROXIMAL END REGION DEFINING AN APERTURE SUCH THAT A PORTION OF THE BODY IS UNCOVERED BETWEEN THE DISTAL END REGION AND THE PROXIMAL END REGION — 820

MOLDED OR EXTRUDED FLUID COLLECTION DEVICES, AND RELATED SYSTEMS AND METHODS

CROSS-REFERENCE TO RELATED APPLICATIONS

This application is a National Phase of International Application No. PCT/US2022/039018 filed on Aug. 1, 2022, which claims priority to U.S. Provisional Patent Application No. 63/228,252 filed on Aug. 2, 2021, the disclosure of which is incorporated herein, in its entirety, by this reference.

BACKGROUND

An individual may have limited or impaired mobility such that typical urination processes are challenging or impossible. For example, the individual may have surgery or a disability that impairs mobility. In another example, the individual may have restricted travel conditions such as those experienced by pilots, drivers, and workers in hazardous areas. Additionally, fluid collection from the individual may be needed for monitoring purposes or clinical testing.

Bed pans and urinary catheters, such as a Foley catheter, may be used to address some of these circumstances. However, bed pans and urinary catheters have several problems associated therewith. For example, bed pans may be prone to discomfort, spills, and other hygiene issues. Urinary catheters be may be uncomfortable, painful, and may cause urinary tract infections.

Thus, users and manufacturers of fluid collection devices continue to seek new and improved devices, systems, and methods to collect urine.

SUMMARY

Embodiments disclosed herein are related to fluid collection devices, and related systems and methods. In an embodiment, a fluid collection device includes a fluid impermeable barrier and an elongated body that is at least partially fluid permeable. The fluid impermeable barrier has a distal end region and a proximal end region defining an aperture sized and dimensioned to have urine drawn therethrough by a vacuum source. The elongated body has a portion of the body between the distal end region and the proximal end region that is free from being covered by the fluid impermeable barrier and positioned on the fluid collection device to receive urine discharged from a urethra at least proximate to the portion of the body. The fluid collection device includes at least one of the fluid impermeable barrier being an injection molded fluid impermeable barrier or the body including at least an extruded support.

In an embodiment, a method of manufacturing a fluid collection device includes injection molding a fluid impermeable barrier of the fluid collection device to include a chamber, an opening in fluid communication with the chamber, and an aperture at least partially defined by the fluid impermeable barrier. The opening is positioned on the fluid collection device to receive urine discharged from a urethra at least proximate to the opening and the aperture is sized and dimensioned to have urine drawn therethrough by a vacuum source. The method also includes positioning a fluid permeable body within the chamber to extend across at least a portion of the opening.

In an embodiment, a method of manufacturing a fluid collection device includes extruding a support to include at least one slot extending longitudinally on the extruded support. The method also includes securing a body that includes the extruded support and is at least partially fluid permeable to a fluid impermeable barrier having distal end region and a proximal end region defining an aperture such that a portion of the body is not covered by the fluid impermeable barrier between the distal end region and the proximal end region and positioned on the fluid collection device to receive urine discharged from a urethra at least proximate to the portion of the body. The aperture is in fluid communication with the at least one slot and sized and dimensioned to have urine drawn therethrough by a vacuum source.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the present disclosure, wherein identical reference numerals refer to identical or similar elements or features in different views or embodiments shown in the drawings.

DETAILED DESCRIPTION

Embodiments disclosed herein are related to fluid collection devices, and related systems and methods of manufacture. The devices and systems disclosed herein are configured to collect fluids from an individual. The fluids collected by the fluid collection devices may include at least one of urine, vaginal discharge, penile discharge, reproductive fluids, blood, sweat, wound exudate, or other bodily fluids. Fluid collection devices described herein include alternative and improved methods of manufacturing and assembly of fluid collection devices, as well as alternative and improved fluid collection devices resulting from these methods of manufacturing and assembly. In at least one, some, or all embodiments described herein, efficient and repeatable manufacturing and assembly of fluid collection devices result in the technical effect of repeatability and reducing the cost and/or time for assembly of the fluid collection device.

In various embodiments, the methods of manufacture and/or assembly may include one or more of: molding the exterior fluid impermeable barrier to receive the inner components (e.g., body and/or conduit) rather than using manpower to align the fluid impermeable barrier and the inner components; molding the fluid impermeable barrier with a flat back side such that only about half of the fluid permeable body is required in the fluid collection device; and/or extruding a three-layer structure that include an inner lumen (e.g., conduit), an extruded support, and a fluid permeable membrane in one structure that may be cut to length and capped at the ends (with one end having an aperture for the tubing).

Furthermore, embodiments of the fluid collection devices may include a shape memory material (e.g., bendable spine) that provides use benefits for positioning and securement for the user. Some embodiments may include incorporation of a label into the fluid collection device that includes instructions, product identification, and/or user-notated usage data. The incorporation of labeling in at least one, some, or all embodiments described herein results in the technical effect of reducing packaging required for the fluid collection device, providing information or instructions to the user in a place that is less likely to be discarded by the user, and/or providing a space to record relevant data pertaining to fluid collection of the user.

Figure 1:
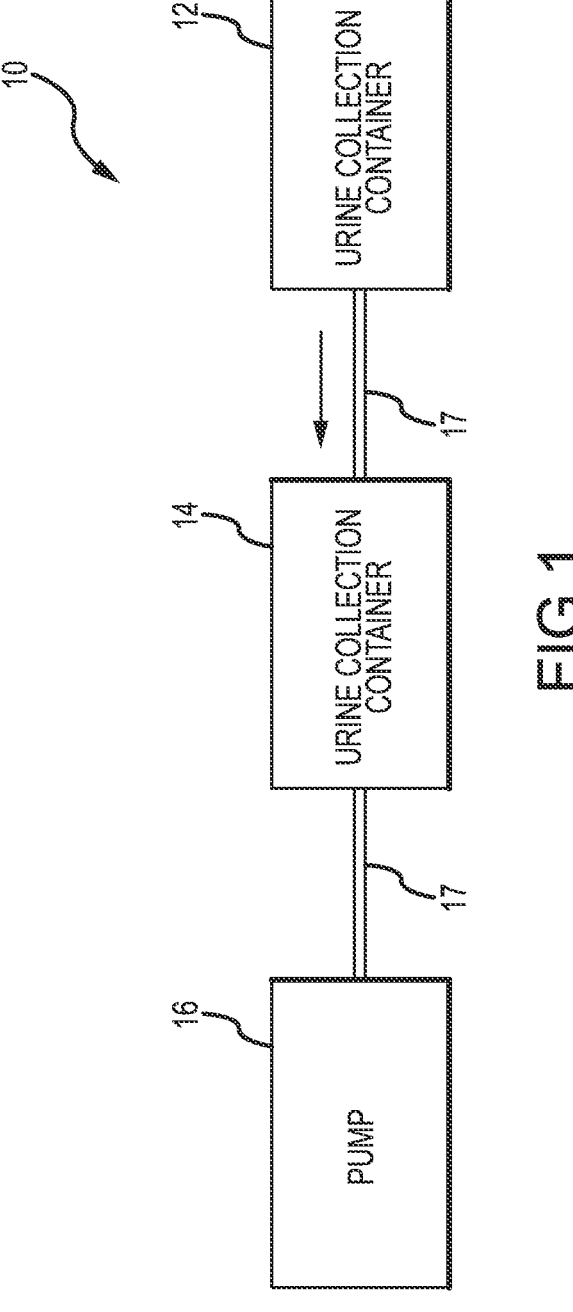
FIG. 1 is a block diagram of a fluid collection system, according to an embodiment.

FIG. 1 is a block diagram of a fluid collection system 10, according to an embodiment. The fluid collection system 10 may be included in embodiments of fluid collection systems described herein. The system 10 includes a fluid collection device 12 (e.g., any of the fluid collection devices disclosed herein), a urine collection container 14, and a pump 16 (or vacuum source). The fluid collection device 12, the urine collection container 14, and the pump 16 may be fluidly coupled to each other via one or more conduits 17. For example, fluid collection device 12 may be operably coupled to one or more of the urine collection container 14 or the pump 16 via the conduit 17. In some embodiments, the pump 16 may be secured directly to the urine collection container 14. Fluid (e.g., urine or other bodily fluids) collected in the fluid collection device 12 may be removed from the fluid collection device 12 via the conduit 17 secured to the fluid collection device 12. Suction force may be introduced into the chamber of the fluid collection device 12 via the inlet of the conduit 17 responsive to suction (e.g., vacuum) force applied at the outlet of the conduit 17.

The suction force may be applied to the outlet of the conduit 17 by the pump 16 either directly or indirectly. The suction force may be applied indirectly via the urine collection container 14. For example, the outlet of the conduit 17 may be disposed within or fluidly coupled to an interior region of the urine collection container 14 and an additional conduit 17 may extend from the urine collection container 14 to the pump 16. Accordingly, the pump 16 may apply suction to the fluid collection device 12 via the urine collection container 14. The suction force may be applied directly via the pump 16. For example, the outlet of the conduit 17 may be disposed within the pump 16. An additional conduit 17 may extend from the pump 16 to a point outside of the fluid collection device 12, such as to the urine collection container 14. In such examples, the pump 16 may be disposed between the fluid collection device 12 and the urine collection container 14.

The urine collection container 14 is sized and shaped to retain a fluid therein. The urine collection container 14 may include a bag (e.g., drainage bag), a bottle, a canister, or a cup (e.g., collection jar), or any other enclosed container for storing bodily fluid(s) such as urine. In some examples, the conduit 17 may extend from the fluid collection device 12 and attach to the urine collection container 14 at a first point therein. An additional conduit 17 may attach to the urine collection container 14 at a second point thereon and may extend and attach to the pump 16. Accordingly, a vacuum (e.g., suction) may be drawn through fluid collection device 12 via the urine collection container 14. Fluid, such as urine, may be drained from the fluid collection device 12 using the pump 16.

The pump 16 may include one or more of a manual vacuum pump, and electric vacuum pump, a diaphragm pump, a centrifugal pump, a displacement pump, a magnetically driven pump, a peristaltic pump, or any pump configured to produce a vacuum. The pump 16 may provide a vacuum or suction to remove fluid from the fluid collection device 12. In some examples, the pump 16 may be powered by one or more of a power cord (e.g., connected to a power socket), one or more batteries, or even manual power (e.g., a hand operated vacuum pump). In some examples, the pump 16 may be sized and shaped to fit outside of, on, or within the fluid collection device 12. For example, the pump 16 may include one or more miniaturized pumps or one or more micro pumps. The vacuum sources disclosed herein may include one or more of a switch, a button, a plug, a remote, or any other device suitable to activate the pump 16.

Fluid collection devices described herein may include a fluid impermeable barrier and a body that is at least partially fluid permeable. The fluid impermeable barrier may include a distal end region and a proximal end region defining an aperture sized and dimensioned to have urine drawn therethrough by a vacuum source. The elongated body may have a portion of the body that is not covered by the fluid impermeable barrier between the distal end region and the proximal end region (e.g., the fluid impermeable barrier is absent between at least a portion of the distal end region and the proximal end region of the elongated body, or at least a portion of the elongated body between the distal end region and the proximal end region of the elongated body is free from covering by the fluid impermeable barrier) and positioned on the fluid collection device to receive urine discharged from a urethra at least proximate to the portion of the body. The fluid collection devices may include at least one of the fluid impermeable barrier being an injection molded fluid impermeable barrier or the body having an extruded support.

Figures 2A, 2B:
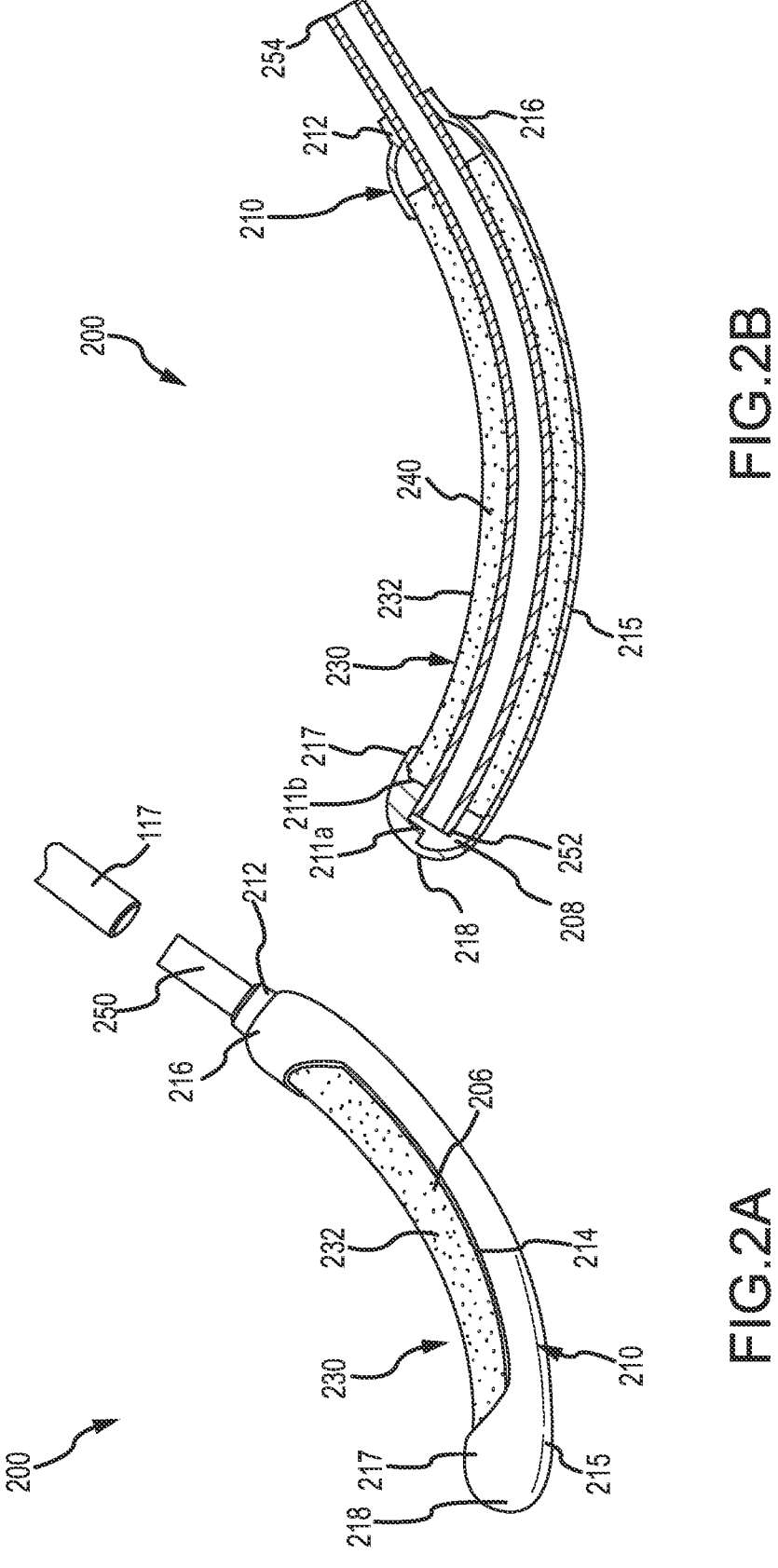
FIG. 2A is a front isometric view of a fluid collection device, according to an embodiment.
FIG. 2B is a longitudinal cross-sectional view of the fluid collection device of FIG. 2A.
Figure 2C:
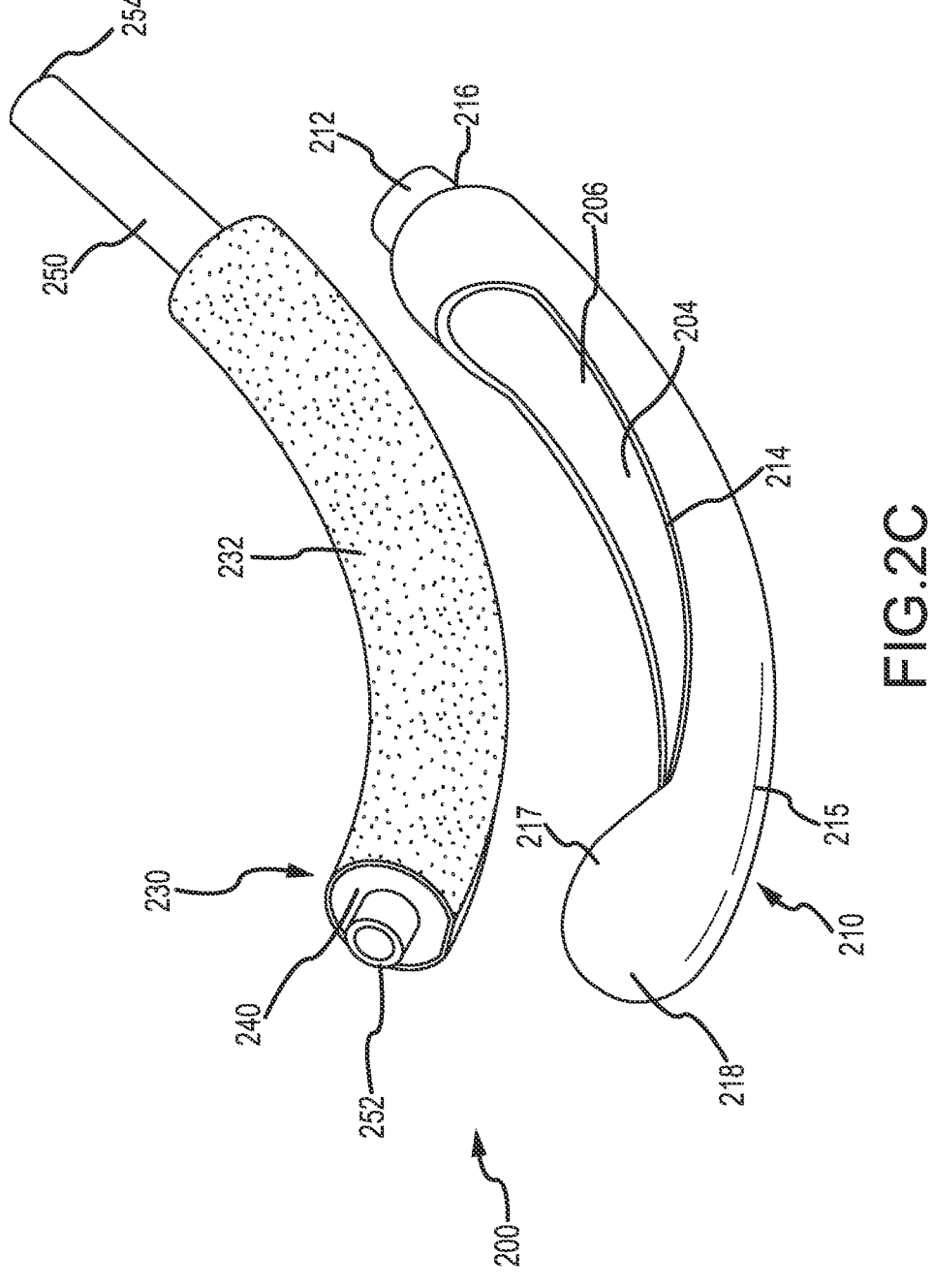
FIG. 2C is an exploded view of the fluid collection device of FIG. 2A.

Turning now to FIGS. 2A-2C, a fluid collection device may include a fluid impermeable barrier 210 and a fluid permeable body 230. The fluid impermeable barrier 210 may be elongated and include a distal region 218, a proximal end region 216, an aperture 212 or port positioned at the proximal end region 216 and sized and dimensioned to urine drawn therethrough by a vacuum source. The fluid impermeable barrier 210 may include a back side 215 and a front side 217. The front side 217 is positioned to be oriented towards the user when the fluid collection device 200 is in use. In some embodiments, the fluid impermeable barrier 210 may at least partially define a chamber 204 and an opening 206 on the front side 217 in fluid communication with the chamber 204 and positioned on the fluid collection device 200 to receive urine discharged form a urethra that is at least proximate (e.g., adjacent) to the opening 206. In some embodiments, an inward border or edge 214 of the fluid impermeable barrier 210 defines the opening 206. The edge 214 may include two or more opposing arced portions, the arced portions following the outer circumference or periphery of the fluid impermeable barrier 210.

The fluid impermeable barrier 210 also may at least partially define a reservoir 208 (e.g., sump) in the chamber 204 at the distal end region 218 of the fluid impermeable barrier 210. The reservoir 208 may be positioned for fluid collection in the fluid collection device 200 before withdraw from the fluid collection device 200 through a conduit 250 having an inlet 252 positioned proximate to the reservoir 208. In some embodiments, the reservoir 208 may be an at least partially (e.g., entirely) unoccupied portion of the chamber 204 and is at least partially (e.g., entirely) void of other material. In some embodiments, the reservoir 208 may be substantially filled with one or more fluid permeable materials described herein. In some embodiments, the reservoir 208 is defined at least partially by a terminating end the fluid permeable body 230 (shown in FIG. 2B) and the distal end region 218 of the fluid impermeable barrier 210.

In some embodiments, the fluid impermeable barrier 210 may include one or more protrusions 211a positioned within the chamber 204 at the distal end region 218 to space at least a portion of the inlet 252 from the distal end region 218 of the fluid impermeable barrier 210 effective to allow fluid communication between the chamber and the inlet 252. For example, the fluid impermeable barrier 210 may include a protrusion 211a at the distal end region 218 protruding into the reservoir 208. The protrusion 211a may be sized smaller than the inlet 252 such that if the conduit 250 is pushed too far into the chamber 204, the protrusion 211a may contact only a portion (e.g., a front portion) of the inlet 252 of the conduit 250, but also space a portion of the inlet 252 from the distal end region 218 of the fluid impermeable barrier 210. This space between the inlet 252 and the distal end region 218 of the fluid impermeable barrier 210 allows fluid to still be pulled into the conduit 250 even when the protrusion 211a is contacting a portion of the inlet 252. The protrusion 211a in at least one, some, or all embodiments, then, results in the technical effect of preventing the conduit 250 from being blocked or plugged if the conduit 250 is pushed too far into the chamber 204.

In some embodiments, the fluid impermeable barrier 210 may include one or more protrusions 211b positioned within the chamber 204 at the distal end region 218 to space at least a portion of the fluid permeable body 230 from the distal end region 218 of the fluid impermeable barrier 210. For example, the fluid impermeable barrier 210 may include a protrusion 211b at the distal end region 218 protruding into the reservoir 208. The protrusion 211b may be sized smaller than the distal end of the fluid permeable body 230 such that if the fluid permeable body 230 is pushed too far into the chamber 204, the protrusion 211b may contact only a portion (e.g., a front portion) of the fluid permeable body 230, but also space a portion of fluid permeable body 230 from the distal end region 218 of the fluid impermeable barrier 210. This space between the fluid permeable body 230 and the distal end region 218 of the fluid impermeable barrier 210 allows the reservoir 208 to remain void or open for urine collection.

The fluid impermeable barrier 210 may be substantially cylindrical. In some embodiments, the fluid impermeable barrier 210 may include other geometrical shapes and configurations. The fluid impermeable barrier 202 may be formed of any suitable fluid impermeable materials, such as a fluid impermeable polymer (e.g., silicone, polypropylene, polyethylene, polyethylene terephthalate, a polycarbonate, etc.), polyurethane films, thermoplastic elastomer (TPE), rubber, thermoplastic polyurethane (TPU), another suitable material, or combinations thereof. The fluid impermeable barrier 210 is flexible, thereby enabling the fluid collection device 200 to bend or curve when positioned against the body of a wearer. Example fluid impermeable barriers may include, but are not limited to, a fluid impermeable barrier including at least one of Versaflex CL 2000X TPE, Dynaflex G6713 TPE, or Silpuran 6000/05 A/B silicone. In an embodiment, the fluid impermeable barrier 210 may be air permeable. In such an embodiment, the fluid impermeable barrier 210 may be formed of a hydrophobic material that defines a plurality of pores. In an embodiment, one or more portions of at least the outer surface of the fluid impermeable barrier 210 may be formed from a soft and/or smooth material, thereby reducing chaffing.

In some embodiments, the fluid impermeable barrier 210 may be molded, such as injection molded. For example, the fluid impermeable barrier 210 may be injection molded from one or more of silicone or a polymer such as TPE or TPU. The fluid impermeable barrier 210 may be injection molded as one component. In some embodiments, the fluid impermeable barrier 210 may be injection molded to be curved or arced longitudinally. Injection molding the fluid impermeable barrier 210 may reduce the cost of manufacturing the fluid impermeable barrier 210 and the fluid collection device 200. For example, injection molding the fluid impermeable barrier 210 in at least one, some, or all embodiments results in the technical effect of reducing the material cost and provide a faster cycle time for manufacturing the fluid impermeable barrier 210. Injection molding the fluid impermeable barrier 210 in at least one, some, or all embodiments also results in the technical advantage of repeatability and consistency. Injection molding the fluid impermeable barrier 210 in at least one, some, or all embodiments also may result in the technical advantage of incorporating features described herein into a single body.

The fluid collection device 200 also includes the fluid permeable body 230 positioned within the chamber 204 and extending at least partially across the opening 206 and at least partially between the distal end region 217 and the proximal end region 216. The fluid permeable body 230 may be shaped generally complementary to the shape of the chamber 204 of the fluid impermeable barrier 210. In some embodiments, the fluid permeable body 230 fills substantially all of the chamber 204, except for the reservoir 208.

The fluid permeable body 230 can be configured to wick and/or allow transport of fluid away from the opening 206 towards the reservoir 208 and/or the inlet 252. More specifically, the fluid permeable body 230 can be configured to wick and/or allow transport of fluid away from the opening 206 toward the reservoir 208 and the inlet 252. The fluid permeable body 230 can include any material that can wick and/or allow transport of the fluid. The permeable properties referred to herein can be wicking, capillary action, diffusion, or other similar properties or processes, and are referred to herein as "permeable" and/or "wicking." Such "wicking" or other physical properties may exclude absorption into the fluid permeable body 230, such as not include adsorption of the bodily fluids into the fluid permeable body 230. Put another way, substantially no absorption or solubility of the bodily fluids into the material may take place after the material is exposed to the bodily fluids and removed from the bodily fluids for a time. While no absorption or solubility is desired, the term "substantially no absorption" may allow for nominal amounts of absorption and/or solubility of the bodily fluids into the fluid permeable body 230 (e.g., absorbency), such as less than about 30 wt % of the dry weight of the fluid permeable body 230, less than about 20 wt %, less than about 10 wt %, less than about 7 wt %, less than about 5 wt %, less than about 3 wt %, less than about 2 wt %, less than about 1 wt %, or less than about 0.5 wt % of the dry weight of the fluid permeable body 230. In an embodiment, the fluid permeable body 230 may include at least one absorbent or adsorbent material.

The fluid permeable body 230 can include a one-way fluid movement fabric. As such, the fluid permeable body 230 can remove fluid from the area around the urethra, wound, and/or skin, thereby leaving the area dry. The fluid permeable body 230 can enable the fluid to flow generally towards the reservoir 208 and the inlet 252. The fluid permeable body 230 can include a porous or fibrous material, such as hydrophilic polyolefin. In some embodiments, the fluid permeable body 230 consists of or consists essentially of a porous or fibrous material, such as hydrophilic polyolefin. Examples of polyolefin that can be used in the fluid permeable body 230 include, but are not limited to, polyethylene, polypropylene, polyisobutylene, ethylene propylene rubber, ethylene propylene diene monomer, or combinations thereof. Moreover, the fluid permeable body 230 can be manufactured according to various manufacturing methods, such as molding, extrusion, or sintering. For example, in some embodiments, the fluid permeable support 240 of the fluid permeable body 230 may be formed through extrusion. In some embodiments, the fluid permeable support 240 may include open or closed cell foam extrusion. The fluid permeable body 230 can include varying densities or dimensions.

In some embodiments, the fluid permeable body 230 can include two or more layers of fluid permeable materials. For example, the fluid permeable body 230 can include a fluid permeable membrane 232 covering or wrapped around a fluid permeable support 240, with both the fluid permeable membrane and the fluid permeable support being disposed at least partially in the chamber 204. The fluid permeable membrane 232 can cover or extend across at least a portion (e.g., all) of at least the side of the fluid permeable support 240 facing the urethra of the user. The fluid permeable membrane 232 and the fluid permeable support 240 can be configured to wick any fluid away from the opening 206, thereby preventing the fluid from escaping the chamber 204 through the opening 206 and promoting removal of the fluid from the chamber 204 through the conduit 250. The permeable properties referred to herein can be wicking, capillary action, diffusion, or other similar properties or processes, and are referred to herein as "permeable" and/or "wicking."

The fluid permeable membrane 232 and the fluid permeable support 240 also can wick and/or allow transport of the fluid generally towards the reservoir 208. The fluid permeable membrane 232 can include any material that can wick the fluid. For example, the fluid permeable membrane can include fabric, such as a gauze (e.g., a silk, linen, polymer based materials such as polyester, or cotton gauze), nylon (such as a spun nylon fibers), another soft fabric (e.g., jersey knit fabric or the like), or another smooth fabric (e.g., rayon, satin, or the like). Forming the fluid permeable membrane from gauze, soft fabric, and/or smooth fabric can reduce chaffing caused by the fluid collection device 200. Other embodiments of fluid permeable membranes and fluid permeable supports are disclosed in U.S. patent application Ser. No. 15/612,325 filed on Jun. 2, 2017; U.S. patent application Ser. No. 15/260,103 filed on Sep. 8, 2016; U.S. patent application Ser. No. 15/611,587 filed on Jun. 1, 2017; PCT Patent Application No. PCT/US19/29608, filed on Apr. 29, 2019, the disclosure of each of which is incorporated herein, in its entirety, by this reference. In many embodiments, the fluid permeable body 230 includes a fluid permeable support 240 including a porous spun nylon fiber structure and a fluid permeable wicking membrane 232 including gauze at least partially enclosing the spun nylon fiber structure. For example, the fluid permeable body 230 may include a gauze or other wicking fabric positioned to contact the skin of the user through the opening 206. In some embodiments, the gauze or other wicking fabric is wrapped around a body of spun nylon fibers material and/or covering both sides of a substantially planar spun nylon fibers material. In some embodiments, the gauze or other wicking fabric covers the side of substantially planar spun nylon fibers material that is oriented towards the skin of the user.

The fluid collection device 200 also includes the conduit 250 that is at least partially disposed in the chamber 204. The conduit 250 (e.g., a tube) may provide fluid communication between an interior region of the chamber 204 (e.g., the reservoir 208) and a fluid storage container (not shown) or a vacuum source (not shown). For example, the conduit 250 may directly or indirectly fluidly couple the interior region of the chamber 204 with the fluid storage container or the portable vacuum source. The conduit 250 includes the inlet 252 positioned within the chamber 204 proximate to the reservoir 208 and/or the distal end region 218 of the fluid impermeable barrier 210. The inlet 252 may be substantially flush with the distal end of the fluid permeable body 230, extending at least partially from the fluid permeable body 230, or recessed from the fluid permeable body 230. In some embodiments, the conduit 250 extends through the aperture 212 and includes an outlet 254 positioned outside the chamber 204. The outlet 254 may be configured to connect with an additional conduit 117 in fluid communication with a vacuum source effective to provide fluid communication between the conduit 250 and the additional conduit 117.

Figures 3A, 3B:
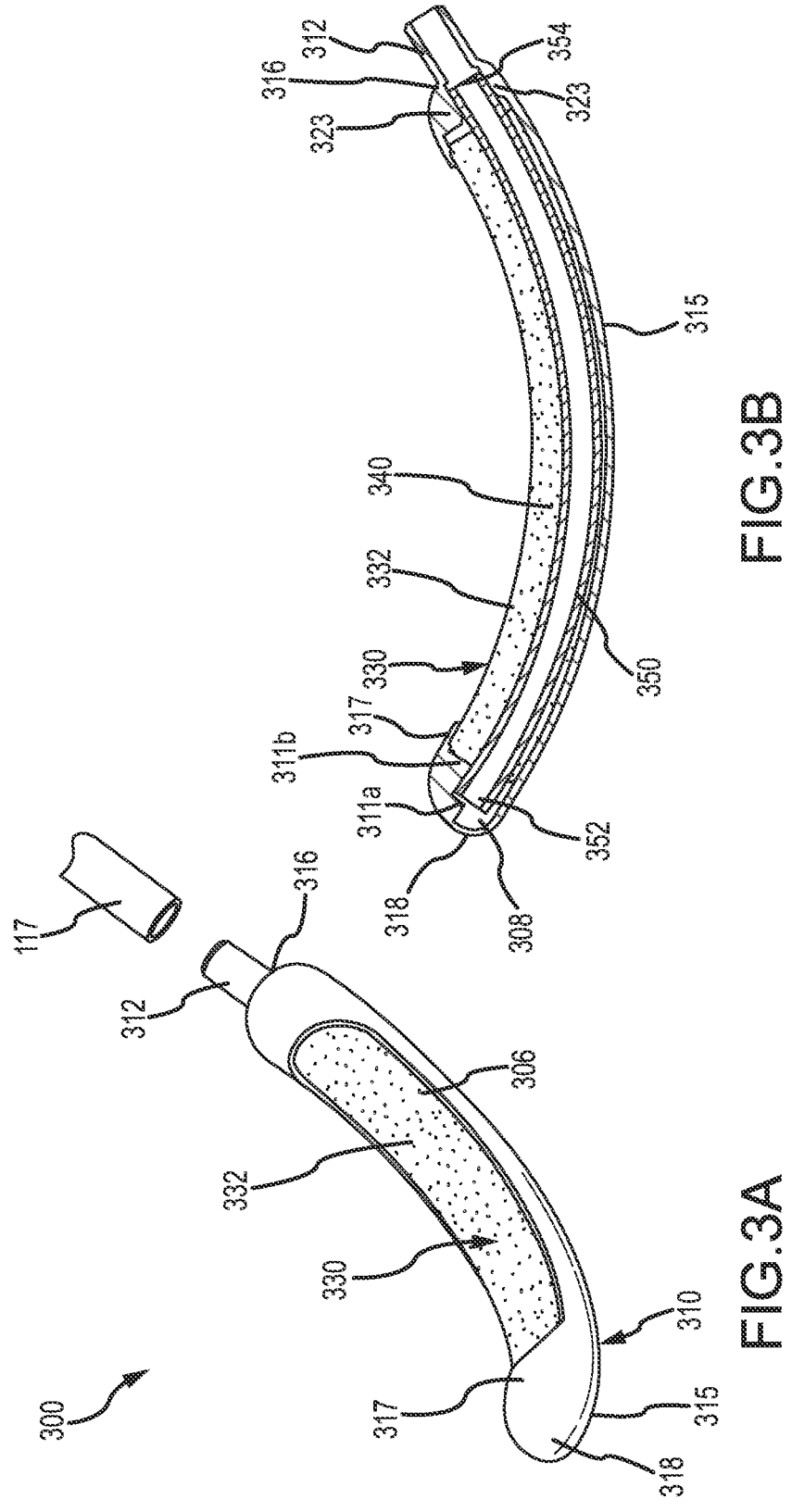
FIG. 3A is a front isometric view of a fluid collection device, according to an embodiment.
FIG. 3B is a longitudinal cross-sectional view of the fluid collection device of FIG. 3A.
Figure 3C:
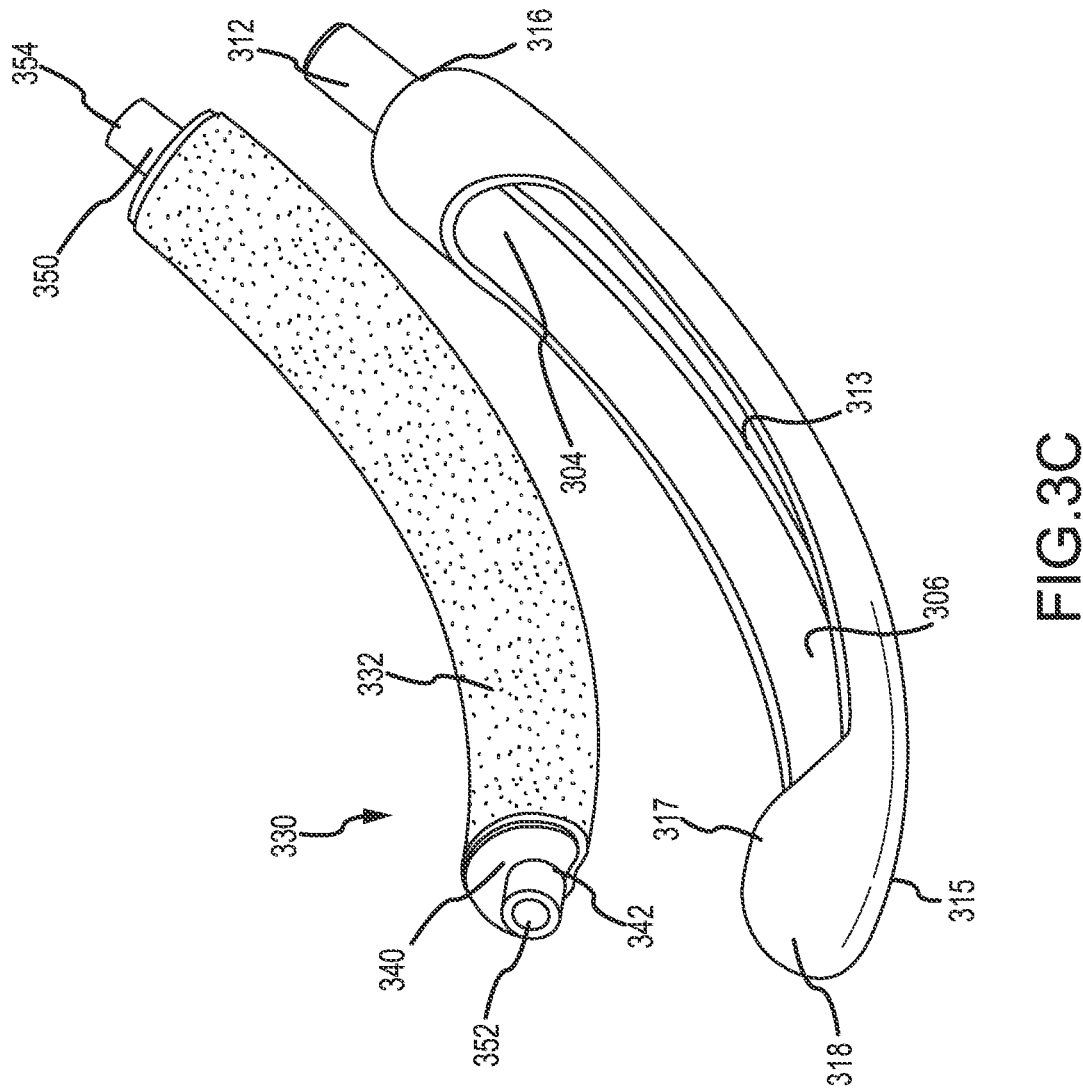
FIG. 3C is an exploded view of the fluid collection device of FIG. 3A.

Turning to FIGS. 3A-3C, a fluid collection device 300 may include a fluid impermeable barrier 310 and a fluid permeable body 330. Unless otherwise noted, the fluid collection device 300 may include any aspect of the fluid collection device 200. For example, the fluid collection device 300 may include the fluid impermeable barrier 310 having a proximal end region 316 and a distal end region 318 and defining a chamber 304 and an opening 306 on a front side 317 of the fluid impermeable barrier 310. The fluid collection device 300 may include one or more protrusions 311a, 311b and a reservoir 308 of void space at the distal end region 318 of the fluid impermeable barrier 310. The fluid collection device 300 also may include the fluid permeable body 330 including a fluid permeable membrane 332 and a fluid permeable support 340.

In some embodiments, the fluid impermeable barrier 310 may include an aperture 312 defined by an external port at the proximal end region 316 of the fluid impermeable barrier 310. The external port is sized and dimensioned to detachably secure to an additional conduit 317 effective to provide fluid communication between the additional conduit 117 and the chamber 304. In some embodiments, the fluid imperme-able barrier 310 may define an internal port 323 positioned within the fluid collection device 300 at the proximal end region 316 of the fluid impermeable barrier 310 and in fluid communication with the aperture 312. The fluid collection device 300 also may include a conduit 350 partially posi-tioned or positionable in the internal port 323 of the fluid impermeable barrier 310. For example, the conduit 350 may include an outlet 354 positioned or positionable in the internal port 323. The conduit 350 also may include an inlet 352 positioned in the chamber 304 proximate to the reser-voir 308 in distal end region 318 of the fluid impermeable barrier 310.

In some embodiments, the fluid impermeable barrier 310 includes a rear side 315 and a front side 317. The rear side 315 of the fluid impermeable barrier 310 includes an elon-gated planar portion extending at least partially between the proximal end region 316 and the distal end region 318. The front side 317 of the fluid impermeable barrier 310 includes an arced region at each of the distal end region 318 and the proximal end region 316. This configuration of the fluid impermeable barrier 310 results in the technical effect of using less material, thereby reducing costs of manufacturing the fluid collection device 300 while still providing the same effective fluid collection diameter. The fluid impermeable barrier 310 may include one or more internal longitudinal ribs 313 protruding into the chamber 304 and helping maintain shape of the fluid impermeable barrier 310. The one or more ribs 313 may include a material that is stiffer than the remainder of the fluid impermeable barrier 310.

In some embodiments, the fluid permeable body 330 includes at least an elongated fluid permeable support 340 having an arced profile defining a channel 342 and comple-mentary to the arced region at each of the distal end region 318 and the proximal end region 316. For example, the fluid permeable support 340 may include a cross-sectional profile that is semi- or half-circle shaped. The conduit 350 may be positioned at least partially (e.g., entirely) within the channel 342. In some embodiments, the fluid permeable body 330 also includes a fluid permeable membrane 332 positioned around the fluid permeable support 340. In some embodi-ments, the fluid permeable membrane 332 is wrapped or positioned around the fluid permeable support 340 with the conduit 350 positioned within the channel 342 such that the conduit 350 is positioned between some of the fluid perme-able support 340 and some of the fluid permeable membrane 332. The fluid permeable membrane 332 may help secure the conduit 350 in the channel 342. This configuration of the fluid permeable body 330 in at least one, some, or all embodiments results in the technical effect of using less material, thereby reducing costs of manufacturing the fluid collection device 300.

Figure 4:
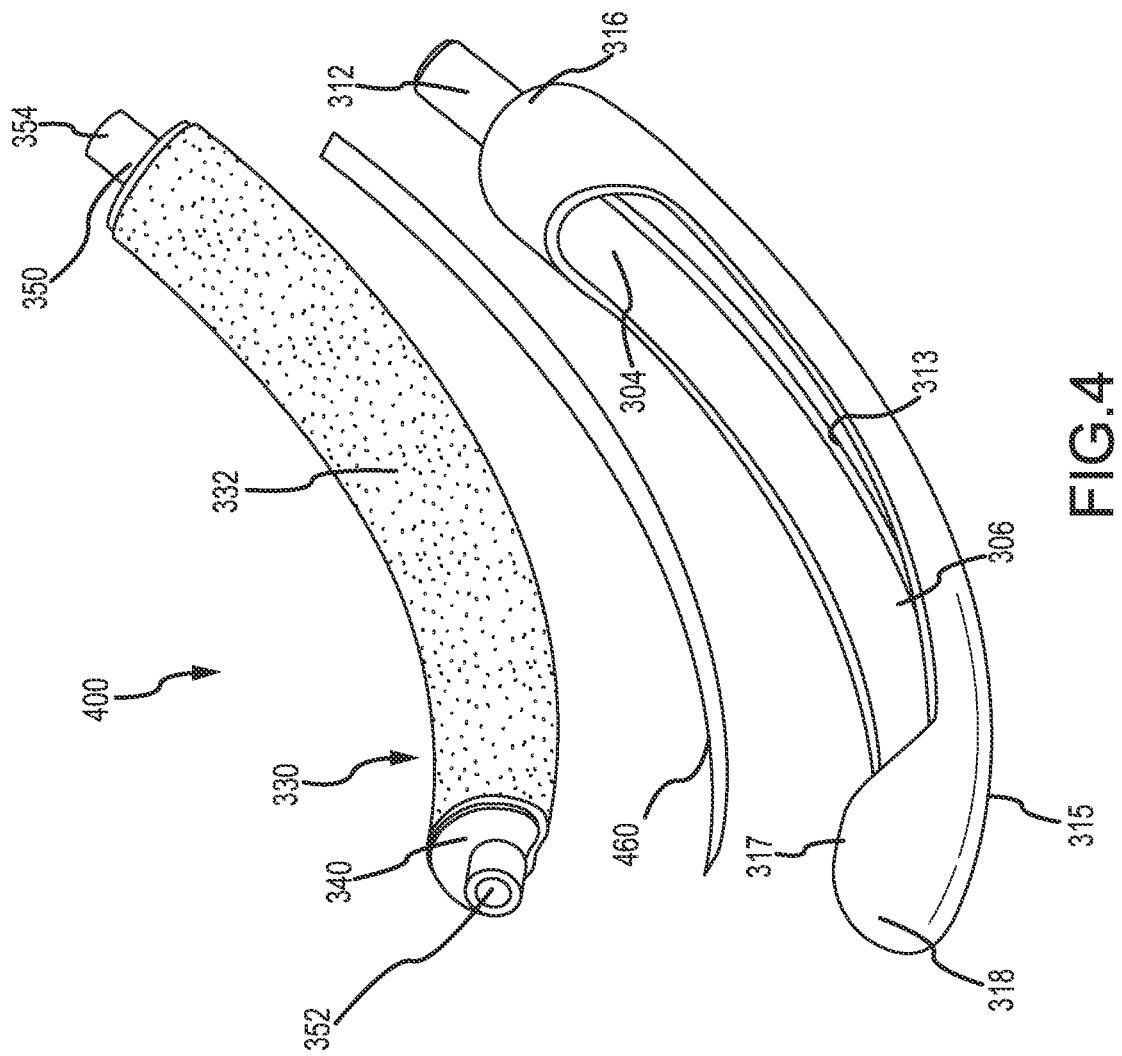
FIG. 4 is an exploded view of a fluid collection device, according to an embodiment.
Figure 5B:
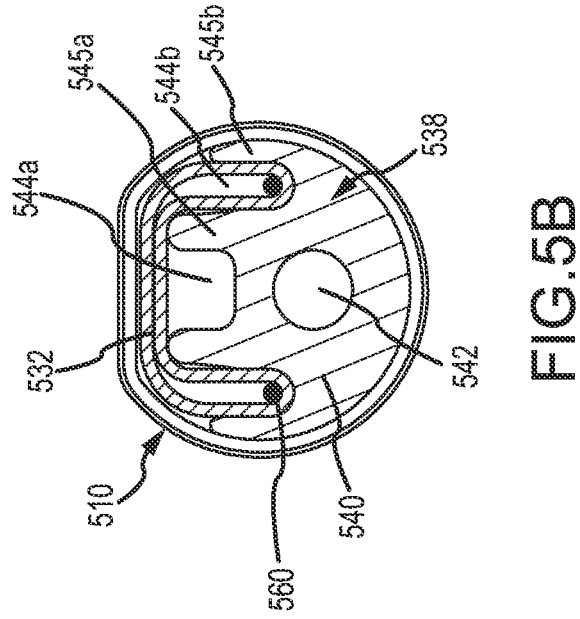
FIG. 5B is a transverse cross-sectional view of the fluid collection device of FIG. 5A.
Figure 5A:
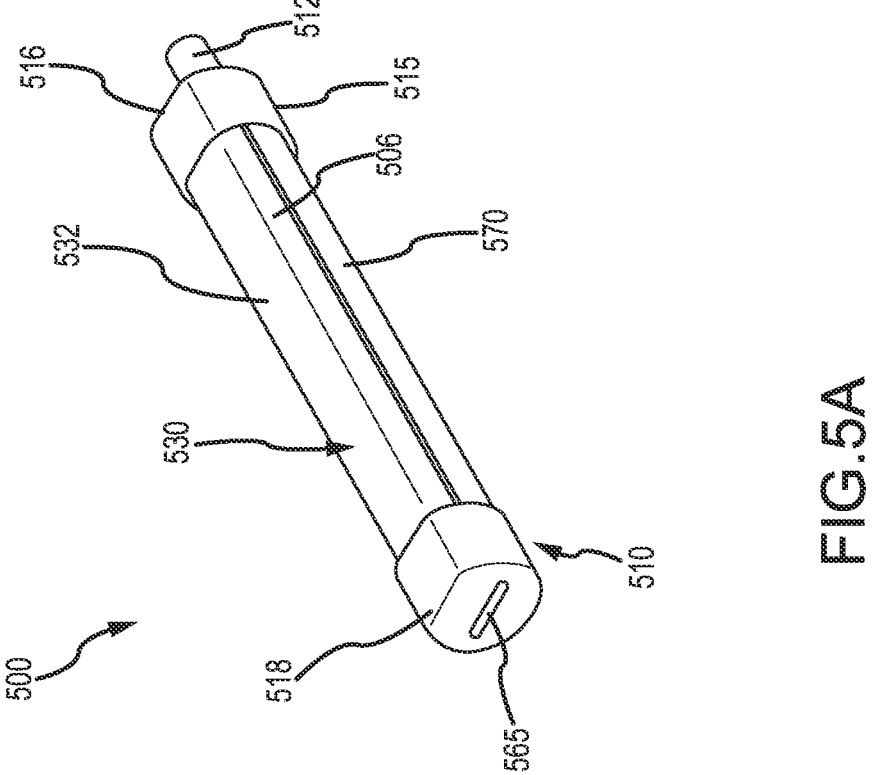
FIG. 5A is a front isometric view of a fluid collection device, according to an embodiment.
Figures 5C, 5D:
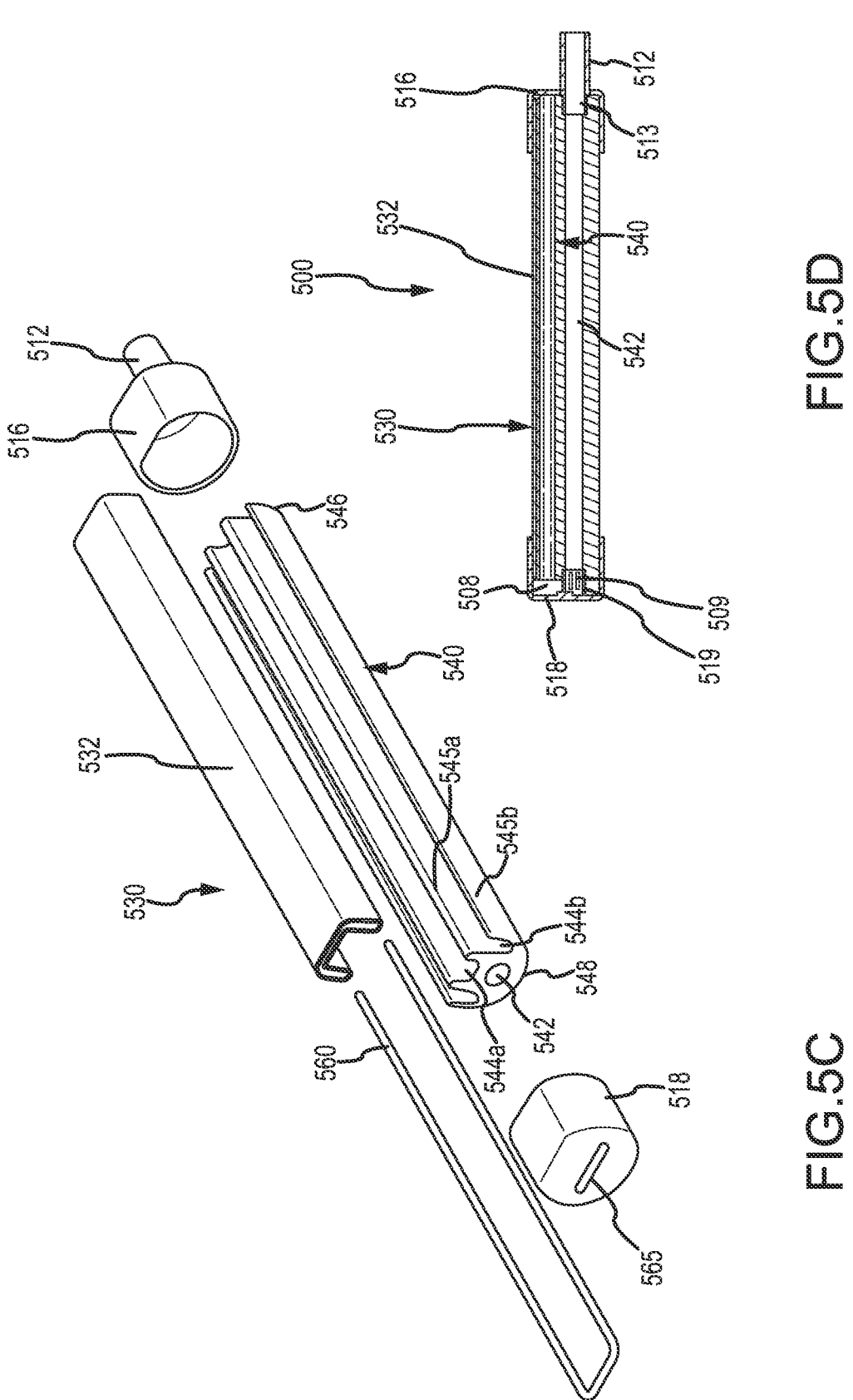
FIG. 5C is an exploded view of the fluid collection device of FIG. 5A.
FIG. 5D is a longitudinal cross-sectional view of the fluid collection device of FIG. 5A.

Turning to FIG. 4, a fluid collection device 400 may include a support member 460 secured to the rear side of the fluid impermeable barrier 410. Unless otherwise noted, the fluid collection device 400 may include any aspect of the fluid collection devices 200, 300. Moreover, the support member 460 may be include any of fluid collection device 200, 300. The support member 460 may include a shape memory polymer or a metal. For example, the support member 460 may include a malleable metal strip or wire trapped between the fluid permeable body 330 and the fluid impermeable barrier 310.

In some embodiments, at least the support member 460 may include a shape memory material such as a shape memory polymer or a metal (e.g., shape memory metal). The shape memory material may be secured to or embedded into at least a portion of the fluid impermeable barrier 310. Suitable shape memory materials are composed to adopt an intermediate or permanent shape in response to a stimuli. The stimuli may include an external physical force (e.g., bending force), heat, electrical bias, or a magnetic field. While the term "shape memory" is used to describe some of the "shape memory materials" herein, it should be under-stood that, in some examples, the material modified by the term "shape memory" may not necessarily need to return to a preselected shape upon application of a stimuli, as under-stood as the classical definition of the "shape memory material." Rather, at least some of the shape memory mate-rials herein may simply hold a selected shape when bent, set, or cured into a specific shape and/or when cooled in a specific shape, regardless of the stimuli applied thereto after. The shape memory materials may be returned to the original shape or changed to a new shape by application of stimuli. For example, a metal wire bent to a first shape may be utilized as the shape memory material, whereinafter the metal wire may be modified to a second shape via physical force applied thereto or via heating.

In an embodiment, the shape memory material may include metal, such as an elemental metal, an alloy, or shape memory alloy. Suitable shape memory metals may include standard steels, stainless steel, carbon alloy steel, head treated steel, aluminum, silver, copper, iron, nickel, zinc, tin, beryllium, or the like. Suitable shape memory alloys may include stainless steel; galvanized steel; aluminum alloys; nickel-titanium alloys, such as Nitinol, Ni—Ti—Cu, Ni—Ti, Co, or the like; copper-based alloys such as Cu—Zn—Al, Cu—Al—Ni, Cu—Al—Sn, or the like; Co—Cr—Ni—Mo alloys (e.g., Elgiloy®) or the like; or any other alloy having shape memory characteristics. As explained above, the shape memory metals or alloys may merely be metals or alloys that may be shaped to a selected configuration. In some examples, the shape memory metals or alloys may return to a primary shape when an external stimuli is applied thereto. In some examples, the outer surface of the shape memory metal may be coated with a polymer, anodized, passivated, or otherwise treated to prevent corrosion.

Shape memory polymers ("SMPs") may include polyure-thane-based SMPs such as a copolymer (e.g., copolyester, polyurethane, polyetherester, etc.) including blocks of one or more of poly(ε-caprolactone), polyethyleneterephthalate (PET), polyethyleneoxide (PEO), polyethylene glycol (PEG), polystyrene, polymethylmethacrylate (PMMA), Polybutylmethacrylate (PBMA), poly(N,N-butadiene), poly(N-methyl-N-oxazoline), polytetrahydrofuran, or poly(buty-lene terephthalate); thermoplastic polymers such as polyether ether ketone (PEEK), nylon, acetal, polytetrafluo-roethylene (PTFE), polysulphone, or the like; Polynor-bonene; other deformable polymers; or any other shape memory polymer.

Turning now to FIGS. 5A-5D, a fluid collection device 500 may include a fluid impermeable barrier having a distal end region 518 and a proximal end region 516 defining an aperture 512 sized and dimensioned to have urine drawn therethrough by a vacuum source. The fluid collection device 500 may include an elongated body 530 that is at least partially fluid permeable and has a portion of the body 530 that is not covered by the fluid impermeable barrier between the distal end region 518 and the proximal end region 516 and that is positioned on the fluid collection device 500 to receive urine discharged from a urethra at least proximate to the portion of the body 530. For example, the fluid impermeable barrier may cover only a portion of the elongated body 530 such that the fluid impermeable barrier is absent from covering the portion of the elongated body 530 between the distal end region 518 and the proximal end region 516. The portion of the elongated body 530 between the distal end region 518 and the proximal end region 516, then, may be free from covering by the fluid impermeable barrier.

In some embodiments, the body 530 includes a fluid permeable membrane 532 and an extruded support 540. In some embodiments, the extruded support 540 may include a foamed or soft material extrusion, such as a closed cell foam extrusion. The extruded support 540 may be generally fluid impermeable and support the fluid permeable membrane 532 of the body 530. The fluid permeable membrane 532 may include any aspect of the fluid permeable body 230 described above, such as a spun nylon fibers fluid permeable membrane. The fluid permeable membrane 532 may cover at least a portion of the extruded support 540, as described in greater detail below.

In some embodiments, the extruded support 540 includes a distal end region 548, a proximal end region 546, and at least one slot 544a extending longitudinally on the extruded support 540. More particularly, the extruded support 540 may include a rear side and a front side including two side slots 544b extending longitudinally on the front side of the extruded support with the slot 544a being positioned between the two side slots 544b. The extruded support 540 may include a plurality of longitudinal ridges at least partially defining the slots 544a, 544b. For example, the slot 544a may be defined at least partially by the longitudinal ridges 545a. The side slots 544b may be defined at least partially by one of the longitudinal ridges 545a and a side longitudinal ridge 545b. The extruded support 540 may include a channel 542 extending longitudinally therethrough. The channel 542 may be completely enclosed within the extruded support 540 such that the extruded support 540 surrounds and/or defines the channel 542. For example, the channel 542 may include an O- or D-shaped channel extending longitudinally through the extruded support 540 from the distal end region 548 to the proximal end region 546.

In some embodiments, the fluid permeable membrane 532 is secured or securable the extruded support 540 such that a portion of the fluid permeable membrane 532 extends across the at least one slot 544a on the front side of the extruded support 540. The portion of the fluid membrane 532 that extends across the at least one slot 544a may include the portion of the body 530 that is not covered by the fluid impermeable barrier (e.g., the fluid impermeable barrier is absent) between the distal end region 518 and the proximal end region 516 and is positioned on the fluid collection device 500 to receive urine discharged from a urethra. A portion of the fluid permeable membrane 532 may be positioned within the two side slots 544b. For example, the fluid collection device 500 may include a shape memory polymer or metal 560 positioned within each of the two side slots 544b and securing the portion of the fluid permeable membrane 532 positioned within the two side slots 544b. In some embodiments, the fluid permeable membrane 532 may include at least a partial loop within each of the two side slots 544b and the shape memory polymer or metal 560 includes an elongated U-shaped shape memory polymer or metal extending through the distal end region 518 and into the at least partial loop in each of the two side slots 544b.

In some embodiments, the fluid impermeable barrier of the fluid collection device 500 includes two caps. For example, the distal end region 518 of the fluid impermeable barrier may include a distal end cap 518 and the proximal end region 516 of the fluid impermeable barrier may include a proximal end cap 516. At least of portion of the distal end cap 518 and the proximal end cap 516 may be shaped complementary to the profile of the body 530. At least a portion of the distal end region 548 of the extruded support 540 may be positioned in the distal end cap 518 and at least a portion of the proximal end region 546 of the extruded support 540 may be positioned in the proximal end cap 516. A reservoir 508 of void space may be positioned between the distal end region 548 of the extruded support 540 and at least a portion of the distal end cap 518 effective to provide fluid communication between the at least one slot 544a and the channel 542 of the extruded support 540. The reservoir 508 may be at least partially defined by portions of each of the distal end region 548 of the extruded support 540 and the distal end cap 518.

In some embodiments, the distal end cap 518 has one or more tabs on the inner surface positioned to prevent or inhibit the extruded support 540 from being pushed too far into the distal end cap 518 that would prevent fluid communication between the at least one slot 544a and the channel 542. Instead, the one or more tabs ensure a reservoir 508 is formed in the distal end cap 518 and fluid communication is maintained between the at least one slot 544a and the channel 542. In some embodiments, the distal end cap 518 includes an alignment feature 519 (e.g., boss) extending partially into the channel 542 at the distal end region 548 of extruded support 540. The alignment feature 519 may be shaped complementary to at least a portion of the channel 542 and may include one or more slits 509, openings, apertures, or perforations configured to provide fluid communication between the channel 542 and the reservoir 508. In some embodiments, at least one of the alignment feature 519 or the channel 542 includes one or more tabs or stops positioned on the alignment feature 519 and/or the channel 542 to prevent the alignment feature 519 from being inserted too far into the channel 542. The one or more tabs or stops in at least one, some, or all embodiments, then, result in the technical effect of insuring fluid communication between channel 542 and the reservoir is maintained. In some embodiments, the distal cap 518 includes wire sockets for a U-shaped wire shape memory polymer or metal 560 or a socket for a malleable strip. For example, the U-shaped wire may include an elongated staple that extends through at least the distal end cap 518. In some embodiments, the elongated staple may extend through the distal end cap 518 and the proximal end cap 516, and may be crimped into the proximal end cap 516. In some embodiments, the distal end cap 518 and the proximal end cap 516 may be bonded to the extruded support 540 or secured to the body 530 with an adhesive.

In some embodiments, the proximal end cap 516 at least partially defines the aperture 512. The aperture 512 may be defined by a portion of the proximal end cap 516 extending outward from the proximal end cap 516 and configured to detachably secure to a conduit (e.g., tube). The proximal end cap 516 also may include an internal port 513 extending partially into the channel 542 in the proximal end region 546 of the extruded support 540. The end caps 516, 518 may include any fluid impermeable material described above in relation to the fluid impermeable barrier 210. In some embodiments, the end caps 516, 518 include a TPE material.

In use, the fluid collection device 500 may be positioned with the fluid permeable membrane 532 covering the at least one slot 544a at least proximate (e.g., adjacent) to the urethra of the user. The ridges 545a on the extruded support 540 may support the fluid permeable membrane 532 such that the at least one slot 544a remains open and void of material (other than urine). With a vacuum creating a negative pressure on the fluid collection device 500, urine discharged on the fluid permeable membrane may be drawn or otherwise enter the at least one slot 544a and flow to the reservoir 508. The vacuum may draw the urine in the reservoir 508 through the alignment feature 519, into the channel 542, through the aperture 512, and out of the fluid collection device 500.

Figures 6A, 6B:
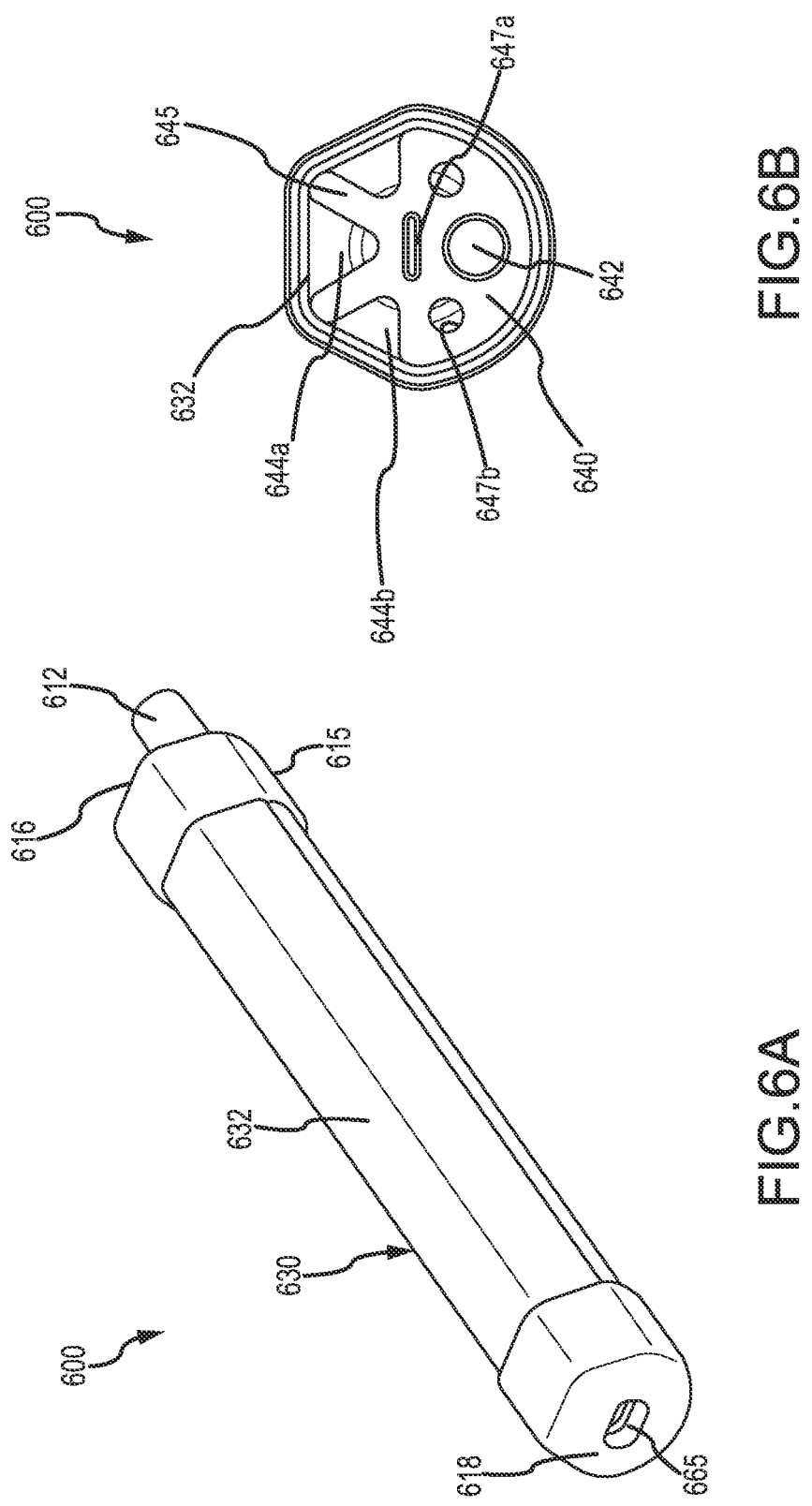
FIG. 6A is a front isometric view of a fluid collection device, according to an embodiment.
FIG. 6B is a transverse cross-sectional view of the fluid collection device of FIG. 6A.
Figure 6C:
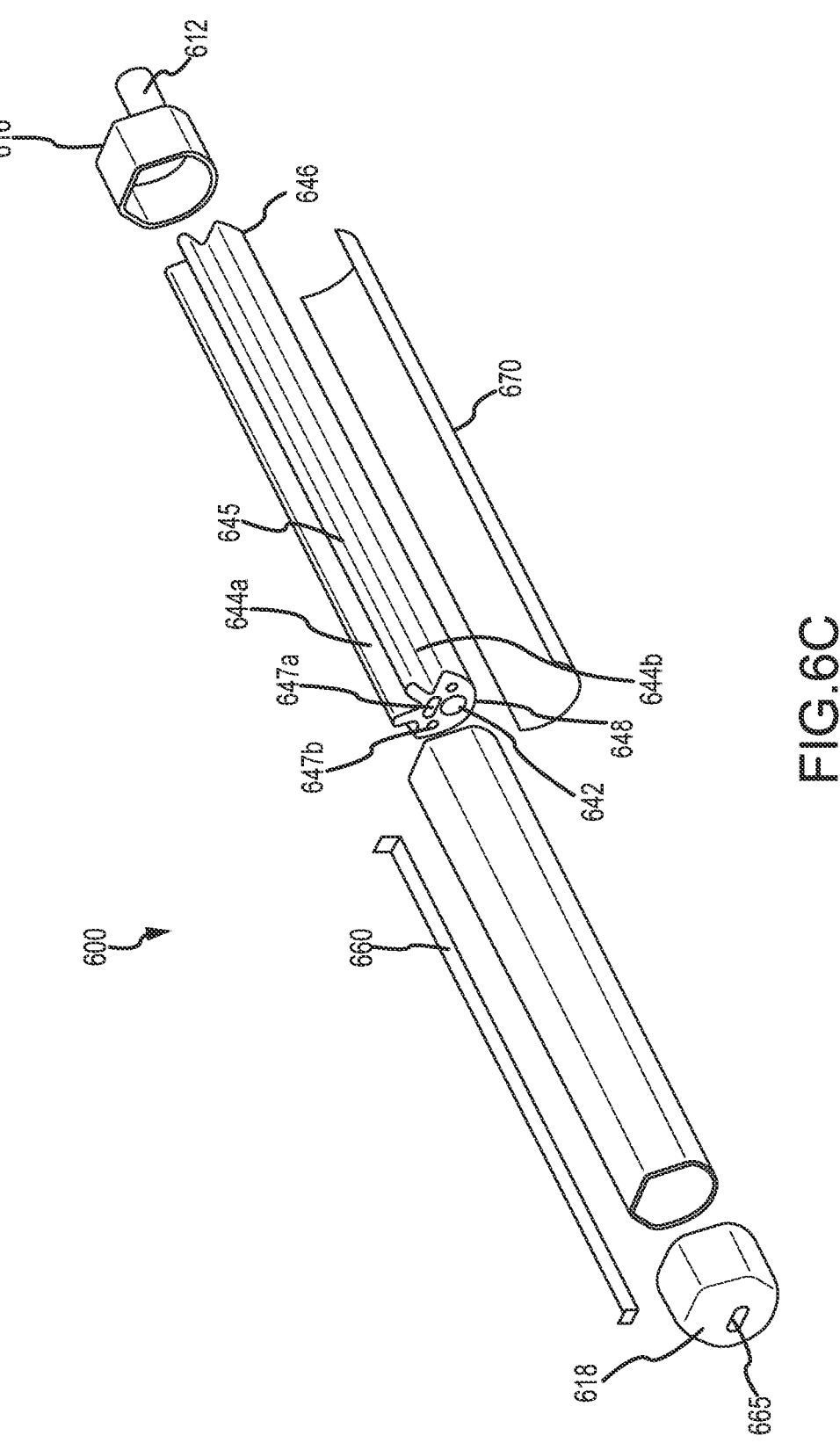
FIG. 6C is an exploded view of the fluid collection device of FIG. 6A.

In some embodiments, a fluid collection device may include a label on the fluid collection device that includes instructions, product identification, and/or user-notated usage data. Turning to FIGS. 6A-6C, a fluid collection device 600 may include a fluid impermeable barrier having a distal end region 618 and a proximal end region 616 defining an aperture 612 sized and dimensioned to have urine drawn therethrough by a vacuum source. The fluid collection device 600 may include an elongated body 630 that is at least partially fluid permeable and has a portion of the body 630 that is not covered by the fluid impermeable barrier (e.g., the fluid impermeable barrier is absent) between the distal end region 618 and the proximal end region 616 and is positioned on the fluid collection device 600 to receive urine discharged from a urethra at least proximate to the portion of the body 230. A label 670 may be secured to the body 630 distal to the portion of the body 630 that is not covered by the fluid impermeable barrier between the distal end region 618 and the proximal end region 616. Unless otherwise noted, the fluid collection device 600 may include any aspect of the fluid collection device 500.

In some embodiments, the body 630 includes a fluid permeable membrane 632 and an extruded support 640. In some embodiments, the extruded support 640 may include a foamed or soft material extrusion, such as a closed cell foam extrusion. The extruded support 640 may be generally fluid impermeable and support the fluid permeable membrane 632 of the body 630. The fluid permeable membrane 632 may include any aspect of the fluid permeable body 230 described above, such as a spun nylon fibers fluid permeable membrane. The fluid permeable membrane 632 may cover at least a portion of the extruded support 640, as described in greater detail below.

In some embodiments, the extruded support 640 includes a distal end region 648, a proximal end region 646, and at least one slot 644a extending longitudinally on the extruded support 640. More particularly, the extruded support 640 may include a rear side and a front side including multiple slots 644a, 644b. The multiple slots may include two side slots 644b and a slot 644a positioned between the two side slots 644b. Each of the multiple slots 644a, 644b may have a center angled relative to the center of other slots of the multiple slots 644a, 644b. The extruded support 640 may include a plurality of longitudinal ridges 645 at least partially defining the multiple slots 644a, 644b.

The extruded support 640 may include a channel 642 extending longitudinally therethrough. The channel 642 may be completely enclosed within the extruded support 640 such that the extruded support 640 surrounds and/or defines the channel 642. For example, the channel 642 may include an O- or D-shaped channel extending longitudinally through the extruded support 640 from the distal end region 648 to the proximal end region 646. The extruded support 640 also may include one or more lumens 647a, 647b extending longitudinally at partially through the extruded support 640 and positioned to receive a shape memory polymer or metal 660. For example, the extruded support 640 may include a lumen 647a sized and dimensioned to receive a malleable polymer or metal and/or two lumens 647b sized and dimensioned to receive arms or prongs of a U-shaped malleable polymer or metal wire. In some embodiments, the distal end cap 618 and the proximal end cap 616 may be bonded to the extruded support 640 or secured to the body 630 with an adhesive.

In some embodiments, the fluid permeable membrane 632 is secured or securable the extruded support 640 such that a portion of the fluid permeable membrane 632 extends across the multiple slots 644a, 644b on the front side of the extruded support 640. The portion of the fluid membrane 632 that extends across the multiple slots 644a, 644b may include the portion of the body 630 that is not covered by the fluid impermeable barrier between the distal end region 618 and the proximal end region 616 and is positioned on the fluid collection device 600 to receive urine discharged from a urethra. In some embodiments, the fluid permeable membrane 632 may wrap around the periphery of the extruded support 640. For example, the fluid permeable membrane 632 may be generally tubular when wrapped around the periphery of the extruded support 640. The ridges 645 on the extruded support 640 may support the fluid permeable membrane 632 such that the multiple slots 644a, 644b remain open and void of material (other than urine). When wrapped around the extruded support 640, the portion of the fluid permeable membrane 632 not covered by the fluid impermeable barrier may include a substantially planar center region covering the slot 644a and two substantially planar side regions covering the slots 644b and angling towards the substantially planar center region.

In some embodiments, the fluid impermeable barrier of the fluid collection device 600 includes two caps. For example, the distal end region 618 of the fluid impermeable barrier may include a distal end cap 618 and the proximal end region 616 of the fluid impermeable barrier may include a proximal end cap 616. At least of portion of the distal end cap 618 and the proximal end cap 616 may be shaped complementary to the profile of the body 630. At least a portion of the distal end region 648 of the extruded support 640 may be positioned in the distal end cap 618 and at least a portion of the proximal end region 646 of the extruded support 640 may be positioned in the proximal end cap 616. A reservoir (not shown) of void space may be positioned between the distal end region 648 of the extruded support 640 and at least a portion of the distal end cap 618 effective to provide fluid communication between the multiple slots 644a, 644b and the channel 642 of the extruded support 640. The reservoir may be at least partially defined by portions of each of the distal end region 648 of the extruded support 640 and the distal end cap 618, similar to the reservoir 508 of the fluid collection device 500.

In some embodiments, the distal end cap 618 has one or more tabs on the inner surface positioned to prevent or inhibit the extruded support 640 from being pushed too far into the distal end cap 618 that would prevent fluid communication between the multiple slots 644a, 644b and the channel 642. Instead, the one or more tabs ensure the reservoir is formed in the distal end cap 618 and fluid communication is maintained between the multiple slots 644a, 644b and the channel 642. In some embodiments, the distal end cap 618 includes an alignment feature (not shown) similar or the same as the alignment feature on the distal end cap 518 of the fluid collection device 500. In some embodiments, at least one of the alignment feature or the channel 642 includes one or more tabs or stops positioned on the alignment feature and/or the channel 642 to prevent the alignment feature from being inserted too far into the channel 642. The one or more tabs or stops, then, may result in insuring fluid communication between the channel 642 and the reservoir is maintained. The distal end cap 618 may include a receiver for the shape memory polymer or metal 660. For example, the distal end cap 618 may include a socket 665 for a strip or U-shaped wire shape memory polymer or metal 660.

In some embodiments, the proximal end cap 616 at least partially defines the aperture 612. The aperture 612 may be defined by a portion of the proximal end cap 616 extending outward from the proximal end cap 516 and configured to detachable secure to a conduit (e.g., tube). The proximal end cap 616 also may include an internal port (not shown) extending partially into the channel 642 in the distal end region 646 of the extruded support 640. The end caps 616, 618 may include any fluid impermeable material described above in relation to the fluid impermeable barrier 210. In some embodiments, the end caps 616, 618 include a TPE material.

In some embodiments, the fluid impermeable barrier of the fluid collection device 600 includes a substantially fluid impermeable sheet 670 secured to a portion of the body 630 with an adhesive and extending at least partially between the proximal end cap 616 and the distal end cap 618. The fluid impermeable sheet 670 may include a waterproof label and/or adhesive configured to prevent fluid transfer around the periphery of the body 630. In some embodiments, the fluid impermeable sheet 670 may include any fluid impermeable material described above in relation to the fluid impermeable barrier 210, such as TPE. In some embodiments, the fluid impermeable sheet 670 may be sprayed coated on the fluid permeable membrane 632. The fluid impermeable sheet 670 also may include artwork, instructions, product identification, and/or user-notated usage data. The incorporation of labeling in at least one, some, or all embodiments results in the technical effect of reducing packaging required for the fluid collection device 600, providing information or instructions to the user in a place that is less likely to be discarded by the user, and/or providing a space to record relevant data pertaining to fluid collection of the user. The fluid permeable sheet 670 may be adhered to the fluid permeable membrane 632 before securing the body 630 to the proximal end cap 616 and/or the distal end cap 618.

In use, the fluid collection device 600 may be positioned with the fluid permeable membrane 632 that covers the multiple slots 644a, 644b at least proximate (e.g., adjacent) to the urethra of the user. The ridges 645 on the extruded support 640 may support the fluid permeable membrane 632 such that the multiple slots 644a, 644b remain open and void of material (other than urine). With a vacuum creating a negative pressure on the fluid collection device 600, urine discharged on the fluid permeable membrane 632 may be drawn or otherwise enter one or more of the slots 644a, 644b and flow to the reservoir. The vacuum may draw the urine in the reservoir through the alignment feature, into the channel 642, through the aperture 612, and out of the fluid collection device 600.

Figure 7:
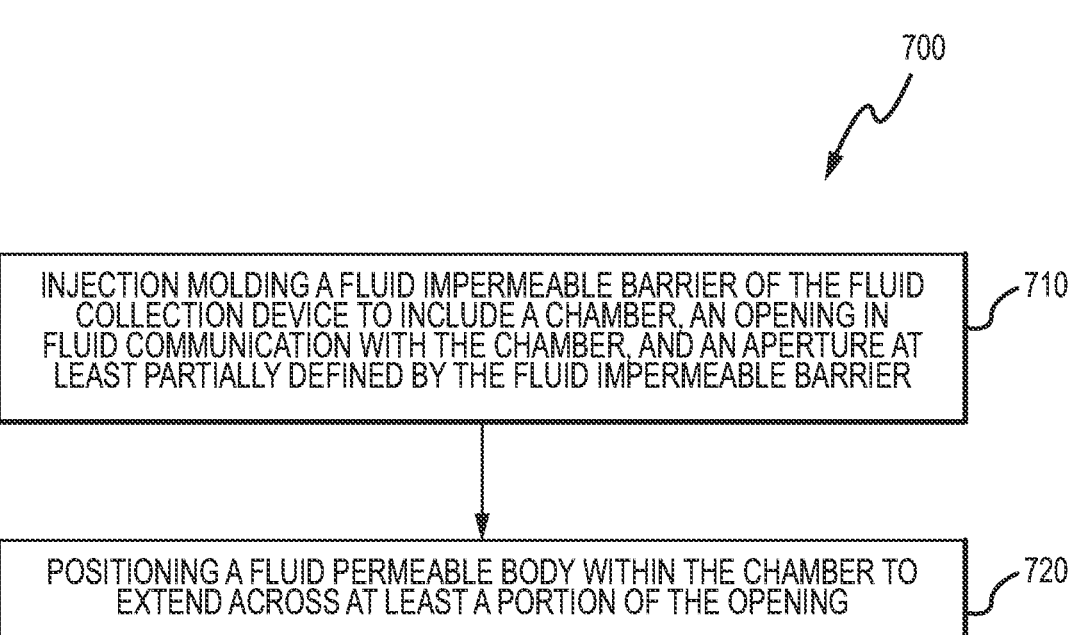
FIG. 7 is a flowchart of a method of manufacturing a fluid collection device, according to an embodiment.

FIG. 7 is a flow diagram of a method 700 of manufacturing a fluid collection device, according to an embodiment. The method 700 includes an act 710 of injection molding a fluid impermeable barrier of the fluid collection device to include a chamber, an opening in fluid communication with the chamber, and an aperture at least partially defined by the fluid impermeable barrier. The opening may be positioned on the fluid collection device to receive urine discharged from a urethra at least proximate to the opening and the aperture may be sized and dimensioned to have urine drawn therethrough by a vacuum source. The act 710 of injection molding a fluid impermeable barrier of the fluid collection device may include injection molding the fluid impermeable barrier including at least one of thermoplastic polyurethane or thermoplastic elastomer. The method 700 also includes an act 720 of positioning a fluid permeable body within the chamber to extend across at least a portion of the opening.

In some embodiments, the method 700 may further include positioning an inlet of a conduit at least partially within chamber. In these and embodiments, the act 710 of injection molding a fluid impermeable barrier of the fluid collection device may include injection molding the fluid impermeable barrier to include a top side defining the opening, a rear side opposite to the front end, a proximal end region defining the aperture, a distal end region opposite to the proximate end region, and one or more protrusions positioned within the chamber at the distal end region to space at least a portion of the inlet from the distal end region of the fluid impermeable barrier. In some embodiments, injection molding the fluid impermeable barrier may include injection molding the fluid impermeable barrier to be substantially cylindrical and positioning an inlet of a conduit at least partially within chamber may include inserting the conduit at least partially through the fluid permeable body and the aperture.

In some embodiments of the method 700, injection molding the fluid impermeable barrier may include injection molding the fluid impermeable barrier to (1) define an internal port positioned within the fluid collection device and in fluid communication with the aperture and (2) include an external port at the proximal end region defining the aperture. The external port may be sized and dimensioned to detachably secure to an additional conduit effective provide fluid communication between the additional conduit and the conduit. In these and other embodiments, the act of positioning an inlet of a conduit at least partially within chamber may include positioning the inlet of the conduit at least partially within the chamber and positioning an outlet of the conduit within the port.

In some embodiments, the act 710 of injection molding the fluid impermeable barrier may include injection molding the fluid impermeable barrier to include an elongated planar portion on the rear side extending at least partially between a proximal end region and a distal end region and an arced region on the front side at each of the distal end region and the proximal end region. In these and other embodiments, the method 700 may further comprise an act of positioning the conduit in a channel of an elongated fluid permeable support of the fluid permeable body.

In some embodiments, the method 700 may further include positioning a fluid permeable membrane around the fluid permeable support and the conduit before positioning the fluid permeable body within the chamber to extend across at least the portion of the opening. In these and other embodiments, the method 700 may further include securing a support member to the rear side of the fluid impermeable barrier, the support member including a shape memory polymer or a metal.

The acts of the method 700 described above are for illustrative purposes. For example, the acts of the method 700 can be performed in different orders, split into multiple acts, modified, supplemented, or combined. In an embodiment, one or more of the acts of the method 700 can be omitted from the method 700. Any of the acts of the method 700 can include manufacturing of any of the fluid collection devices and systems disclosed herein.

Figure 8:
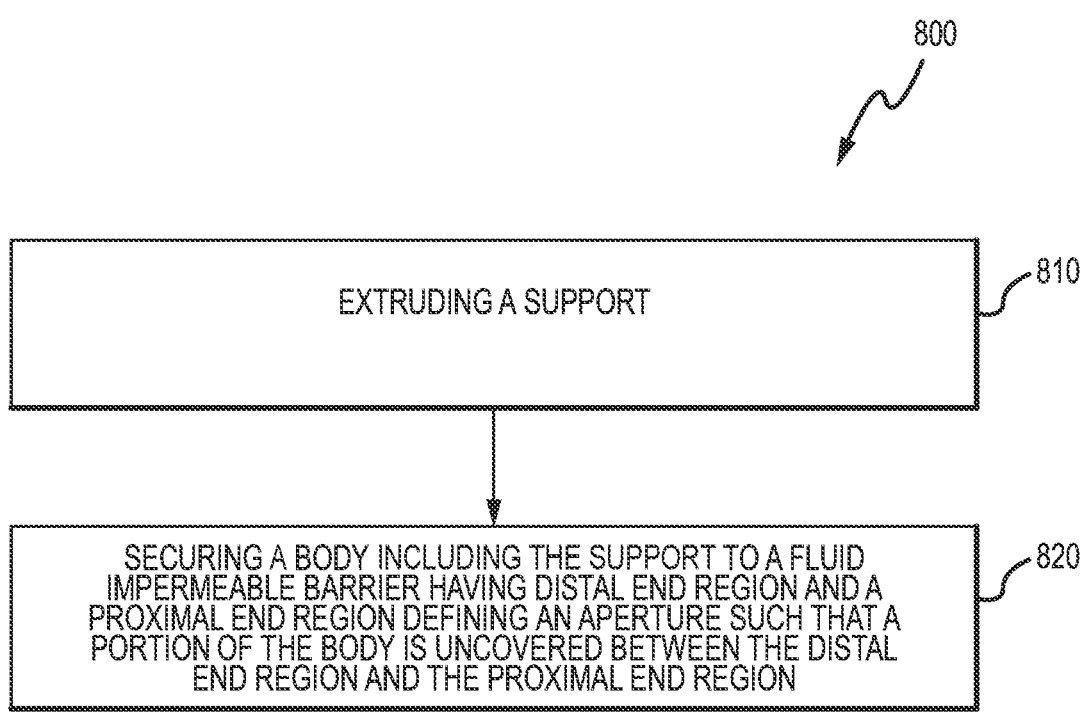
FIG. 8 is a flowchart of a method of manufacturing a fluid collection device, according to an embodiment.

FIG. 8 is a flow diagram of a method 800 of manufacturing a fluid collection device, according to an embodiment. The method 800 includes an act 810 of extruding a support to include at least one slot extending longitudinally on the extruded support. In some embodiments, extruding a support includes extruding a closed cell foam extrusion forming the support. The method 800 also includes an act 820 of securing a body including the extruded support and that is at least partially fluid permeable to a fluid impermeable barrier having distal end region and a proximal end region defining an aperture such that a portion of the body is uncovered by the fluid impermeable barrier between the distal end region and the proximal end region and positioned on the fluid collection device to receive urine discharged from a urethra at least proximate to the portion of the body. The aperture is in fluid communication with the at least one slot and sized and dimensioned to have urine drawn therethrough by a vacuum source.

In some embodiments, the method 800 includes an act of securing a fluid permeable membrane to the extruded support to form the body that is at least partially fluid permeable. The act 810 may include extruding the support to include a channel extending longitudinally therethrough. In these and other embodiments, the method 800 may include an act of aligning the channel with the aperture of the fluid impermeable barrier before or when securing the body to a fluid impermeable barrier. In some embodiments the act 820 may include securing a proximal end cap to a proximal end region of the extruded support and securing a distal end cap to a distal end region of the extruded support to form a reservoir of void space between the distal end region of the extruded support and at least a portion of the distal end cap, the reservoir providing fluid communication between the at least one slot and the channel. The method 800 also may include securing an additional fluid impermeable barrier to a rear side of the extruded support with an adhesive before securing the distal end cap to the distal end region of the extruded support and securing the proximal end cap to the proximal end region of the extruded support. The additional fluid impermeable barrier may extend continuously between the distal end cap and proximal end cap when the body is secured to the fluid impermeable barrier.

In some embodiments, the act 810 may include extruding the support to include a front side including two side slots extending longitudinally on the front side of the extruded support and the at least one slot extending longitudinally on the front side of the extruded support between the two side slots. In these and other embodiments, the act 820 may include securing portions of the fluid permeable membrane in the two side slots with a shape memory polymer or metal extending through the two side slots, with a portion of the fluid permeable membrane extending at least partially across the front side of the extruded support between the two side slots to cover the one or more slots and include the portion of the body that is uncovered between the distal end region and the proximal end region of the fluid impermeable barrier. The act 820 also may include inserting an elongated U-shaped shape memory polymer or metal through the distal end cap and into the two side slots.

In some embodiments, the act 810 includes extruding the support including a front side including three slots each having a center angled relative to the center of other slots of the three slots. In these and other embodiments, the act 820 may include wrapping the fluid permeable membrane around the front side and the rear side of the extruded support such that a portion of the fluid permeable membrane covers the three slots to include the portion of the body that is uncovered between the distal end region and the proximal end region of the fluid impermeable barrier. The method 800 also may include inserting a shape memory polymer or metal to extend longitudinally through the distal end cap and at least a portion of the extruded support.

In some embodiments, the method 800 also includes an act of inserting an alignment feature in the distal end cap into the channel at the distal end region of extruded support and inserting an internal port in the proximal end cap into the channel. The internal port may be in fluid communication with the aperture, and the alignment feature may include one or more slits providing fluid communication between the reservoir and the channel.

The acts of the method 800 described above are for illustrative purposes. For example, the acts of the method 800 can be performed in different orders, split into multiple acts, modified, supplemented, or combined. In an embodiment, one or more of the acts of the method 800 can be omitted from the method 800. Any of the acts of the method 800 can include manufacturing of any of the fluid collection devices and systems disclosed herein.

As used herein, the term "about" or "substantially" refers to an allowable variance of the term modified by "about" or "substantially" by ±10% or ±5%. Further, the terms "less than," "or less," "greater than," "more than," or "or more" include, as an endpoint, the value that is modified by the terms "less than," "or less," "greater than," "more than," or "or more."

While various aspects and embodiments have been disclosed herein, other aspects and embodiments are contemplated. The various aspects and embodiments disclosed herein are for purposes of illustration and are not intended to be limiting.

What is claimed is:

1. A fluid collection device, comprising:
 a fluid impermeable barrier having a distal end region including a distal end cap and a proximal end region including a proximal end cap defining an aperture sized and dimensioned to have urine drawn therethrough by a vacuum source, the proximal end cap being separate from the distal end cap; and
 an elongated body having the distal end cap and the proximal end cap secured thereto such that the elongated body has a portion of the elongated body between the distal end region and the proximal end region that is free from being covered by the fluid impermeable barrier and positioned on the fluid collection device to receive urine discharged from a urethra at least proximate to the portion of the elongated body, the elongated body including at least an extruded support; and
 a shape memory polymer or metal that is positioned within the extruded support of the elongated body.

2. The fluid collection device of claim 1, wherein the elongated body includes:
 the extruded support having a distal end region having the distal end cap secured thereto, a proximal end region having the proximal end cap secured thereto, and at least one slot extending longitudinally on the extruded support; and
 a fluid permeable membrane covering the at least one slot on the extruded support.

3. The fluid collection device of claim 2, wherein the extruded support includes a channel extending longitudinally therethrough and in fluid communication with the at least one slot and the aperture of the fluid impermeable barrier.

4. The fluid collection device of claim 3, wherein:

the distal end region of the fluid impermeable barrier includes a reservoir of void space being positioned between the distal end region of the extruded support and at least a portion of the distal end cap effective to provide fluid communication between the at least one slot and the channel.

5. The fluid collection device of claim 4, wherein the fluid impermeable barrier includes a substantially fluid impermeable sheet secured to a portion of the elongated body with an adhesive and extending between the proximal end cap and the distal end cap.

6. The fluid collection device of claim 4, wherein:

the extruded support includes a rear side and a front side including two side slots extending longitudinally on the front side of the extruded support, the at least one slot being positioned between the two side slots;

a portion of the fluid permeable membrane is positioned within the two side slots; and a portion of the fluid permeable membrane extends at least partially across the at least one slot.

7. The fluid collection device of claim 6, wherein the shape memory polymer or metal is positioned within each of the two side slots and securing the portion of the fluid permeable membrane positioned within the two side slots.

8. The fluid collection device of claim 7, wherein the shape memory polymer or metal includes an elongated U-shaped shape memory polymer or metal extending through the distal end cap and into the two side slots.

9. The fluid collection device of claim 4, wherein the extruded support includes a rear side and a front side, the at least one slot including three slots on the front side each having a center angled relative to the center of other slots of the three slots.

10. The fluid collection device of claim 9, wherein the fluid permeable membrane is wrapped around the front side and the rear side of the extruded support such that a portion of the fluid permeable membrane covers the three slots and extends at least partially across the opening of the fluid impermeable barrier.

11. The fluid collection device of claim 9, further comprising the shape memory polymer or metal extending longitudinally through the distal end cap and at least a portion of the extruded support.

12. The fluid collection device of claim 4, wherein the distal end cap includes an alignment feature extending partially into the channel at the distal end region of extruded support and the proximal end cap includes an internal port extending partially into the channel, the alignment feature included one or more slits providing fluid communication between the reservoir and the channel.

13. The fluid collection device of claim 12, wherein the extruded support includes a closed cell foam extrusion.

14. The fluid collection device of claim 1, wherein at least a portion of the shape memory polymer or metal includes a strip of shape memory polymer or metal positioned within the extruded support of the elongated body.

15. The fluid collection device of claim 1, wherein at least a portion of the shape memory polymer or metal includes a wire of shape memory polymer or metal positioned within the extruded support of the elongated body.

* * * * *